United States Patent
Krall et al.

(10) Patent No.: US 9,884,122 B2
(45) Date of Patent: Feb. 6, 2018

(54) SMALL MOLECULE DRUG CONJUGATES

(71) Applicant: Philochem AG, Otelfingen (CH)

(72) Inventors: Nikolaus Krall, Vienna (AT); Willy Decurtins, Horgen (CH); Dario Neri, Buchs (CH); Jörg Scheuermann, Würenlos (CH); Moreno Wichert, Wangen-Nuolen (CH)

(73) Assignee: Eth Zurich, Zurich (CH)

( * ) Notice: Subject to any disclaimer, the term of this patent is extended or adjusted under 35 U.S.C. 154(b) by 0 days.

(21) Appl. No.: 15/226,439

(22) Filed: Aug. 2, 2016

(65) Prior Publication Data

US 2017/0035892 A1 Feb. 9, 2017

Related U.S. Application Data

(63) Continuation of application No. PCT/EP2015/052214, filed on Feb. 3, 2015.

(30) Foreign Application Priority Data

Feb. 3, 2014 (GB) .................................. 1401819.6
Apr. 29, 2014 (GB) .................................. 1407530.3
Nov. 10, 2014 (GB) .................................. 1419994.7

(51) Int. Cl.
| | |
|---|---|
| A61K 47/55 | (2017.01) |
| A61K 47/48 | (2006.01) |
| A61K 31/535 | (2006.01) |
| A61K 38/05 | (2006.01) |
| A61K 45/06 | (2006.01) |
| C07B 59/00 | (2006.01) |
| C07K 5/083 | (2006.01) |
| A61K 47/65 | (2017.01) |
| A61K 47/54 | (2017.01) |

(52) U.S. Cl.
CPC ...... *A61K 47/48061* (2013.01); *A61K 31/535* (2013.01); *A61K 38/05* (2013.01); *A61K 45/06* (2013.01); *A61K 47/545* (2017.08); *A61K 47/55* (2017.08); *A61K 47/65* (2017.08); *C07B 59/008* (2013.01); *C07K 5/0808* (2013.01); *C07B 2200/05* (2013.01)

(58) Field of Classification Search
None
See application file for complete search history.

(56) References Cited

U.S. PATENT DOCUMENTS

2006/0057068 A1 3/2006 Supuran et al. ............... 424/9.1

FOREIGN PATENT DOCUMENTS

| WO | WO 2004/048544 A2 | 6/2004 | |
|---|---|---|---|
| WO | WO 2005/082023 A2 | 9/2005 | |
| WO | WO 2011/098610 A1 | 8/2011 | .............. A61K 31/18 |
| WO | WO 2013/167994 A1 | 11/2013 | .......... C07D 285/135 |

OTHER PUBLICATIONS

Buller et al., "Selection of Carbonic Anhydrase IX Inhibitors from One Million DNA-Encoded Compounds," ACS Chemical Biology, vol. 6, pp. 336-344, Dec. 27, 2010.
Krall et al., "Small Targeted Cytotoxics: Current State and Promises from DNA-Encoded Chemical Libraries," Angewandte Chemie International Edition, vol. 52, pp. 1384-1402, 2013.
Krall et al., "A Small-Molecule Drug Conjugate for the Treatment of Carbonic Anhydrase IX Expressing Tumors," Angewandte Chemie International Edition, vol. 53, pp. 4231-4235, 2014.
Wichert et al., "Dual-display of small molecules enables the discovery of ligand pairs and facilitates affinity maturation," Nature Chemistry, vol. 7, No. 3, pp. 241-249, 2015.
International Searching Authority, International Search Report—International Application No. PCT/EP2015/052214, dated May 4, 2015, together with the Written Opinion of the International Searching Authority, 13 pages.
International Searching Authority, International Preliminary Report on Patentability—International Application No. PCT/EP2015/052214, dated Aug. 18, 2016, together with the Written Opinion of the International Searching Authority, 9 pages.
Cazzamalli et al., "Acetazolamide Serves as Selective Delivery Vehicle for Dipeptide-Linked Drugs to Renal Cell Carcinoma," Molecular Cancer Therapeutics, vol. 15, No. 12, pp. 2926-2935, Dec. 2016.
Cazzamalli et al., "Linker Stability Influences the Anti-Tumor Activity of Acetazolamide-Drug Conjugates for the Therapy of Renal Cell Carcinoma," Journal of Controlled Release, vol. 246, pp. 39-45, Jan. 28, 2017.
Krall et al., "A 99mTc-Labeled Ligand of Carbonic Anhydrase IX Selectively Targets Renal Cell Carcinoma In Vivo," Journal of Nuclear Medicine, vol. 57, No. 6, pp. 943-949, Jun. 2016.

*Primary Examiner* — Fred H Reynolds
(74) *Attorney, Agent, or Firm* — Sunstein Kann Murphy & Timbers LLP

(57) ABSTRACT

A targeted therapeutic agent comprising a compound of formula I:

$$B\text{-}L\text{-}D \qquad (I),$$

wherein: B is a low molecular weight binding moiety for Carbonic Anhydrase IX (CAIX); D is a drug moiety; and L is a linker group that undergoes cleavage in vivo for releasing said drug moiety in an active form. The drug moiety is suitably a cytotoxic agent for targeted delivery to cancer cells expressing CAIX. The binding moiety B suitably comprises a sulfonamidothiadiazole moiety. The binding moiety B may comprise one, two or more groups capable of binding to CAIX. The linker group suitably comprises a disulfide bond and/or a triazole group and/or a cleavable peptide group.

6 Claims, 14 Drawing Sheets

B1 R = H
B3 R = IRDye750

B2 R = H
B4 R = IRDye750

B7

B8  X = OH

- Vehicle;
- ▼ ligand B2 (8 x 35 nmol)
- ▲ Targeted Conjugate B7 (8 x 35 nmol)
- ◆ Untargeted Conjugate B8 (8 x 35 nmol)

SMALL MOLECULE DRUG CONJUGATES

CROSS-REFERENCE TO RELATED APPLICATIONS

This application is a continuation of PCT application PCT/EP2015/052214 filed Feb. 3, 2015, which claims benefit of GB 1419994.7 filed Nov. 10, 2014, GB 1407530.3 filed Apr. 29, 2014, and GB 1401819.6 filed Feb. 3, 2014. The contents of the above patent applications are incorporated by reference herein in their entirety.

FIELD OF THE INVENTION

The present invention relates to the field of small molecule targeted drug conjugates (SMDCs) for the treatment of disease. In particular, the invention relates to SMDCs formed of a low molecular weight ligand for binding to Carbonic Anhydrase IX (CAIX), conjugated to a drug by a cleavable linker for delivery of the drug to targeted tissues or cells. In one embodiment, the present invention relates to the application of such SMDCs for the delivery of drugs that can kill or inhibit tumour cells.

BACKGROUND

The use of cytotoxic agents is at the basis of the treatment of cancer and other pathological conditions. Ideally cytotoxic agents should accumulate at site of disease, sparing normal tissues. In reality this does not happen. Many anti-cancer drugs do not preferentially accumulate in solid tumors. Indeed, it has been demonstrated in tumor-bearing mice that only a minimal portion of the injected drug reaches the neoplastic mass in comparison to the amount of cytotoxic agent that reaches healthy organs.

The targeted delivery of highly potent cytotoxic agents into diseased tissues is therefore desirable for the treatment of cancer and other serious conditions. By attaching a therapeutic effector through a cleavable linker to a ligand specific to a marker of disease, the effector preferentially accumulates and acts at the intended site of action, thus increasing the effectively applied dose while reducing side effects. To date, monoclonal of antibody-drug conjugates (ADCs) has led to the recent approval of two ADCs for applications in oncology: brentuximab vedotin and trastuzumab emtansine.

However, antibodies are large macromolecules and thus often have difficulties penetrating deeply into solid tumors. In addition, they can be immunogenic and typically long circulation times can lead to premature drug release and undesired side effects. Moreover, the production of ADCs is expensive, reflecting the need for clinical-grade manufacturing of antibodies, drugs and the resulting conjugates.

The use of smaller ligands as delivery vehicles such as peptides or small drug-like molecules could potentially overcome some of the abovementioned problems. Their reduced size should aid tissue penetration, they should be non-immunogenic and amenable to classic organic synthesis thus reducing manufacturing costs. The favorable properties of drug conjugates using folic acid or ligands against prostate-specific membrane antigen (PSMA) as delivery vehicles have been demonstrated and a folate conjugate has recently entered Phase III clinical studies. However, only a few such conjugates have been successfully identified.

WO2006137092 describes the use of fluorophore-labeled Carbonic Anhydrase IX inhibitors for the treatment of cancers by inhibiting the activity of CAIX and thereby reversing acidification of the extracellular environment of the tumour. There is no suggestion to use the CAIX inhibitors for targeting cytotoxic agents. Further CAIX inhibitors for the treatment of cancer are described in WO2011098610 and WO2004048544.

The present inventors have found small molecule drug conjugates that target Carbonic Anhydrase IX (CAIX) expressing tumors.

SUMMARY OF THE INVENTION

According to the first aspect of the invention, therefore, there is provided a targeted therapeutic agent comprising a compound of formula:

$$B\text{-}L\text{-}D \quad (I),$$

wherein:
B is a low molecular weight binding moiety for a Carbonic Anhydrase;
D is a drug moiety; and
L is a linker group that undergoes cleavage in vivo for releasing said drug moiety in an active form.

The binding moiety B suitably binds to a tumor-associated carbonic anhydrase enzyme, most preferably it binds to Carbonic Anhydrase IX (CAIX). The binding to the carbonic anhydrase is suitably selective or specific, whereby the binding moiety B accumulates in vivo at sites, such as tumors, where carbonic anhydrase is present at elevated levels. Alternatively or additionally, the binding moiety may bind to other carbonic anhydrases such as Carbonic Anhydrase XII.

Suitably, the compound of Formula (I) has a molecular weight less than about 8,000, more suitably less than about 5000, and most suitably less than about 2000. In contrast to antibodies, small molecules can diffuse out of blood vessels in a matter of seconds. The distribution is not restricted to perivascular space, but involves also deep penetration into tissues. This results in faster, deeper and more efficient drug targeting by the agents of the invention.

In another aspect, the present invention provides a targeted therapeutic agent in accordance with the first aspect of the invention, for use in the treatment of a neoplastic disease, preferably for the treatment of a solid tumor, more preferably for the treatment of renal cell carcinoma.

In another aspect, the present invention provides a pharmaceutical composition comprising a targeted therapeutic agent according to the first aspect of the invention.

In another aspect, the present invention provides a product comprising a compound of Formula (I) as defined herein and a cleavage agent for cleaving said cleavable linker L, as a combined preparation for sequential administration in the treatment of cancer.

In another aspect, the present invention provides a method of treating a neoplastic disease, preferably a solid tumor such as renal cell carcinoma, comprising administering an effective amount of a pharmaceutical composition according to the present invention to a patient in need thereof. In embodiments, the administration of said pharmaceutical composition is followed after a suitable interval of time by administration of a cleavage agent for cleaving said cleavable linker L.

Any feature described herein as suitable, optional, or preferred in relation to any one aspect of the invention may likewise be suitable, optional or preferred in relation to any other aspect of the invention.

DETAILED DESCRIPTION OF THE INVENTION

Figure 1:
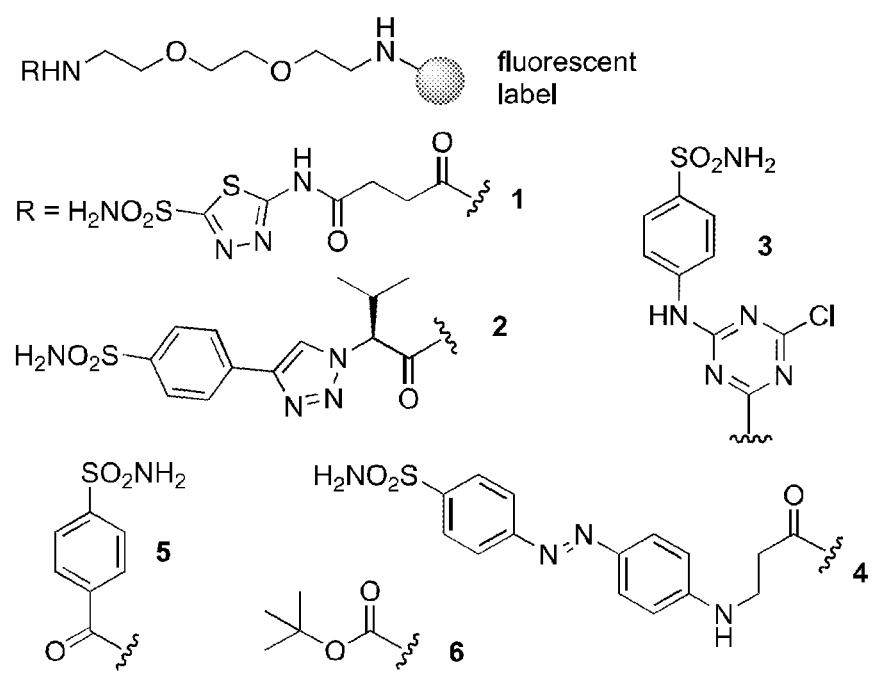
FIG. 1 shows chemical structures of ligand-linker-dye conjugates synthesised for in vitro binding and in vivo targeting studies.

Unless defined otherwise, all technical and scientific terms used herein have the same meaning as commonly understood by those of ordinary skill in the art, such as in the arts of peptide chemistry, cell culture, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4th ed., John Wiley & Sons, Inc.). All publications cited herein are incorporated herein by reference in their entirety for the purpose of describing and disclosing the methodologies, reagents, and tools reported in the publications that might be used in connection with the invention.

Unless otherwise stated, the following definitions apply to chemical terms used in connection of compounds of the invention and compositions containing such compounds.

Alkyl refers to a branched or unbranched saturated hydrocarbyl radical. Suitably, the alkyl group comprises from about 3 to about 30 carbon atoms, for example from about 5 to about 25 carbon atoms.

Alkenyl refers to a branched or unbranched hydrocarbyl radical containing one or more carbon-carbon double bonds. Suitably, the alkenyl group comprises from about 3 to about 30 carbon atoms, for example from about 5 to about 25 carbon atoms.

Alkynyl refers to a branched or unbranched hydrocarbyl radical containing one or more carbon-carbon triple bonds. Suitably, the alkynyl group comprises from about 3 to about 30 carbon atoms, for example from about 5 to about 25 carbon atoms.

Halogen refers to fluorine, chlorine, bromine or iodine, preferably fluorine or chlorine.

Cycloalkyl refers to an alicyclic moiety, suitably having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbornyl, bicyclo[2.2.2]octyl and the like.

Aryl refers to an aromatic ring system comprising 6, 7, 8, 9, 10, 11, 12, 13, 14, 15 or 16 ring carbon atoms. Aryl may be a polycyclic ring system, having two or more rings, at least one of which is aromatic. This term includes reference to groups such as phenyl, naphthyl, fluorenyl, azulenyl, indenyl, anthryl and the like.

The prefix (hetero) herein signifies that one or more of the carbon atoms of the group may be substituted by nitrogen, oxygen, phosphorus, silicon or sulfur. Heteroalkyl groups include for example, alkyloxy groups and alkythio groups. Heterocycloalkyl or heteroaryl groups herein may have from 3, 4, 5, 6, 7, 8, 9, 10, 11, 12, 13, 14, 15 or 16 ring atoms, at least one of which is selected from nitrogen, oxygen, phosphorus, silicon and sulfur. In particular, a 3- to 10-membered ring or ring system and more particularly a 5- or 6-membered ring, which may be saturated or unsaturated. For example, selected from oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, 1,3-Dioxo-1,3-dihydroisoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, [beta]-carbolinyl, phenanthridinyl, acridinyl, perimidinyl, phenanthrolinyl, furazanyl, phenazinyl, phenothiazinyl, phenoxazinyl, chromenyl, isochromanyl, chromanyl, 3,4-dihydro-2H-isoquinolin-1-one, 3,4-dihydro-2H-isoquinolinyl, and the like.

Where a substituent herein is a peptide, the peptide suitably comprises from 1 to 100 amino acid residues, for example from about 2 to about 30 amino acid residues.

Where a substituent herein is an oligosaccharide, the oligosaccharide suitably comprises from 1 to 100 saccharide residues, for example from about 2 to about 30 saccharide residues.

"Substituted" signifies that one or more, especially up to 5, more especially 1, 2 or 3, of the hydrogen atoms in said moiety are replaced independently of each other by the corresponding number of substituents. The term "optionally substituted" as used herein includes substituted or unsubstituted. It will, of course, be understood that substituents are only at positions where they are chemically possible, the person skilled in the art being able to decide (either experimentally or theoretically) without inappropriate effort whether a particular substitution is possible. For example, amino or hydroxy groups with free hydrogen may be unstable if bound to carbon atoms with unsaturated (e.g. olefinic) bonds. Additionally, it will of course be understood that the substituents described herein may themselves be substituted by any substituent, subject to the aforementioned restriction to appropriate substitutions as recognised by the skilled person.

Substituents may suitably include halogen atoms and halomethyl groups such as $CF_3$ and $CCl_3$; oxygen containing groups such as oxo, hydroxy, carboxy, carboxyalkyl, alkoxy, alkoyl, alkoyloxy, aryloxy, aryloyl and aryloyloxy; nitrogen containing groups such as amino, alkylamino, dialkylamino, cyano, azide and nitro; sulfur containing groups such as thiol, alkylthiol, sulfonyl and sulfoxide; heterocyclic groups which may themselves be substituted; alkyl groups, which may themselves be substituted; and aryl groups, which may themselves be substituted, such as phenyl and substituted phenyl. Alkyl includes substituted and unsubstituted benzyl.

Where two or more moieties are described as being "each independently" selected from a list of atoms or groups, this means that the moieties may be the same or different. The identity of each moiety is therefore independent of the identities of the one or more other moieties.

Derivative.

A derivative includes the chemical modification of a compound. Examples of such modifications include without limitation the replacement of a hydrogen by a halo group, an alkyl group, an acyl group or an amino group and the like. Derivatives further include esters and the like that can undergo hydrolysis to release the compound. Derivatives further includes salts of the compound. The modification may increase or decrease one or more hydrogen bonding interactions, charge interactions, hydrophobic interactions, van der Waals interactions and/or dipole interactions.

Analog.

This term encompasses any enantiomers, racemates and stereoisomers, as well as all pharmaceutically acceptable salts and hydrates of such compounds.

Target

The present invention targets Carbonic Anhydrase, in particular Carbonic Anhydrase IX (CAIX) proteins that are expressed on tumours. CAIX is over-expressed in many different forms of cancer such as glioblastoma, colorectal and breast cancer as a marker of hypoxia, while being almost undetectable in normal adult tissues, thus representing a very attractive antitumor target. In renal cell carcinoma it is often constitutively expressed and is among the best-characterized cell-surface markers of this disease Binding Moiety Suitably, the binding moiety is a low molecular weight binding moiety. Thus, the binding moiety is preferably not an antibody or an antibody fragment. Suitably, the molecular weight of the binding moiety is less than about 10,000, preferably less than about 3000, most preferably less than about 1000. In embodiments, the binding moiety (ligand) is a peptide. In other embodiments, the binding moiety (ligand) is not a peptide. The possibility to step away from antibodies and to use small organic or inorganic molecules as ligands allows those molecules to have complexity with is amenable to chemical synthesis. The core of the structures can vary from pure organic compounds to structures that are based on peptide scaffolds and even inorganic structures such as boron and other clusters The binding moiety may be based on a compound that is known to bind strongly to the target. Alternatively, the binding moiety may be identified by one or more known screening methods for identifying compounds that bind selectively to the target protein of interest.

For example, improved variants of the ligands described below, or new ligands for binding selectively to target proteins of interest, can be found by screening methods using modern medicinal chemistry technologies, e.g. DNA-encoded chemical library technologies as described in WO2009077173 and by R. E. Kleiner et al. in *Chemical Society Reviews* 40 5707-5717 (2011), L. Mannocci et al. in *Chemical Communications* 47, 12747-12753 (2011) and S. Brenner et al. in *Proceedings of the National Academy of Sciences of the USA* 89 5381-5383 (1992). An example of a screening method used to identify the best binding moiety for CAIX from a library of 111,100 small organic molecules is described in more detail below.

The binding moiety must tolerate attachment to the rest of the conjugate while maintaining binding affinity for its target. Suitably, the conjugate exhibits a binding affinity to its target (typically recombinant CAIX) such that the resulting complex has $K_D$ less than about 50 nM, more suitably less than about 30 nM, less than about 20 nM, less than 10 nM, less than 5 nM, less than 2 nM, or less than 1 nM.

Carbonic anhydrases are thought to have a catalytic mechanism which relies upon an active site which contains a coordinated zinc ion. Carbonic anhydrase inhibitors such as acetazolamide and methazolamide which have terminal sulfonamido groups are thought to act by forming an adduct between the zinc ion and the terminal nitrogen of the sulfonamide. Accordingly, the binding moieties in the conjugates according to the present invention suitably have a terminal sulfonamide (—SO$_2$NH$_2$), sulfamate (—OSO$_2$NH$_2$) or sulfamide NHSO$_2$NH$_2$) group. Most suitably, the terminal group is a sulphonamide group. Suitably, the terminal sulphonamide, sulfamate or sulfamide group is bonded to an aryl group, for example to form an arylsulfonamido group —ArSO$_2$NH$_2$.

The aryl group in these embodiments typically has a single ring or two fused rings. The aryl group may be carbocyclic or heterocyclic and may be substituted or unsubstituted.

Typically, small substituents are preferred such as Me, Et, OH, MeO, CF$_3$, F, CI, Br, I and CN. Whether or not the Ar group is substituted, two ring positions are taken up with the terminal sulfonamide group and the bond to the rest of the conjugate. These two ring positions may be at any point on the Ar ring.

Suitably, the aryl group is a thiadiazolyl group. In these embodiments, the ligand suitably comprises the following terminal moiety (T1):

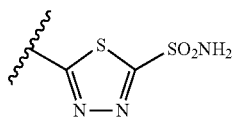 [SMILES: *c1nnc(S(N)(=O)=O)s1]

Suitably, the remainder of the conjugate is bonded to the thiadiazolyl group through an amide group, whereby the binding moiety (ligand) comprises the following terminal moiety having a structure similar to the terminal moiety of acetazolamide (T2):

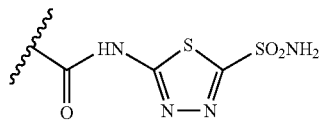 [SMILES: *C(=O)Nc1nnc(S(N)(=O)=O)s1]

In other embodiments, the above terminal moiety is modified by 4-N methylation of the thiadiazole group whereby the binding moiety (ligand) comprises the following terminal moiety having a structure similar to the terminal moiety of methazolamide (T3):

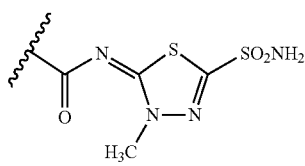 [SMILES: *C(=O)/N=c1/sc(S(N)(=O)=O)nn1C]

The binding moieties used in the present invention are not limited to sulfonamido derivatives. For example, coumarin ligands are also known to bind to CAIX. The skilled person using the techniques described herein and common general knowledge will be able to identify further suitable ligands for use as the binding moiety.

In embodiments, the binding moiety B may be a univalent binding moiety or a multivalent binding moiety, for example a bivalent binding moiety. The term "univalent binding moiety" refers to a binding moiety comprising a single ligand for binding to CAIX. The term "multivalent binding moiety" refers to a binding moiety having two or more binding ligands (which may be the same or different) for binding to the target entity. Suitably, the binding moiety is bivalent. The two or more binding ligands are separated by suitable spacer groups on the multivalent binding moieties. The use of multivalent binding moieties can provide enhanced binding of the binding moiety to the target.

Suitably, in these embodiments at least one of the two or more binding ligands comprises a terminal moiety

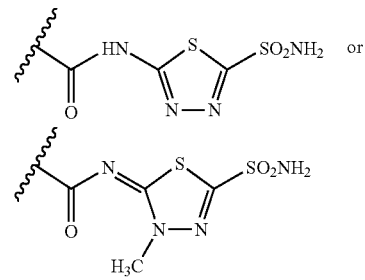

Figure 11:
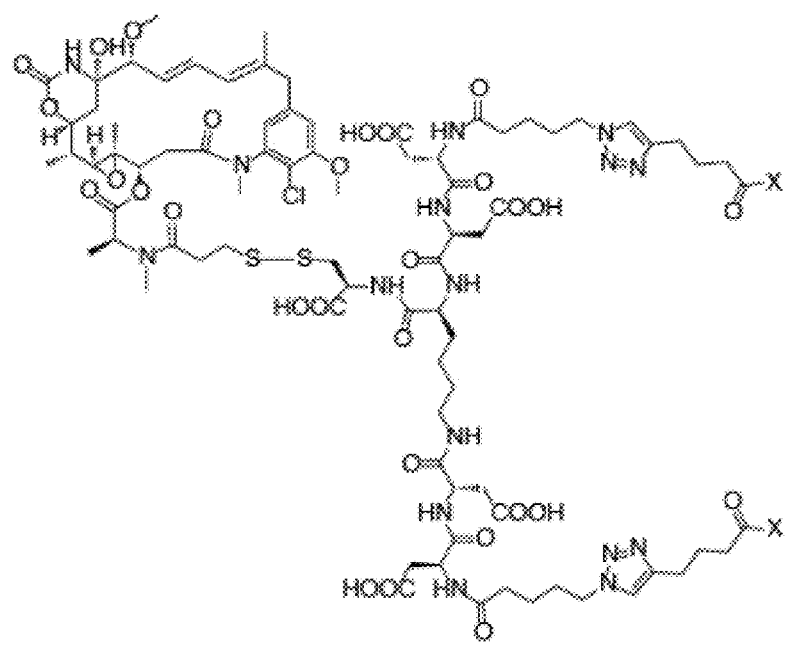
FIG. 11 shows the structures of a targeted bivalent drug conjugate B7 according to the present invention and an untargeted control B8.
Figure 11:
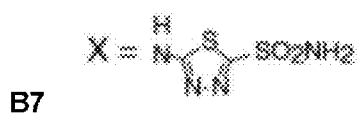
Figure 12:
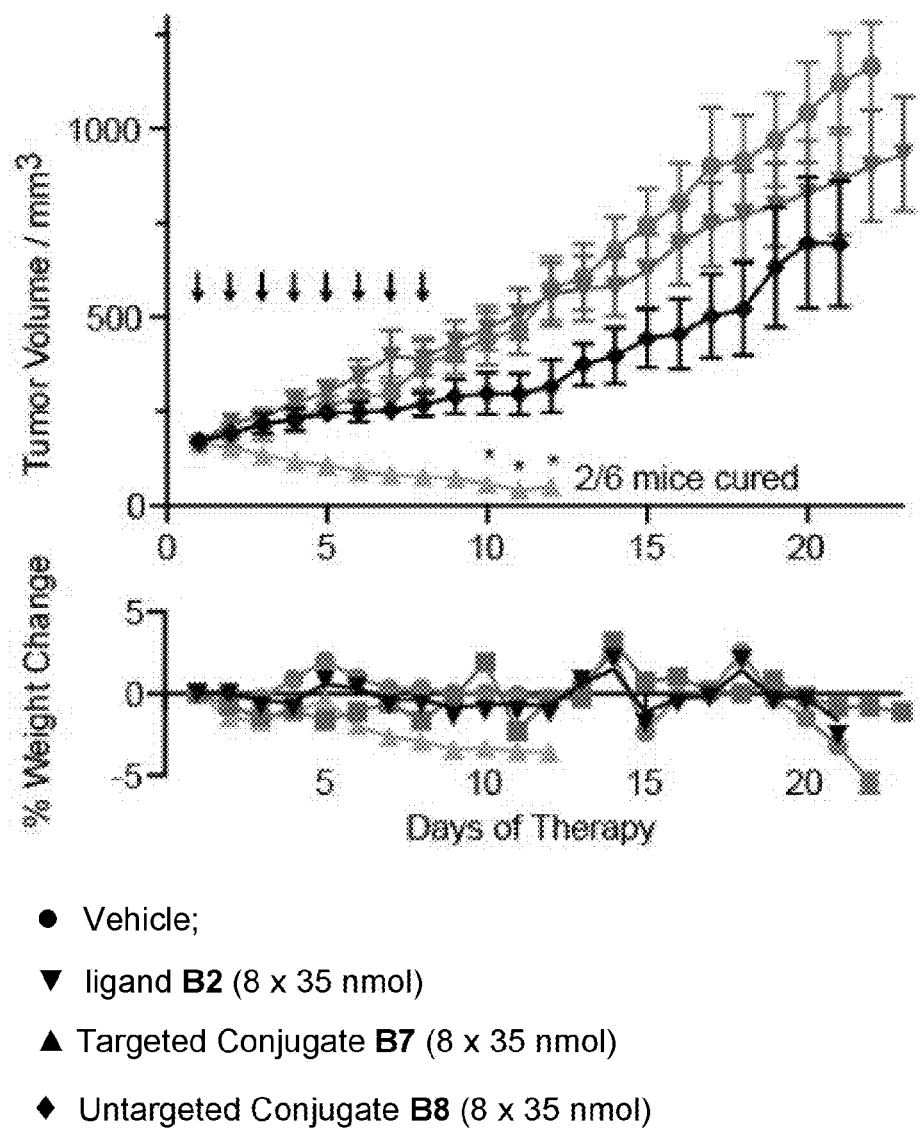
FIG. 12 shows tumor growth curves of animals injected with 8×35 nmol unconjugated ligand B2, bivalent drug conjugate B7, control conjugate B8 or vehicle as control. Data represent averages±standard errors.

In these embodiments binding moiety is suitably a bivalent binding moiety comprising a first binding ligand comprising a terminal moiety as defined above and a second binding ligand selected from the group consisting of ligands having a terminal moiety as defined above (an embodiment of this type having the formula B7 is shown in FIG. 11) and ligands having the terminal group

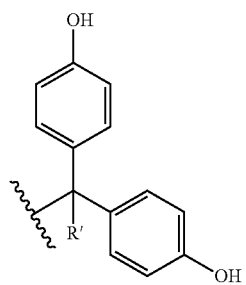

wherein R' is H or C1-C7 alkyl, C1-C7 alkenyl, or C1-C7 heteroalkyl, optionally substituted with one, two or three substituents, and preferably R' is methyl.

In embodiments of the latter type, the binding moiety suitably comprises or consists essentially of:

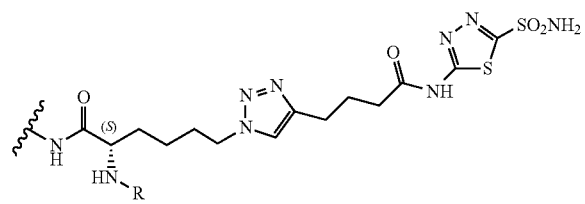

wherein R is selected from the group consisting of:

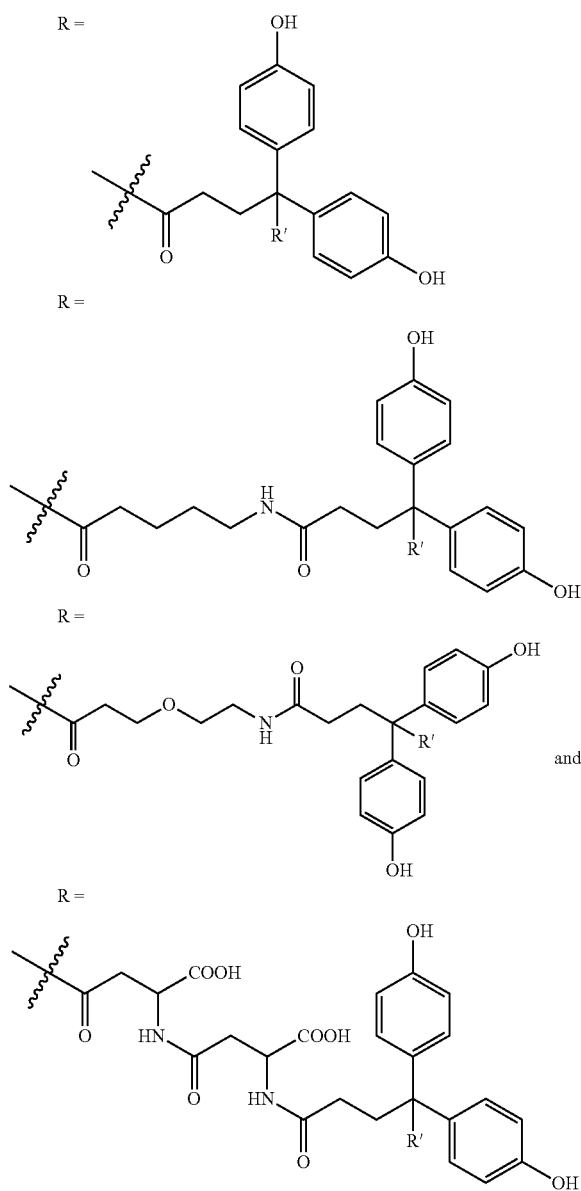

wherein R' is H or C1-C7 alkyl, C1-C7 alkenyl, or C1-C7 heteroalkyl, optionally substituted with one, two or three substituents, and preferably R' is methyl.

Suitably, the binding moiety has a binding affinity for CAIX such that the $K_D$ for binding of a ligand-fluorescein isothiocyanate conjugate wherein the dye conjugate has structure as shown in FIG. 1 to recombinant CAIX in vitro as determined by fluorescence polarization analysis as described herein is less than about 50 nM, preferably less than about 20 nM, more preferably less than about 15 nM.

Linker

The linker attaches the binding moiety to the drug moiety. The linker may be a bifunctional or a multifunctional moiety which can be used to link one or more drug moieties and binder moieties to form the SMDC. In embodiments, the conjugates of the present invention have a linker that links one drug moiety to one binding moiety (which may be univalent or multivalent).

The cytotoxic payloads should stably remain attached to the ligand while in circulation, but should be released when the conjugate reaches the site of disease.

Release mechanisms depend on a cleavable bond or other cleavable structure that is present in the linker. The cleavable structure may be similar to those specific to antibodies or other small molecules linked to cytotoxic payloads. Indeed the nature of the ligand is independent on that respect. Therefore we can envisage pH-dependent [Leamon, C. P. et al (2006) *Bioconjugate Chem.*, 17, 1226; Casi, G. et al (2012) *J. Am. Chem. Soc.*, 134, 5887], reductive [Bernardes, G. J. et al (2012) *Angew. Chem. Int. Ed. Engl.* 51. 941; Yang, J. et al (2006) *Proc. Natl. Acad. Sci. USA*, 103, 13872] and enzymatic release[Doronina S. O. et al (2008) *Bioconjugate Chem*, 19, 1960; Sutherland, M. S. K. (2006) *J. Biol. Chem*, 281, 10540]. In a specific setting, when functional groups are present on either the ligand or payloads (e.g. thiols, alcohols) which allow the creation of a cleavable bond, a linkerless connection can be established thus releasing intact payloads, which simplifies substantially pharmacokinetic analysis. A non-exhaustive list of moieties, which have cleavable bonds and which may be incorporated into linkers, is shown in the following table:

| Linker | Structure | Release mechanism |
|---|---|---|
| amide | (amide structure) | Proteolysis |
| ester | (ester structure, with $R^1$, $R^2$) | hydrolysis |
| carbamate | (carbamate structure, R = H, Me, NHR) | hydrolysis |
| hydrazone | (hydrazone structure, R) | hydrolysis |
| thiazolidine | (thiazolidine structure) | hydrolysis |
| disulfide | (disulfide structure, $R^1$, $R^2$, $R^3$, $R^4$) | reduction | wherein the substituents R and R″ in the above formulas may suitably be independently selected from H, halogen, substituted or unsubstituted (hetero)alkyl, (hetero)alkenyl, (hetero)alkynyl, (hetero)aryl, (hetero)arylalkyl, (hetero)cycloalkyl, (hetero)cycloalkylaryl, heterocyclylalkyl, a peptide, an oligosaccharide or a steroid group. Suitably R and R″ are independently selected from H, or C1-C7 alkyl or heteroalkyl. More suitably, R and R″ are independently selected from H, methyl or ethyl.

Suitably, the conjugate is stable to hydrolysis. That is to say, less than about 10% of the conjugate undergoes hydrolysis in PBS pH7.4 at 37° C. after 24 hours, as determined by HPLC.

Accordingly, the linker suitably comprises as its cleavable bond a disulfide linkage since these linkages are stable to hydrolysis, while giving suitable drug release kinetics at the target in vivo, and can provide traceless cleavage of drug moieties including a thiol group, such as DM1.

Suitably, the linker may be polar or charged in order to improve water solubility of the conjugate. For example, the linker may comprise from about 1 to about 20, suitably from about 2 to about 10, residues of one or more known water-soluble oligomers such as peptides, oligosaccharides, glycosaminoglycans, polyacrylic acid or salts thereof, polyethylene glycol, polyhydroxyethyl (meth) acrylates, polysulfonates, etc. Suitably, the linker may comprise a polar or charged peptide moiety comprising e.g. from 2 to 10 amino acid residues. Amino acids may refer to any natural or non-natural amino acid. The peptide linker suitably includes a free thiol group, preferably a C-terminal cysteine, for forming the said cleavable disulfide linkage with a thiol group on the drug moiety. A suitable peptide linker of this type is -Cys-Asp-Arg-Asp-.

Suitably, the linker is linked to the ligand through a 1,2,3-triazole ring formed by 1,3-cycloaddition of alkyne and azide. The drug and binding moieties are suitably linked to the 3 and 5 positions of the triazole ring. The triazole ring may optionally be substituted at the 4 position. The triazole is thought to improve binding of the ligand to CAIX. For example, the binding moieties identified above may be linked through a triazole group to form the following terminal moiety of the conjugate:

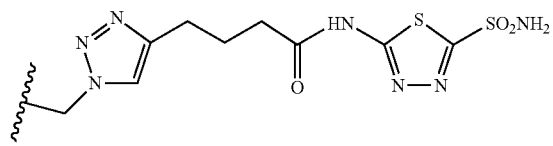 [SMILES: *Cn1cc(CCCC(=O)Nc2nnc(S(N)(=O)=O)s2)nn1]

More generally, the conjugates according to the present invention may have the following formula:

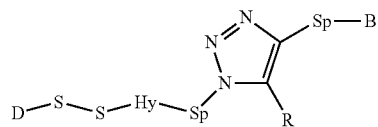

wherein: Hy is a hydrophilic moiety for improving the solubility of the conjugate, for example a hydrophilic oligomer as defined above such as a peptide group as defined above. S—S represents the cleavable disulfide bond between the drug moiety D and the linker. Suitably, the disulfide bond is formed between a —SH group on the linker, for example the —SH group of a cysteine residue (preferably terminal cysteine) of the peptide and a —SH group present in the active form of the drug D, for example the terminal —SH group of DM1. In this way, reductive cleavage of the disulfide bond in vivo results in traceless release of the drug in its active form.

Sp are spacer groups, which may be independently selected from optionally substituted straight or branched or cyclic C1-C6 alkylene or alkenylene, optionally including one or more carbonyl carbons or ether or thioether O or S atoms or amine N atoms in the chain. The first Sp group is suitably linked to the peptide residue by a terminal carbonyl forming an amide linkage with the terminal amino group of the peptide, as shown for example in the formula 9a in FIG. 2.

The triazole is optionally substituted at the 4 position by group R, whereby group R is selected from H or any of the substituent groups defined herein, or R is substituted or unsubstituted (hetero)alkyl, (hetero)alkenyl, (hetero)alkynyl, (hetero)aryl, (hetero)arylalkyl, (hetero)cycloalkyl, (hetero)cycloalkylaryl, heterocyclylalkyl, a peptide, an oligosaccharide or a steroid group. Suitably R is selected from H, halogen, halomethyl, or C1-C7 alkyl or heteroalkyl. More suitably, R is selected from H, methyl or ethyl, and most suitably R is H.

Alternatively or additionally to one or more of the linker elements described above, the linker in the conjugates of the present invention may comprise a cleavable peptide unit. The peptide unit sequence is specifically tailored so that it will be selectively enzymatically cleaved from the drug moiety by one or more proteases present on the cell surface or the extracellular regions of the target tissue. The amino acid residue chain length of the peptide unit suitably ranges from that of a single amino acid to about eight amino acid residues. Numerous specific cleavable peptide sequences suitable for use in the present invention can be designed and optimized in their selectivity for enzymatic cleavage by a particular tumor-associated enzyme e.g. a protease. Cleavable peptides for use in the present invention include those which are optimized toward the proteases MMP-1, 2 or 3, or cathepsin B, C or D. Especially suitable are peptides containing the sequence Val-Cit, which are cleavable by Cathepsin B. Cathepsin B is a ubiquitous cysteine protease. It is an intracellular enzyme, except in pathological conditions, such as metastatic tumors or rheumatoid arthritis. Therefore, non-internalizing conjugates of the present invention produced with cathepsin B-cleavable linkers are stable in circulation until activated in pathological tissue.

In these embodiment, the linker moiety suitably further comprises, adjacent to the peptide sequence, a "self-immolative" linker portion. The self-immolative linkers are also known as electronic cascade linkers. These linkers undergo elimination and fragmentation upon enzymatic cleavage of the peptide to release the drug in active, preferably free form. The conjugate is stable extracellularly in the absence of an enzyme capable of cleaving the linker. However, upon exposure to a suitable enzyme, the linker is cleaved initiating a spontaneous self-immolative reaction resulting in the cleavage of the bond covalently linking the self-immolative moiety to the drug, to thereby effect release of the drug in its underivatized or pharmacologically active form. In these embodiments, the self-immolative linker is coupled to the ligand moiety through an enzymatically cleavable peptide sequence that provides a substrate for an enzyme to cleave the amide bond to initiate the self-immolative reaction. Suitably, the drug moiety is connected to the self-immolative moiety of the linker via a chemically reactive functional group pending from the drug such as a primary or secondary amine, hydroxyl, sulfhydryl or carboxyl group.

Examples of self-immolative linkers are PABC or PAB (para-aminobenzyloxycarbonyl), attaching the drug moiety to the ligand in the conjugate (Carl et al (1981) J. Med. Chem. 24: 479-480; Chakravarty et al (1983) J. Med. Chem. 26: 638-644). The amide bond linking the carboxy terminus of a peptide unit and the para-aminobenzyl of PAB may be a substrate and cleavable by certain proteases. The aromatic amine becomes electron-donating and initiates an electronic cascade that leads to the expulsion of the leaving group, which releases the free drug after elimination of carbon dioxide (de Groot, et al (2001) Journal of Organic Chemistry 66 (26): 8815-8830). Further self-immolating linkers are described in WO2005/082023.

In these embodiments, the linker suitably further comprises a spacer unit linked to the binding moiety, for example via an amide, amine or thioether bond. The spacer unit is of a length that enables e.g. the cleavable peptide sequence to be contacted by the cleaving enzyme (e. g. cathepsin B) and suitably also the hydrolysis of the amide bond coupling the cleavable peptide to the self-immolative moiety X. Spacer units may for example comprise a divalent radical such as alkylene, arylene, a heteroarylene, repeating units of alkyloxy (e.g. polyethylenoxy, PEG, polymethyleneoxy) and alkylamino (e.g. polyethyleneamino), or diacid ester and amides including succinate, succinamide, diglycolate, malonate, and caproamide.

In yet other embodiments, the linker in the conjugates of the present invention may comprise a glucuronyl group that is cleavable by glucoronidase present on the cell surface or the extracellular region of the target tissue. It has been shown that lysosomal beta-glucuronidase is liberated extracellularly in high local concentrations in necrotic areas in human cancers, and that this provides a route to targeted chemotherapy (Bosslet, K. et al. *Cancer Res.* 58, 1195-1201 (1998)).

The number of drug and linker moieties per binding moiety, i.e. drug loading value, is suitably 1 to about 8, more suitably 1 or 2, and most suitably 1.

Drug

In one embodiment, the drug is a cytotoxic agent (other than a radioactive isotope) that inhibits or prevents the function of cells and/or causes destruction of cells. Examples of cytotoxic agents include chemotherapeutic agents, and toxins such as small molecule toxins or enzymatically active toxins of bacterial, fungal, plant or animal origin, including synthetic analogues and derivatives thereof. The cytotoxic agent may be selected from the group consisting of an auristatin, a DNA minor groove binding agent, a DNA minor groove alkylating agent, an enediyne, a lexitropsin, a duocarmycin, a taxane, a puromycin, a dolastatin, a maytansinoid and a vinca alkaloid or a combination of two or more thereof.

In one embodiment the drug is a chemotherapeutic agent selected from the group consisting of a topoisomerase inhibitor, an alkylating agent (eg. nitrogen mustards; ethylenimes; alkylsulfonates; triazenes; piperazines; and nitro sure as), an antimetabolite (eg mercaptopurine, thioguanine, 5-fluorouracil), an antibiotics (eg. anthracyclines, dactinomycin, bleomycin, adriamycin, mithramycin. dactinomycin) a mitotic disrupter (eg. plant alkaloids—such as vincristine and/or microtubule antagonists—such as paclitaxel), a DNA intercalating agent (eg carboplatin and/or cisplatin), a DNA synthesis inhibitor, a DNA-RNA transcription regulator, an enzyme inhibitor, agene regulator, a hormone response modifier, a hypoxia-selective cytotoxin (eg. tirapazamine), an epidermal growth factor inhibitor, an anti-vascular agent (eg. xanthenone 5,6-dimethylxanthenone-4-acetic acid), a radiation-activated prodrug (eg. nitroarylmethyl quaternary (NMQ) salts) or a bioreductive drug or a combination of two or more thereof.

The chemotherapeutic agent may selected from the group consisting of Erlotinib (TARCEVA®), Bortezomib (VELCADE®), Fulvestrant (FASLODEX®), Sutent (SU11248), Letrozole (FEMARA®), Imatinib mesylate (GLEEVEC®), PTK787/ZK 222584, Oxaliplatin (Eloxatin®.), 5-FU (5-fluorouracil), Leucovorin, Rapamycin (Sirolimus, RAPAMUNE®.), Lapatinib (GSK572016), Lonafarnib (SCH 66336), Sorafenib (BAY43-9006), and Gefitinib (IRESSA®.), AG1478, AG1571 (SU 5271; Sugen) or a combination of two or more thereof.

The chemotherapeutic agent may be an alkylating agent—such as thiotepa, CYTOXAN® and/or cyclosphosphamide; an alkyl sulfonate—such as busulfan, improsulfan and/or piposulfan; an aziridine—such as benzodopa, carboquone, meturedopa and/or uredopa; ethylenimines and/or methylamelamines—such as altretamine, triethylenemelamine, triethylenepbosphoramide, triethylenethiophosphoramide and/or trimethylomelamine; acetogenin—such as bullatacin and/or bullatacinone; camptothecin; bryostatin; callystatin; cryptophycins; dolastatin; duocarmycin; eleutherobin; pancratistatin; sarcodictyin; spongistatin; nitrogen mustards—such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide and/or uracil mustard; nitrosureas—such as carmustine, chlorozotocin, fotemustine, lomustine, nimustine, and/or ranimnustine; dynemicin; bisphosphonates—such as clodronate; an esperamicin; a neocarzinostatin chromophore; aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN®. doxorubicin—such as morpholino-doxorubicin, cyanomorpholino-doxorubicin, 2-pyrrolino-doxorubicin and/or deoxydoxorubicin, epirubicin, esorubicin, idarubicin, marcellomycin, mitomycins—such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites—such as methotrexate and 5-fluorouracil (5-FU); folic acid analogues—such as denopterin, methotrexate, pteropterin, trimetrexate; purine analogues—such as fludarabine, 6-mercaptopurine, thiamiprine, thioguanine; pyrimidine analogues—such as ancitabine, azacitidine, 6-azauridine, carmofur, cytarabine, dideoxyuridine, doxifluridine, enocitabine, floxuridine; androgens—such as calusterone, dromostanolone propionate, epitiostanol, mepitiostane, testolactone; anti-adrenals—such as aminoglutethimide, mitotane, trilostane; folic acid replenisher—such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; macrocyclic depsipeptides such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; razoxane; rhizoxin; sizofiran; spirogermanium; tenuazonic acid; triaziquone; 2,2',2"-trichlorotriethylamine; trichothecenes—such as verracurin A, roridin A and/or anguidine; urethan; vindesine; dacarbazine; mannomustine; mitobronitol; mitolactol; pipobroman; gacytosine; arabinoside; cyclophosphamide; thiotepa; taxoids—such as TAXOL®. paclitaxel, abraxane, and/or TAXOTERE®, doxetaxel; chloranbucil; GEMZAR®. gemcitabine; 6-thioguanine; mercaptopurine; methotrexate; platinum analogues—such as cisplatin and carboplatin; vinblastine; platinum; etoposide; ifosfamide; mitoxantrone; vincristine; NAVELBINE®, vinorelbine; novantrone; teniposide; edatrexate; daunomycin; aminopterin; xeloda; ibandronate; topoisomerase inhibitor RFS 2000; difluoromethylomithine (DMFO); retinoids—such as retinoic acid; capecitabine; and pharmaceutically acceptable salts, acids, derivatives or combinations of two or more of any of the above.

The drug may be a tubulin disruptor including but are not limited to: taxanes—such as paclitaxel and docetaxel, vinca alkaloids, discodermolide, epothilones A and B, desoxyepothilone, cryptophycins, curacin A, combretastatin A-4-phosphate, BMS 247550, BMS 184476, BMS 188791; LEP, RPR 109881A, EPO 906, TXD 258, ZD 6126, vinflunine, LU 103793, dolastatin 10, E7010, T138067 and T900607, colchicine, phenstatin, chalcones, indanocine, T138067, oncocidin, vincristine, vinblastine, vinorelbine, vinflunine, halichondrin B, isohomohalichondrin B, ER-86526, pironetin, spongistatin 1, spiket P, cryptophycin 1, LU103793 (cematodin or cemadotin), rhizoxin, sarcodictyin, eleutherobin, laulilamide, VP-16 and D-24851 and pharmaceutically acceptable salts, acids, derivatives or combinations of two or more of any of the above.

The drug may be a DNA intercalator including but are not limited to: acridines, actinomycins, anthracyclines, benzothiopyranoindazoles, pixantrone, crisnatol, brostallicin, CI-958, doxorubicin (adriamycin), actinomycin D, daunorubicin (daunomycin), bleomycin, idarubicin, mitoxantrone, cyclophosphamide, melphalan, mitomycin C, bizelesin, etoposide, mitoxantrone, SN-38, carboplatin, cis-platin, actinomycin D, amsacrine, DACA, pyrazoloacridine, irinotecan and topotecan and pharmaceutically acceptable salts, acids, derivatives or combinations of two or more of any of the above.

The drug may be an anti-hormonal agent that acts to regulate or inhibit hormone action on tumours—such as anti-estrogens and selective estrogen receptor modulators, including, but not limited to, tamoxifen, raloxifene, droloxifene, 4-hydroxytamoxifen, trioxifene, keoxifene, LY117018, onapristone, and/or fareston toremifene and pharmaceutically acceptable salts, acids, derivatives or combinations of two or more of any of the above. The drug may be an aromatase inhibitor that inhibits the enzyme aromatase, which regulates estrogen production in the adrenal glands—such as, for example, 4(5)-imidazoles, aminoglutethimide, megestrol acetate, AROMASIN®. exemestane, formestanie, fadrozole, RIVISOR®. vorozole, FEMARA®. letrozole, and ARIMIDEX® and/or anastrozole and pharmaceutically acceptable salts, acids, derivatives or combinations of two or more of any of the above.

The drug may be an anti-androgens—such as flutamide, nilutamide, bicalutamide, leuprolide, goserelin and/or troxacitabine and pharmaceutically acceptable salts, acids, derivatives or combinations of two or more of any of the above.

The drug may be a protein kinase inhibitor, a lipid kinase inhibitor or an anti-angiogenic agent.

In a preferred embodiment, the drug is a maytansinoid, in particular DM1, or a tubulin disruptor. Preferably, the drug in its active form comprises a thiol group, whereby a cleavable disulfide bond may be formed through the sulfur of the thiol group to bond the drug to the linker moiety in the conjugates of the invention.

The drug may be used in unmodified or modified form. Combinations of drugs in which some are unmodified and some are modified may be used. For example, the drug may be chemically modified. One form of chemical modification is the derivatisation of a carbonyl group—such as an aldehyde.

According to one embodiment, the drug is modified to allow the incorporation of the linker. For example, a drug comprising a hydroxyl group may be converted to the corresponding 2-ethanethiol carbonate or 2-ethanethiol carbamate thereby introducing thiol groups for disulphide linkage as discussed above.

The drug can also be a cytokine (e.g., an interleukin, a member of the TNF superfamily, or an interferon.

SMDCs

The drug moiety of the SMDC may not be cleaved from the linker until the SMDC binds to its target cell or tissue.

In one embodiment, the SMDCs described herein are not substantially internalized into a cell. Such a "non-internalizing" drug conjugate has the property of reacting in physiological conditions (at 37° C. and pH 7) in vivo or in vitro, with binding partners on the cell surface (e.g. cell surface antigens) or in the extracellular matrix without being internalized in the cells by a process of active endocytosis (such as receptor/antigen mediated endocytosis). It is possible that some of the non-internalizing specific binding moiety could be taken up intracellularly by fluid phase endocytosis. However, the amount of fluid phase endocytosis will depend linearly on the extracellular binding moiety concentration and temperature and can therefore be distinguished from mediated endocytosis in order to distinguish non-internalizing binding moieties and conjugates according to the present invention.

The use of non-internalizing compounds provides advantages. For example, internalization efficiency is difficult to measure in vivo, thus remaining a "black box" for drug development. Moreover, it is difficult to ensure that all diseased cells are targeted by internalizing compounds, especially those cells which are further away from blood vessels. In contrast, the cleavage of the SMDCs of the present invention in the extracellular space allows the drug to diffuse to neighboring cells and kill them. It is also envisaged that dying cells will liberate cleavage agents (e.g. cysteine or glutathione) that will activate more of the drug from the SMDC resulting in self-amplification of the toxic effects.

Accordingly, the linker that is used in the SMDC should be stable enough compared to the rate of blood clearance of the compound but labile enough compared to the residence time of the compound at the target site. From these considerations, a half-life of the conjugate in the region of about 1 hour to about 50 hours—such as about 10 to about 50 hours or about 20 to about 50 hours may be acceptable, especially when vascular tissues or cells are targeted. The half-life herein refers to the half-life of the conjugate in mouse serum in vitro at 37° C. as determined by HPLC. Advantageously therefore, the SMDCs described herein may have improved lability and/or stability in vitro and/or in vivo which makes them particularly suitable for controlled drug release, especially at vascular tissues, cells and tumours.

Suitably, the SMDC shows a high affinity for CAIX expressing tumors when administered systemically. Suitably, a tumor-to-blood concentration ratio of at least about 5:1, for example at least about 10:1 is achieved 1 hour after injection of 3 nm of the conjugate into nude mice having subcutaneous SKRC52 tumors.

Suitably, the SMDC inhibits, retards or prevents growth of a tumour when administered in a therapeutically effective amount.

Treatment

The SMDCs described herein may be used to treat disease. The treatment may be therapeutic and/or prophylactic treatment, with the aim being to prevent, reduce or stop an undesired physiological change or disorder. The treatment may prolong survival as compared to expected survival if not receiving treatment.

The disease that is treated by the SMDC may be any disease that might benefit from treatment. This includes chronic and acute disorders or diseases including those pathological conditions which predispose to the disorder. One particular disease that is applicable to treatment by the present invention is neoplastic disease such as cancer that can be treated via the targeted delivery of cytotoxic agents. Non-limiting examples of cancers that may be treated include benign and malignant tumours; leukemia and lymphoid malignancies, including breast, ovarian, stomach, endometrial, salivary gland, lung, kidney, colon, thyroid, pancreatic, prostate or bladder cancer. The disease may be a neuronal, glial, astrocytal, hypothalamic or other glandular, macrophagal, epithelial, stromal and blastocoelic disease; or inflammatory, angiogenic or an immunologic disease. An exemplary disease is a solid, malignant tumour.

The term "cancer" and "cancerous" is used in its broadest sense as meaning the physiological condition in mammals that is typically characterized by unregulated cell growth. A tumour comprises one or more cancerous cells. Examples of cancer include, but are not limited to, carcinoma, lymphoma, blastoma, sarcoma, and leukemia or lymphoid malignancies. Further examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, gastrointestinal stromal tumour (GIST), pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. Based on established evidence of expression of CAIX, it is expected that the present invention will be suitable in particular for the treatment of glioblastoma, lung cancer, head and neck cancer, cervical cancer, colorectal cancer, breast cancer, and, especially, renal cell carcinoma.

For the prevention or treatment of disease, the dosage of a SMDC will depend on an array of different factors—such as the type of disease to be treated, the severity and course of the disease, whether the molecule is administered for preventive or therapeutic purposes, previous therapy, the patient's clinical history and response to the protein, and the discretion of the attending physician.

The molecule may be administered to the patient at one time or over a series of treatments. Depending on the type and severity of the disease, between about 1 ug/kg to 15 mg/kg of drug may be used as an initial candidate dosage for administration to the patient, whether, for example, by one or more separate administrations, or by continuous infusion. A typical daily dosage might range from about 1 ug/kg to 100 mg/kg or more. An exemplary dosage of drug may be in the range of about 0.1 to about 10 mg/kg of patient weight.

When treating cancer, the therapeutically effect that is observed may be a reduction in the number of cancer cells; a reduction in tumour size; inhibition or retardation of cancer cell infiltration into peripheral organs; inhibition of tumour growth; and/or relief of one or more of the symptoms associated with the cancer.

In animal models, efficacy may be assessed by physical measurements of the tumour during the treatment, and/or by determining partial and complete remission of the cancer. For cancer therapy, efficacy can, for example, be measured by assessing the time to disease progression (TTP) and/or determining the response rate (RR).

Pharmaceutical Compositions

The SMDCs described herein may be in the form of pharmaceutical compositions which may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition may be formulated to be administered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be administered by a number of routes.

If the agent is to be administered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions may be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or the pharmaceutical compositions can be injected parenterally, for example, intravenously, intramuscularly or subcutaneously. For parenteral administration, the compositions may be best used in the form of a sterile aqueous solution which may contain other substances, for example, enough salts or monosaccharides to make the solution isotonic with blood. For buccal or sublingual administration the compositions may be administered in the form of tablets or lozenges which can be formulated in a conventional manner.

The SMDC may be administered in the form of a pharmaceutically acceptable or active salt. Pharmaceutically-acceptable salts are well known to those skilled in the art, and for example, include those mentioned by Berge et al, in J.Pharm.Sci., 66, 1-19 (1977). Salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The routes for administration (delivery) may include, but are not limited to, one or more of oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, vaginal, epidural, sublingual.

Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

The formulations may be packaged in unit-dose or multi-dose containers, for example sealed ampoules and vials, and may be stored in a freeze-dried (lyophilized) condition requiring only the addition of the sterile liquid carrier, for example water, for administration. Extemporaneous injection solutions and suspensions are prepared from sterile powders, granules and tablets of the kind previously described. Exemplary unit dosage formulations contain a daily dose or unit daily sub-dose, or an appropriate fraction thereof, of the active ingredient.

Combination Therapy

A SMDC may be combined in a pharmaceutical combination formulation, or dosing regimen as combination therapy, with a second compound having therapeutic properties. The second compound of the pharmaceutical combination formulation or dosing regimen preferably has complementary activities to the SMDC of the combination such that they do not adversely affect each other.

The second compound may be selected from the group consisting of a protein, antibody, antigen-binding fragment thereof, a drug, a toxin, an enzyme, a nuclease, a hormone, an immunomodulator, an antisense oligonucleotide, an siRNA, a boron compound, a photoactive agent, a dye and a radioisotope or a combination of two or more thereof.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein there is a time period while both (or all) active agents simultaneously exert their biological activities.

As noted above, the SMDCs of the invention achieve optimal tumor:organ ratios some time after administration, when the SMDC has had the opportunity to localize at the site of the disease, while clearing from blood and healthy organs. Thus, it would be desirable to provide controlled release of the toxic payload from the SMDC at a controlled time interval after administration. This can be achieved by administering an effective amount of a cleavage agent for cleaving the linker L at a later time point following SMDC administration, in order to trigger an efficient release of the drug payload when suitable tumor:blood and tumor:organ ratios have been achieved. The time interval between administration of the SMDC and administration of the cleavage agent may, for example, be from about 10 minutes to about 12 hours, suitably from about 30 minutes to about 6 hours, more suitably from about 1 hour to about 2 hours.

Thus, the combination products according to the invention include a product comprising a compound of Formula (I) as defined above and a cleavage agent for cleaving the cleavable linker L, as a combined preparation for sequential administration in the treatment of cancer.

Suitably, either: (a) linker L comprises a disulphide bond and the cleavage agent comprises a reducing agent such as cysteine, N-acetylcysteine, ordithiothreitol; or (b) linker L comprises an amide linkage and the cleavage agent comprises a hydrolase such as a protease; or (c) linker L comprises an ester linkage and the cleavage agent comprises a hydrolase such as an esterase.

The cleavage agent is administered in an amount effective to achieve the desired release of the toxic payload from the SMDC in vivo. For example, between about 1 ug/kg to 15 mg/kg of drug may be used as an initial candidate dosage for administration to the patient, whether, for example, by one or more separate administrations, or by continuous infusion. An exemplary dosage of cleavage agent may be in the range of about 0.1 to about 10 mg/kg of patient weight.

The above products for combined administration and methods of treatment by sequential administration of drug conjugate and cleavage agent are also applicable to antibody-drug conjugates as to conjugates in which the ligand is a low molecular weight entity. Thus, combination products and methods in which the SMDC is an antibody-drug conjugate (ADC) comprising as the binding moiety an antibody or antibody fragment that binds selectively to CAIX are encompassed within these aspects of the invention.

Substituents

The chemical compounds described herein may comprises substituents. In particular, the compounds may contain one or more hydroxy, alkyl especially lower ($C_1$-$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$-$C_6$) alkoxy, e.g. methoxy, ethoxy, propoxy etc., alkinyl, e.g. ethinyl, or halogen (e.g. fluoro) substituents.

Chemical Synthesis

The compounds described herein may be prepared by chemical synthesis techniques.

It will be apparent to those skilled in the art that sensitive functional groups may need to be protected and deprotected during synthesis of a compound. This may be achieved by conventional techniques, for example as described in "Protective Groups in Organic Synthesis" by T W Greene and P G M Wuts, John Wiley and Sons Inc. (1991), and by P. J. Kocienski, in "Protecting Groups", Georg Thieme Verlag (1994).

It is possible during some of the reactions that any stereocentres present could, under certain conditions, be epimerised, for example if a base is used in a reaction with a substrate having an optical centre comprising a base-sensitive group. It should be possible to circumvent potential problems such as this by choice of reaction sequence, conditions, reagents, protection/deprotection regimes, etc. as is well-known in the art.

The compounds and salts of the invention may be separated and purified by conventional methods.

General Techniques

The practice of the present invention employs, unless otherwise indicated, conventional methods of chemistry, biochemistry, molecular biology, cell biology, genetics, immunology and pharmacology, known to those of skill of the art. Such techniques are explained fully in the literature. See, e. g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M., and Blackwell, C. C., eds. (1986) Handbook of Experimental Immunology, Vols. I-IV, Blackwell Scientific Publications; Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press; Newton, C. R., and Graham, A., eds. (1997) PCR (Introduction to Biotechniques Series), 2nd ed., Springer Verlag.

The invention will now be further described by way of Examples, which are meant to serve to assist one of ordinary skill in the art in carrying out the invention and are not intended in any way to limit the scope of the invention.

EXAMPLES (A) Monovalent Binding Moieties

Figure 2:
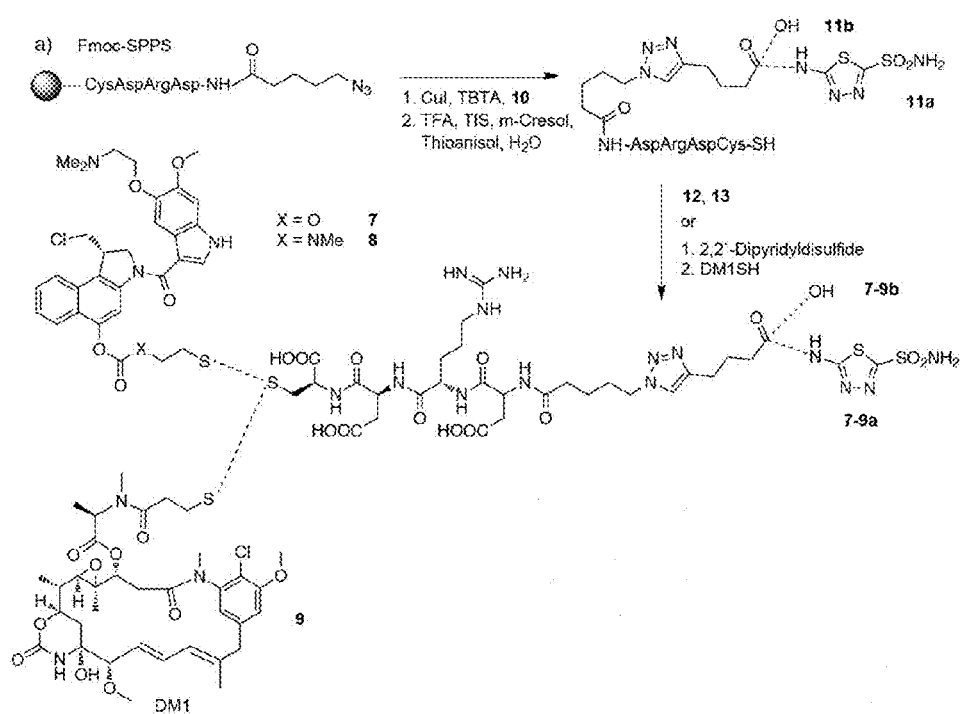
FIG. 2 shows structures and synthesis of small molecule drug conjugates according to the present invention.

Reference compounds having formulas 1a-6c shown in FIG. 1 were prepared for studies of binding by ligand-linker-dye conjugates to CAIX in vitro and in vivo. Conjugates according to the present invention having formulas 7a, 8a and 9a as shown in FIG. 2 were prepared according to the scheme in FIG. 2 and studied in vitro and in vivo as described below. Reference conjugates 7b, 8b and 9b as shown in FIG. 2 having the drug and linker moieties but no binding moiety were also prepared according to the scheme shown in FIG. 2 for comparative studies.

General Chemical Procedures

Proton ($^1$H) nuclear magnetic resonance (NMR) spectra were recorded on a Bruker AV400 (400 MHz) or a Bruker AVIII500 (500 MHz) spectrometer. Carbon ($^{13}$C) NMR spectra were recorded on a Bruker AV400 (100 MHz) spectrometer or on a Bruker AVIII500 (125 MHz) spectrometer. Chemical shifts are given in ppm using residual solvent as the internal standard. Coupling constants (J) are reported in Hz with the following abbreviations used to indicate splitting: s=singlet, d=doublet, t=triplet, q=quartet, m=multiplet. High-resolution mass spectrometry (HRMS) spectra were recorded on a Bruker Daltronics maXis ESI-QTOF mass spectrometer. Calculated and exact m/z values are reported in Daltons.

Analytical and preparative reversed-phase high-pressure liquid chromatography (RP-HPLC) were performed on an Waters Alliance HT RP-HPLC with PDA UV detector, using a Synergi 4 µm, Polar-RP 150×10 mm column at a flow rate of 4 mL min$^{-1}$ with linear gradients of solvents A and B (A=Millipore water with 0.1% trifluoroacetic acid [TFA], B=MeCN).

Anhydrous solvents for reactions were purchased from Acros or Fluka. Peptide grade dimethyl formamide (DMF) for solid phase synthesis was bought from ABCR. All other solvents were used as supplied by Fisher Chemicals, Merck or Aldrich in HPLC or analytical grade. IRDye750 N-hydroxysuccinimidyl (NHS) ester was purchased from Licor, Alexa546 NHS ester from Invitrogen, N-Boc protected (S)-1-chloromethyl-6-hydroxy-1,2-dihydrobeno[e]indole (seco CBI) from Anthem Bioscience. DM1 was purchased from Concortis Biosystems. All other reagents were purchased from Aldrich, Acros, ABCR or TCI and used as supplied. All reactions using anhydrous conditions were performed using oven-dried glassware under an atmosphere of argon. Brine refers to a saturated solution of sodium chloride. Silica for flash column chromatography was purchased from Sigma.

Preparation of Previously Described Compounds

Compounds 6c and 11-17 were prepared according to previously described methods as summarized in the following table.

| Structure | Number | Reference |
|---|---|---|
| 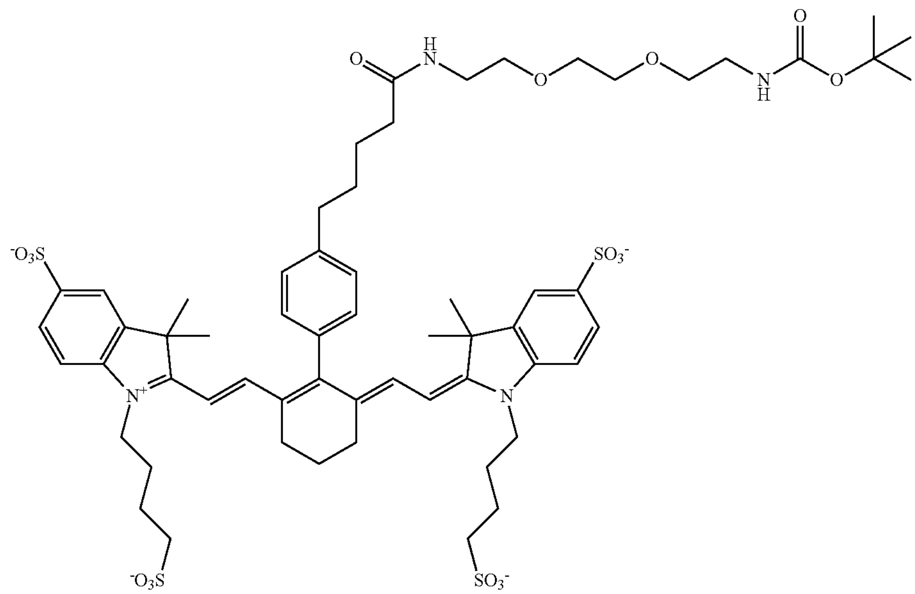 | 6c | [6] |
| 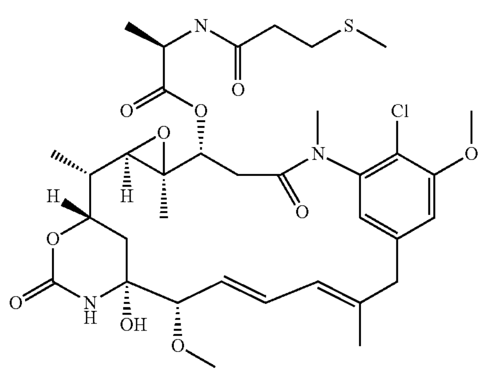 [SMILES: COc1cc2cc(c1Cl)N(C)C(=O)C[C@@H](OC(=O)[C@@H](C)NC(=O)CCSC)[C@]1(C)O[C@@H]1[C@@H](C)[C@@H]1C[C@](O)(NC(=O)O1)[C@@H](OC)/C=C/C=C(\C)C2] | 15 | [7] |
| DM1-SMe | | |
| 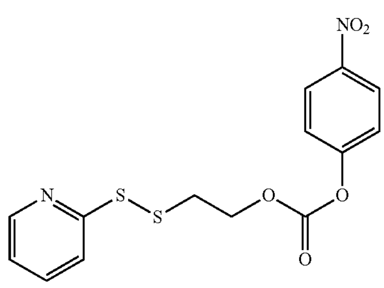 [SMILES: O=C(OCCSSc1ccccn1)Oc1ccc([N+](=O)[O-])cc1] | 16 | [8] |
| 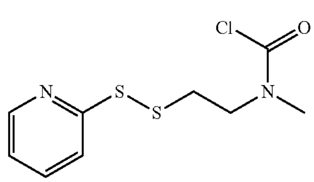 | 17 | [9] |

| Structure | Number | Reference |
|---|---|---|
| (HO-CO-indole-OMe-O-CH2CH2-N(CH3)2) | 18 | [10] |
| BocHN-CH2CH2-O-CH2CH2-O-CH2CH2-NH2 | 19 | [11] |
| HOOC-CH(N3)-CH(CH3)2 | 20 | [12] |
| H2NO2S-C6H4-NH-(triazine-Cl2) | 21 | [13] |
| PhNH-CH2CH2-COOH | 22 | [14] |
| H2N-(1,3,4-thiadiazole)-SO2NH2 | 23 | [15] |
| HO-CO-(CH2)3-N3 | 24 | [16] |
Chemical Synthesis of New Compounds
N1-(2-(2-(2-aminoethoxy)ethoxy)ethyl)-N4-(5-sulfamoyl-1,3,4-thiadiazol-2-yl)succinamide fluorescein conjugate—1a
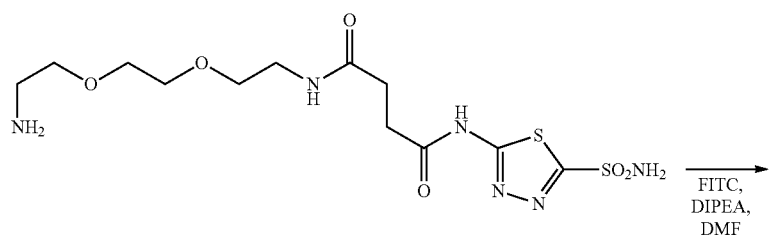
FITC, DIPEA, DMF

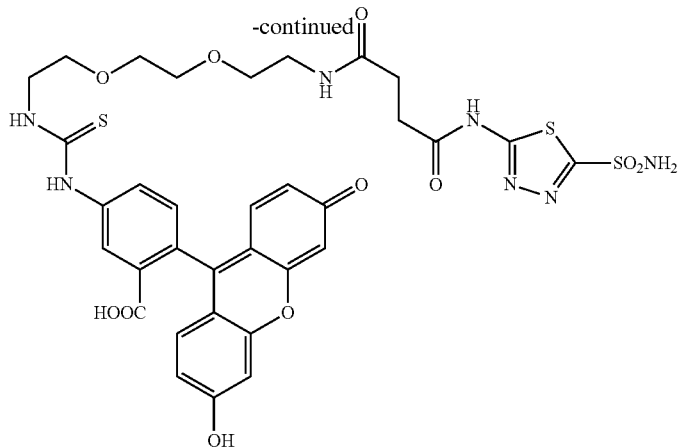

25 (7.0 mg, 17 µmol) and fluoresceinisothiocyanate (FITC, 6.7 mg, 17 µmol) were dissolved in dimethylformamide (DMF, 1 mL) and diisopropylethylamine (DIPEA, 8 µL, 48 µmol) was added. The reaction was stirred for 2 h at room temperature, diluted with MeOH (1 mL) and purified over reversed-phase HPLC (80% A/20% B to 20% A/80% B over 20 min). Fractions containing the desired product by mass spectrometry (MS) were pooled and lyophilized to give the product as a yellow powder (12 mg, 16 µmol, 95%).

$^1$H-NMR (400 MHz, MeOD-$d_4$) δ [ppm]=8.31 (s, 1H), 7.91 (d, J=7.5 Hz, 1H), 7.25 (d, J=7.5 Hz, 1H), 7.02 (d, J=8.5 Hz, 2H), 6.92 (s, 2H), 6.79 (d, J=8.5 Hz, 2H), 3.85 (br, 2H), 3.75 (t, J=4.8 Hz, 2H), 3.72-3.65 (m, 4H), 3.58 (t, J=5.4 Hz, 2H), 3.38 (t, J=5.4 Hz, 2H), 2.85 (t, J=6.8 Hz, 2H), 2.66 (t, J=6.8 Hz, 2H); $^{13}$C-NMR (125 MHz, DMSO-$d_6$) δ [ppm]=180.8, 172.3 172.2, 171.3, 171.2, 169.0, 164.6, 161.4, 159.9, 152.4, 147.6, 141.8, 129.5, 127.0, 124.5, 116.7, 113.0, 110.3, 102.7, 70.1, 69.6, 68.9, 44.1, 39.0, 30.7, 29.8, signals from PEG linker predicted to overlap; HRMS: (m/z) [M+H]$^+$ calcd. for $C_{33}H_{34}N_7O_{11}S_3$, 800.1473. found 800.1470.

N1-(2-(2-(2-aminoethoxy)ethoxy)ethyl)-N4-(5-sulfamoyl-1,3,4-thiadiazol-2-yl)succinamide Alexa546 conjugate—1b

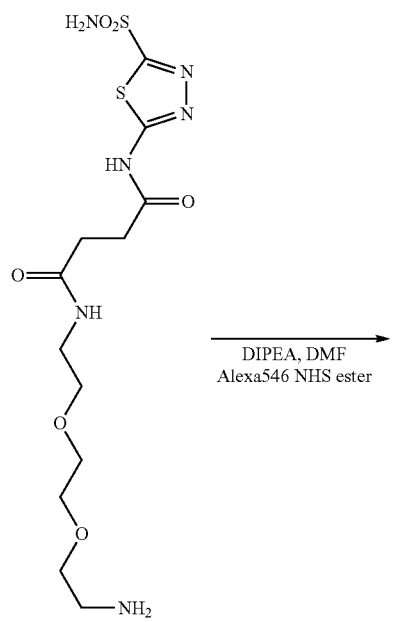

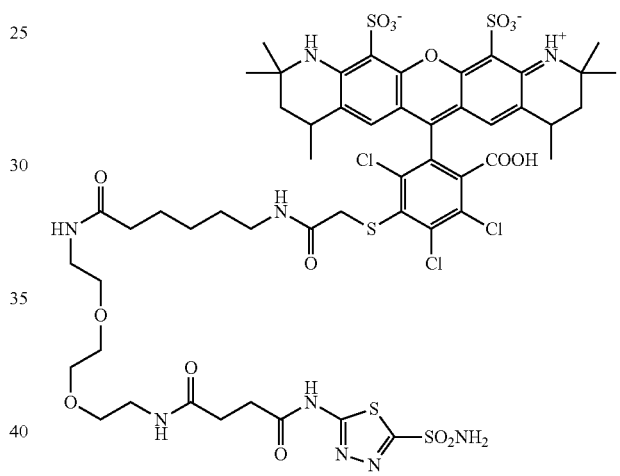

To 25 (212 µg, 517 nmol) in DMF (2.1 µL) was added Alexa546 NHS ester (100 µg, 86 nmol). DIPEA (2 µL, 12 µmol) and DMF (50 µL) were added and the mixture stirred for 2 h at room temperature. The reaction was diluted with MeOH (50 µL) and purified over reversed-phase HPLC (95% A/5% B to 20% A/80% B over 20 min). Fractions containing the product as identified through its characteristic UV/VIS spectrum ($\lambda_{max}$=550 nm) were pooled, lyophilized and dissolved in 100 µL PBS pH 7.4 to give a dark purple solution. Its concentration and the reaction yield were determined by measuring the absorbance at 556 nm ($\epsilon_{556}$=112,000 M$^{-1}$ cm$^{-1}$) of stock samples diluted 1:100 into PBS pH 7.4 (443 µM, 44 nmol, 51%).

HRMS: (m/z) [M+H]$^+$ calcd. for $C_{52}H_{65}Cl_3N_9O_{17}S_5$, 1352.2162. found 1352.2157.

N1-(2-(2-(2-aminoethoxy)ethoxy)ethyl)-N4-(5-sulfamoyl-1,3,4-thiadiazol-2-yl)succinamide IRDye750 conjugate—1c

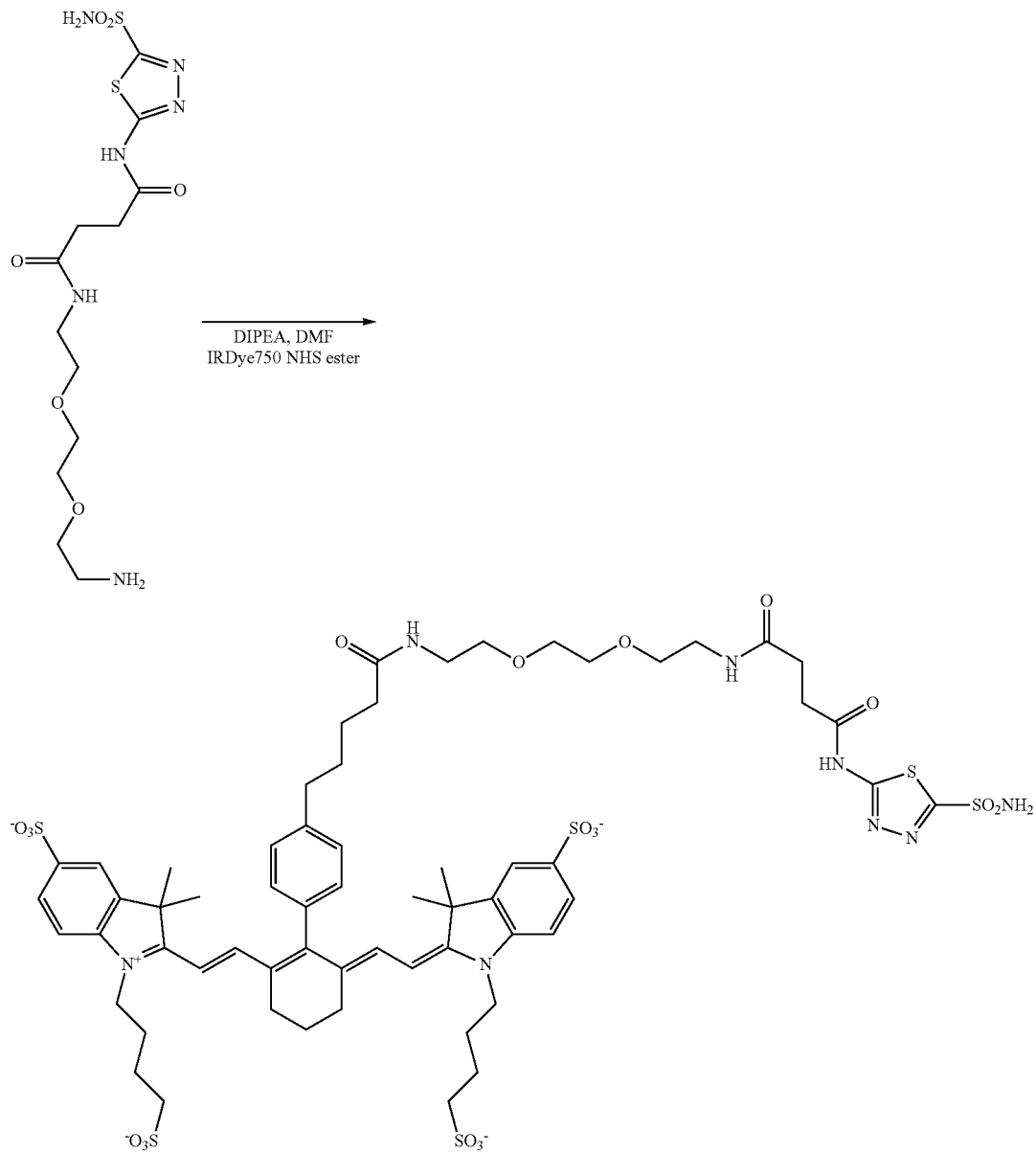

To 25 (131 µg, 320 nmol) in DMSO (13 µL) was added IRDye750 NHS ester (194 µg, 163 nnmol) in DMSO (25 µL) followed by DMF (100 µL) and DIPEA (10 µL, 60 µmol). The solution was stirred for 6 h at room temperature and then directly purified over reversed-phase HPLC (95% A/5% B to 40% A/60% B over 30 min). Fractions containing dye conjugate were identified through their characteristic UV/VIS spectrum ($\lambda_{max}$=750 nm), pooled, lyophilized and dissolved in dimethylsulfoxide (DMSO, 100 µL) to give a dark green stock solution. Its concentration and the reaction yield were determined by measuring the absorbance at 750 nm ($\epsilon_{750}$=260,000 M$^{-1}$ cm$^{-1}$) of stock samples diluted 1:200 into PBS pH 7.4 (1.02 mM, 102 nmol, 63%).

HRMS: (m/z) [M+Na]$^{2-}$ cacld. for $C_{61}H_{77}N_8NaO_{19}S_6$, 720.1769. found 720.1760.

(S)—N-(2-(2-(2-aminoethoxy)ethoxy)ethyl)-3-methyl-2-(4-(4-sulfamoylphenyl)-1H-1,2,3-triazol-1-yl)butanamide fluorescein conjugate—2a

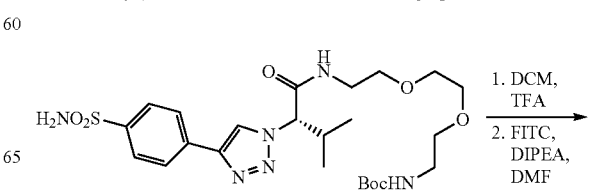

-continued

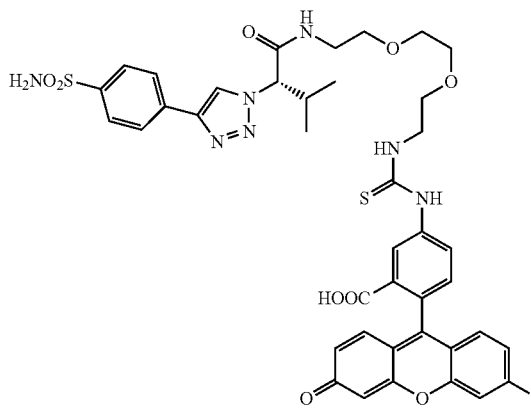

26 (20 mg, 36 µmol) was dissolved in a mixture of dichloromethane (DCM, 0.5 mL) and TFA (0.5 mL) and stirred for 1 h at room temperature. The solvents were removed under reduced pressure and the residue dissolved in DMF (0.5 mL). DIPEA (31 µL, 187 µmol) was added followed by FITC (14 mg, 36 µmol). The reaction was stirred for 2 h at room temperature, diluted with MeOH (0.5 mL) and purified over reversed-phase HPLC (80% A/20% B to 20% A/80% B over 20 min). Fractions containing product by MS were pooled end lyophilized to give the product as a bright yellow powder (18 mg, 23 µmol, 64%).

$^1$H-NMR (500 MHz, DMSO-d$_6$) δ [ppm]=10.07 (br s, 1H), 8.86 (s, 1H), 8.75 (t, J=5.4 Hz, 1H), 8.28 (s, 1H), 8.18 (s, 1H), 8.10 (d, J=6.7 Hz, 2H), 7.39 (d, J=6.7 Hz, 2H), 7.74 (d, J=7.9 Hz, 1H), 7.18 (d, J=8.3 Hz, 1H), 6.66-6.54 (m, 6H), 5.07 (d, J=10.3 Hz, 1H), 3.68 (br s, 2H), 3.60-3.56 (m, 6H), 3.48 (t, J=5.6 Hz, 2H), 3.41-3.19 (m, 2H), 2.49-2.45 (m, 1H), 1.01 (d, J=6.6 Hz, 3H), 0.73 (d, J=6.6 Hz, 3H); $^{13}$C-NMR (125 MHz, DMSO-d$_6$) δ [ppm]=181.1, 169.0, 167.9, 160.2, 159.1, 158.8, 152.5, 147.3, 145.7, 143.6, 141.8, 134.3, 129.5, 126.8, 125.8, 124.6, 121.9, 117.0, 114.5, 113.2, 110.3, 102.7, 70.1, 70, 69.6, 69.2, 68.9, 44.2, 31.6, 19.2, 19.1; HRMS: (m/z) [M+H]$^+$ calcd. for $C_{40}H_{42}N_7O_{10}S_2$, 844.2429. found 844.2430.

(S)—N-(2-(2-(2-aminoethoxy)ethoxy)ethyl)-3-methyl-2-(4-(4-sulfamoylphenyl)-1H-1,2,3-triazol-1-yl)butanamide IRDye750 conjugate—2c

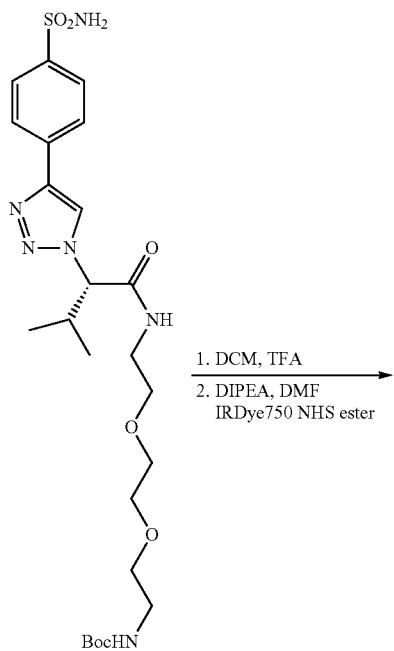

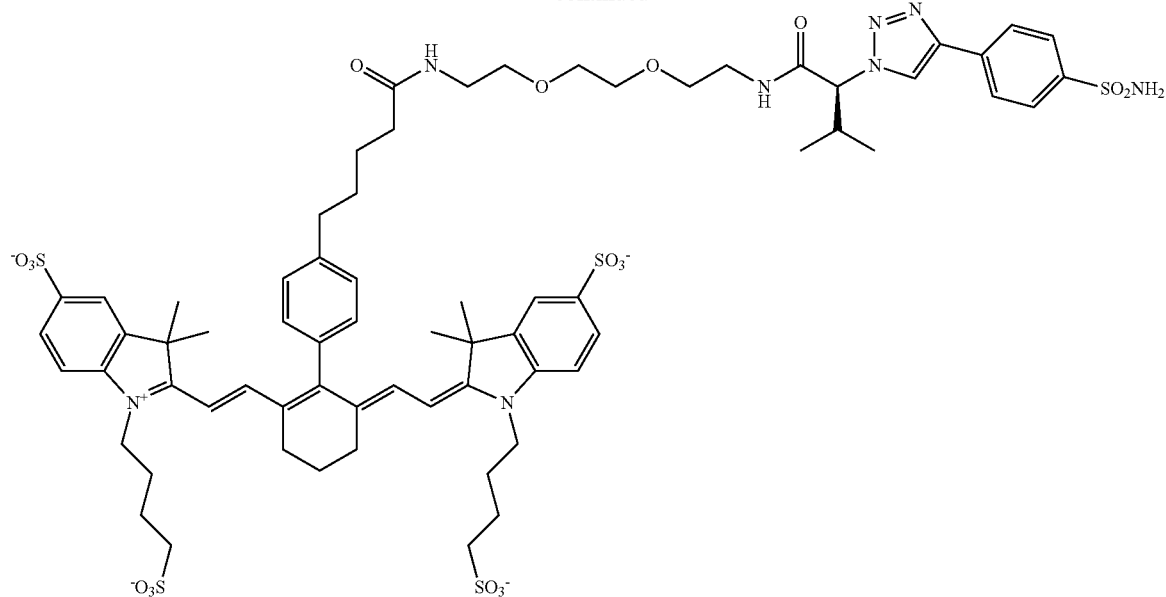

26 (178 μg, 321 nmol) in DMSO (34 μL) was added to a mixture of TFA (100 μL) and DCM (100 μL). The reaction was stirred for 1 h at room temperature and the solvent removed under reduced pressure. To the residual solution was added IRDye750 NHS ester (194 μg, 163 nnmol) in DMSO (25 μL) followed by DMF (100 μL) and DIPEA (10 μL, 60 μmol). The solution was stirred for 6 h at room temperature and then directly purified over reversed-phase HPLC (95% A/5% B to 40% A/60% B over 30 min). Fractions containing dye conjugate were identified through their characteristic UV/VIS spectrum ($\lambda_{max}$=750 nm), pooled, lyophilized and dissolved in DMSO (100 μL) to give a dark green stock solution. Its concentration and the reaction yield were determined by measuring the absorbance at 750 nm ($\epsilon_{750}$=260,000 $M^{-1}$ $cm^{-1}$) of stock samples diluted 1:200 into PBS pH 7.4 (662 μM, 66 nmol, 40%).

HRMS: (m/z) $[M+Na]^{2-}$ calcd. for $C_{68}H_{85}N_8NaO_{18}S_5$, 742.2247. found 742.2233.

4-((4-((2-(2-(2-aminoethoxy)ethoxy)ethyl)amino)-6-chloro-1,3,5-triazin-2-yl)amino)benzenesulfonamide fluorescein conjugate—3a

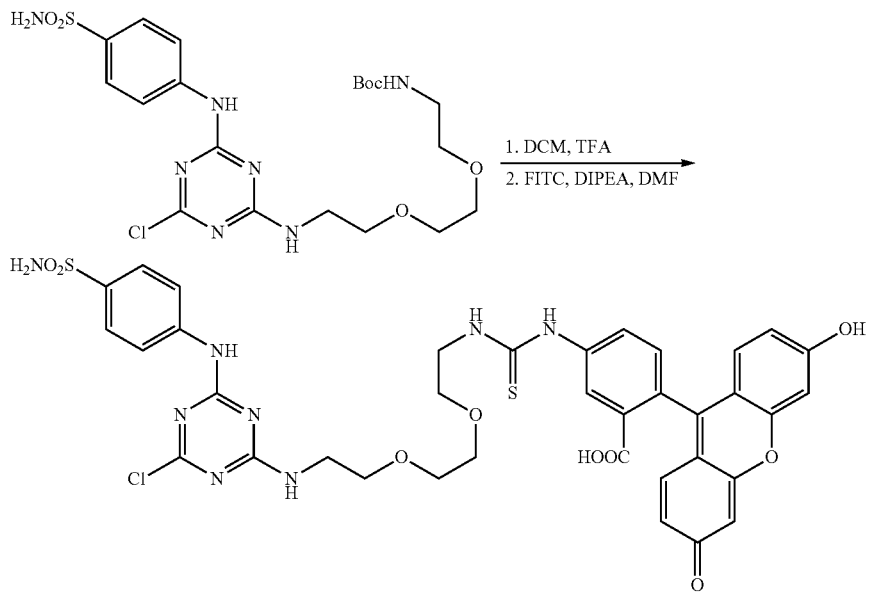

28 (7.5 mg, 14 μmol) was dissolved in a mixture of DCM (1 mL) and TFA (1 mL) and stirred for 30 min at room temperature. The solvent was removed under reduced pressure and the residue dissolved in DMF (1 mL). FITC (5.4 mg, 14 μmol) was added followed by DIPEA (23 μL, 139 μmol) and the reaction stirred for 3 h at room temperature. MeOH (1 mL) was added and the crude reaction mixture purified over reversed-phase HPLC (95% A/5% B to 20% A/80% B over 20 min). Fractions containing the desired product by MS were pooled and lyophilized to yield the title compound as a bright yellow powder (8.1 mg, 11 µmol, 76%).

$^1$H-NMR (400 MHz, DMSO-d$_6$, two rotamers) δ [ppm]=10.31 (br s, 1H), 10.23 (br s, 1H), 9.96 (br s, 2H), 8.21 (br s, 2H), 8.02 (br s, 1H), 7.86-7.77 (m, 2H), 7.69-7.64 (m, 3H), 7.16 (m, 2H), 7.10 (d, J=8.3 Hz, 1H), 6.61-6.48 (m, 6H), 3.61-3.38 (m, 12H); $^{13}$C-NMR (125 MHz, DMSO-d$_6$, two rotamers, signals of PEG linker predicted to overlap) δ [ppm]=181.1, 169.0, 168.5, 166.0, 160.2, 159.3, 159.0, 157.3, 152.4, 142.5, 141.9, 141.0, 139.6, 138.3, 129.5, 127.2, 127.0, 126.9, 124.5, 122.61, 120.0, 113.1, 110.5, 102.7, 70.1, 70.0, 69.1, 68.5, 68.9, 49.1, 44.1; HRMS: (m/z) [M+H]$^+$ calcd. for C$_{36}$H$_{34}$ClN$_8$O$_9$S$_2$, 821.1573. found 821.8567.

4-((4-((2-(2-(2-aminoethoxy)ethoxy)ethyl)amino)-6-chloro-1,3,5-triazin-2-yl)amino)benzenesulfonamide IRDye750 conjugate—3c

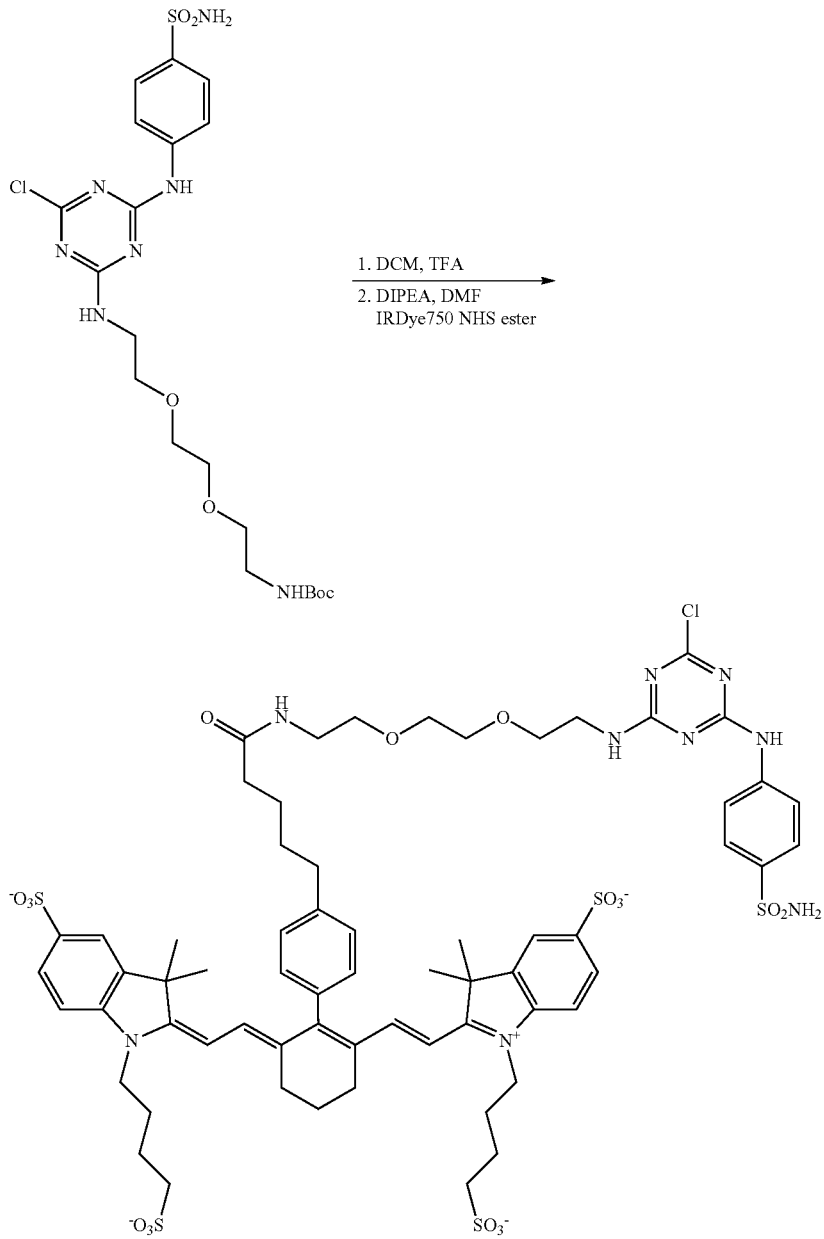

28 (174 µg, 328 nmol) in DMSO (19 µL) was added to a mixture of TFA (100 µL) and DCM (100 µL). The reaction was stirred for 1 h at room temperature and the volatile solvents removed under reduced pressure. To the residual solution, IRDye750 NHS ester (194 µg, 163 nnmol) in DMSO (25 µL) was added followed by DMF (100 µL) and DIPEA (10 µL, 60 µmol). The solution was stirred for 6 h at room temperature and then directly purified over reversed-phase HPLC (95% A/5% B to 40% A/60% B over 30 min).

Fractions containing dye conjugate were identified through their characteristic UV/VIS spectrum ($\lambda_{max}$=750 nm), pooled, lyophilized and dissolved in DMSO (100 μL) to give a dark green stock solution. Its concentration and the reaction yield were determined by measuring the absorbance at 750 nm ($\epsilon_{750}$=260,000 M$^{-1}$ cm$^{-1}$) of stock samples diluted 1:100 into PBS pH 7.4 (510 μM, 51 nmol, 31%).

HRMS: (m/z) [M]$^{3-}$ calcd. for $C_{64}H_{77}ClN_9O_{17}S_5$, 479.4582. found 479.4569.

(E)-N-(2-(2-(2-aminoethoxy)ethoxy)ethyl)-3-((4-((4-sulfamoylphenyl)diazenyl)phenyl)amino)propanamide IRDye750 conjugate—4c

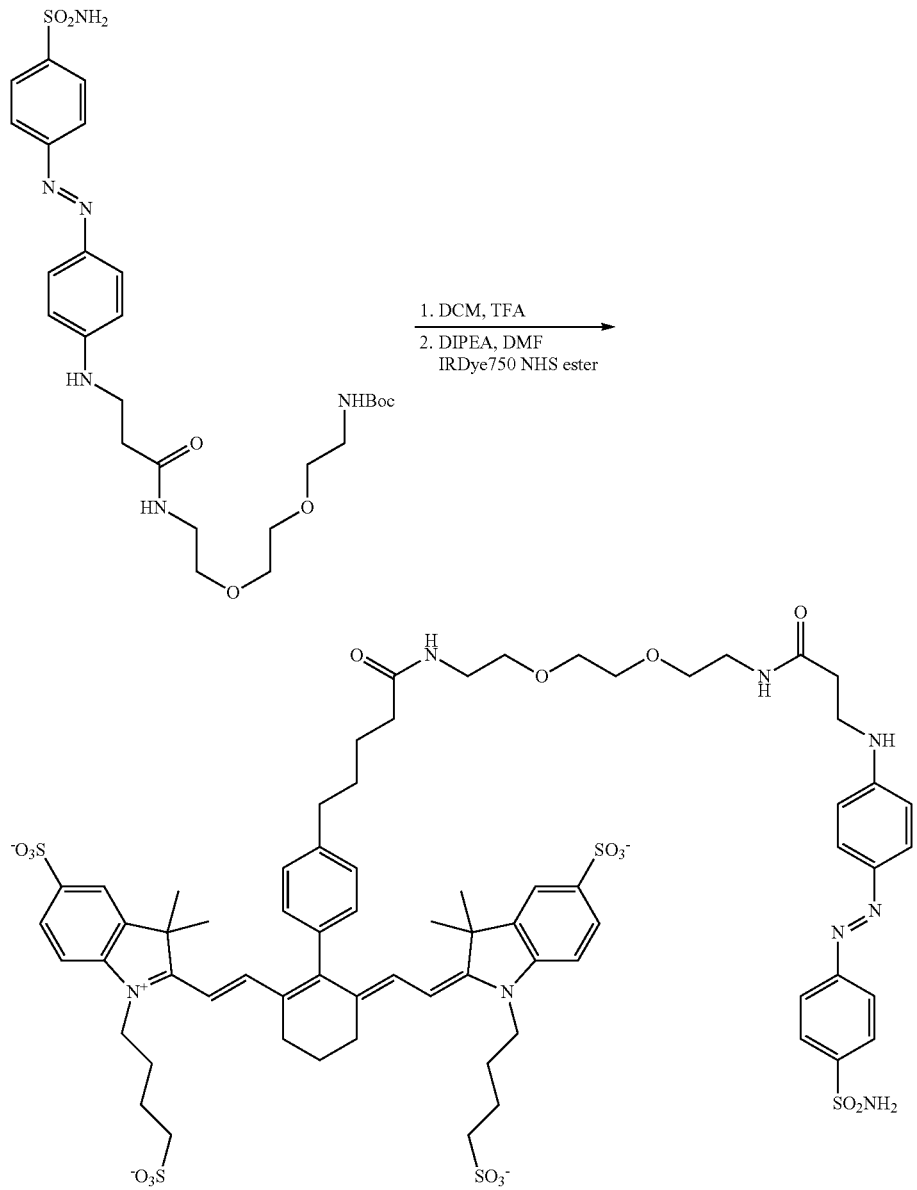

IRDye750 NHS ester (194 μg, 163 nnmol) in DMSO (25 μL) was added followed by DMF (100 μL) and DIPEA (10 μL, 60 μmol). The solution was stirred for 6 h at room temperature and then directly purified over reversed-phase HPLC (95% A/5% B to 40% A/60% B over 30 min). Fractions containing dye conjugate were identified through their characteristic UV/VIS spectrum ($\lambda_{max}$=750 nm), pooled, lyophilized and dissolved in DMSO (100 μL) to give a dark green stock solution. Its concentration and the reaction yield were determined by measuring the absorbance at 750 nm 29 (188 μg, 320 nmol) in DMSO (20 μL) was added to a mixture of TFA (100 μL) and DCM (100 μL). The reaction was stirred for 1 h at room temperature and the volatile solvents removed under reduced pressure. To the residue, ($\epsilon_{750}$=260,000 M$^{-1}$ cm$^{-1}$) of stock samples diluted 1:100 into PBS pH 7.4 (390 μM, 39 nmol, 24%).

HRMS: (m/z) [M+Na]$^{2-}$ calcd. for $C_{70}H_{85}N_8NaO_{18}S_5$, 754.2247. found 754.2248.

N-(2-(2-(2-aminoethoxy)ethoxy)ethyl)-4-sulfamoyl-benzamide fluorescein conjugate—5a

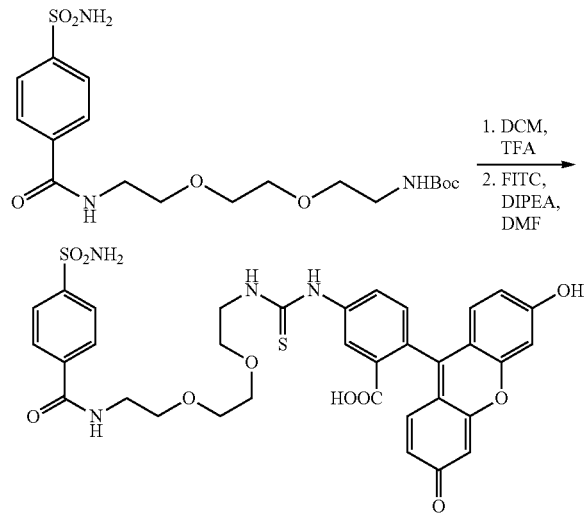

31 (5.0 mg, 12 μmol) was dissolved in a mixture of DCM (0.5 mL) and TFA (0.5 mL) and stirred for 1 h at room temperature. The solvents were removed under reduced pressure and the residue dissolved in DMF (0.5 mL). DIPEA (31 μL, 187 μmol) was added followed by FITC (4.5 mg, 12 μmol). The reaction was stirred for 2 h at room temperature, diluted with MeOH (0.5 mL) and purified over reversed-phase HPLC (80% A/20% B to 20% A/80% B over 20 min). Fractions containing product by MS were pooled end lyophilized to give the product as a bright yellow powder (6.3 mg, 10 μmol, 83%).
$^1$H-NMR (400 MHz, DMSO-$d_6$, only SO$_2$NH$_2$ but not NH and OH visible) δ [ppm]=8.74 (t, J=5.2 Hz, 1H), 8.27 (s, 1H), 8.18 (s, 1H), 8.00 (d, J=8.1 Hz, 2H), 7.90 (d, J=8.1 Hz, 2H), 7.74 (d, J=7.9 Hz, 1H), 7.17 (d, J=8.2 Hz, 1H), 6.65-6.54 (m, 6H), 3.68 (br s, 2H), 3.61-3.56 (m, 8H), 3.47-3.42 (m, 2H); $^{13}$C-NMR (125 MHz, DMSO-$d_6$, signals from PEG linker predicted to overlap) δ [ppm]=181.05, 169.0, 165.8, 160.0, 159.1, 158.8, 152.3, 152.4, 147.5, 146.7, 141.8, 137.8, 129.5, 128.3, 127.0, 126.1, 124.6, 116.9, 113.1, 110.2, 102.7, 70.1, 70.0, 69.3, 68.9, 44.2; HRMS: (m/z) [M+H]$^+$ calcd. for C$_{34}$H$_{33}$N$_4$O$_{10}$S$_2$, 721.1633. found 720.1620.

N-(2-(2-(2-aminoethoxy)ethoxy)ethyl)-4-sulfamoyl-benzamide IRDye750 conjugate—5c

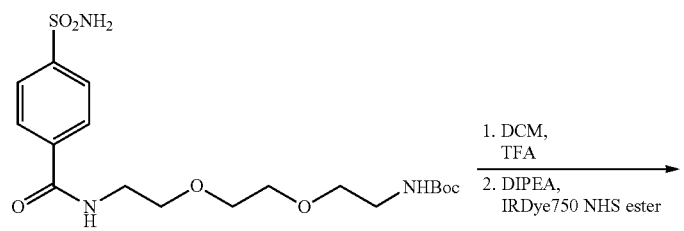

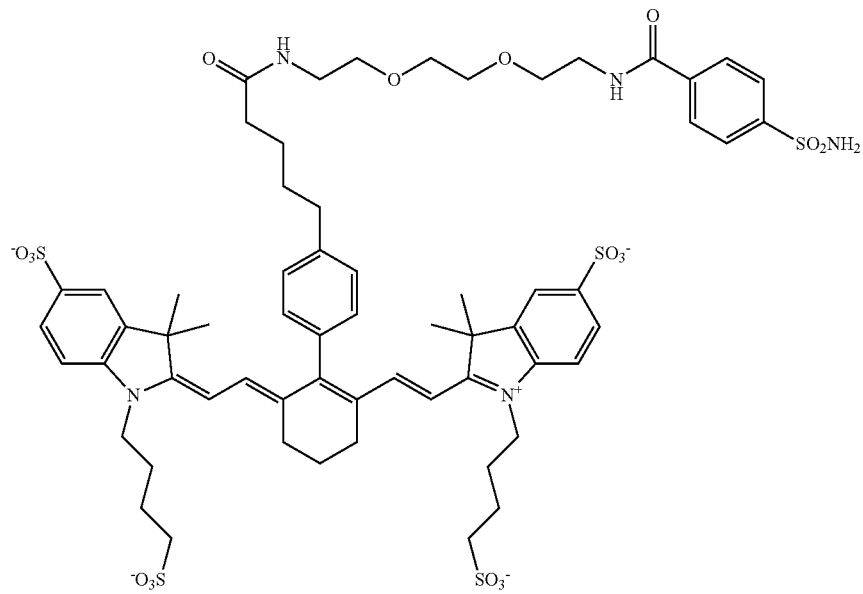

31 (138 μg, 320 nmol) in DMSO (29 μL) was added to a mixture of TFA (100 μL) and DCM (100 μL). The reaction was stirred for 1 h at room temperature and the volatile solvents removed under reduced pressure. To the residual solution, IRDye750 NHS ester (194 μg, 163 nnmol) in DMSO (25 μL) was added followed by DMF (100 μL) and DIPEA (10 μL, 60 μmol). The solution was stirred for 6 h at room temperature and then directly purified over reversed-phase HPLC (95% A/5% B to 40% A/60% B over 30 min). Fractions containing dye conjugate were identified through their characteristic UV/VIS spectrum ($\lambda_{max}$=750 nm), pooled, lyophilized and dissolved in DMSO (100 μL) to give a dark green stock solution. Its concentration and the reaction yield were determined by measuring the absorbance at 750 nm ($\epsilon_{750}$=260,000 M$^{-1}$ cm$^{-1}$) of stock samples diluted 1:200 into PBS pH 7.4 (1.23 mM, 123 nmol, 75%).

HRMS: (m/z) [M+2H]$^{2+}$ calcd. for $C_{62}H_{78}N_5O_{18}S_5$, 1340.3951. found 1340.3932.

Tert-butyl
(2-(2-(2-aminoethoxy)ethoxy)ethyl)carbamate
fluorescein conjugate—6a 19 (10 mg, 40 μmol) and FITC (16 mg, 41 μmol) were dissolved in DMF (1 mL) and DIPEA (10 μL, 48 μmol) was added. The reaction was stirred for 2 h at room temperature, diluted with MeOH (1 mL) and purified over reversed-phase HPLC (80% A/20% B to 20% A/80% B over 20 min). Fractions containing the desired product by MS were pooled and lyophilized to give the product as a yellow powder (18 mg, 29 μmol, 72%).

$^1$H-NMR (500 MHz, DMSO-d$_6$) δ [ppm]=8.45 (br, 1H), 7.76 (br, 1H), 7.18 (d, J=8.3 Hz, 1H), 6.71-6-69 (m, 2H), 6.37-6.56 (m, 4H), 3.63-3.53 (m, 8H), 3.39 (t, J=6.0, 2H), 3.07 (br, 2H), 1.35 (s, 9H); $^{13}$C-NMR (125 MHz, DMSO-d$_6$) δ [ppm]=180.9, 169.0, 159.9, 156.0, 152.4, 147.4, 141.8, 129.5, 129.7, 127.0, 124.5, 116.7, 113.0, 110.3, 110.2, 102.7, 78.1, 70.1, 70.0, 69.7, 68.9, 67.02, 44.0, 28.6; HRMS: (m/z) [M+H]$^+$ calcd. for $C_{32}H_{36}N_3O_9S$, 638.2167. found 638.2160.

tert-butyl
(2-(2-(2-aminoethoxy)ethoxy)ethyl)carbamate
Alexa546 conjugate—6b

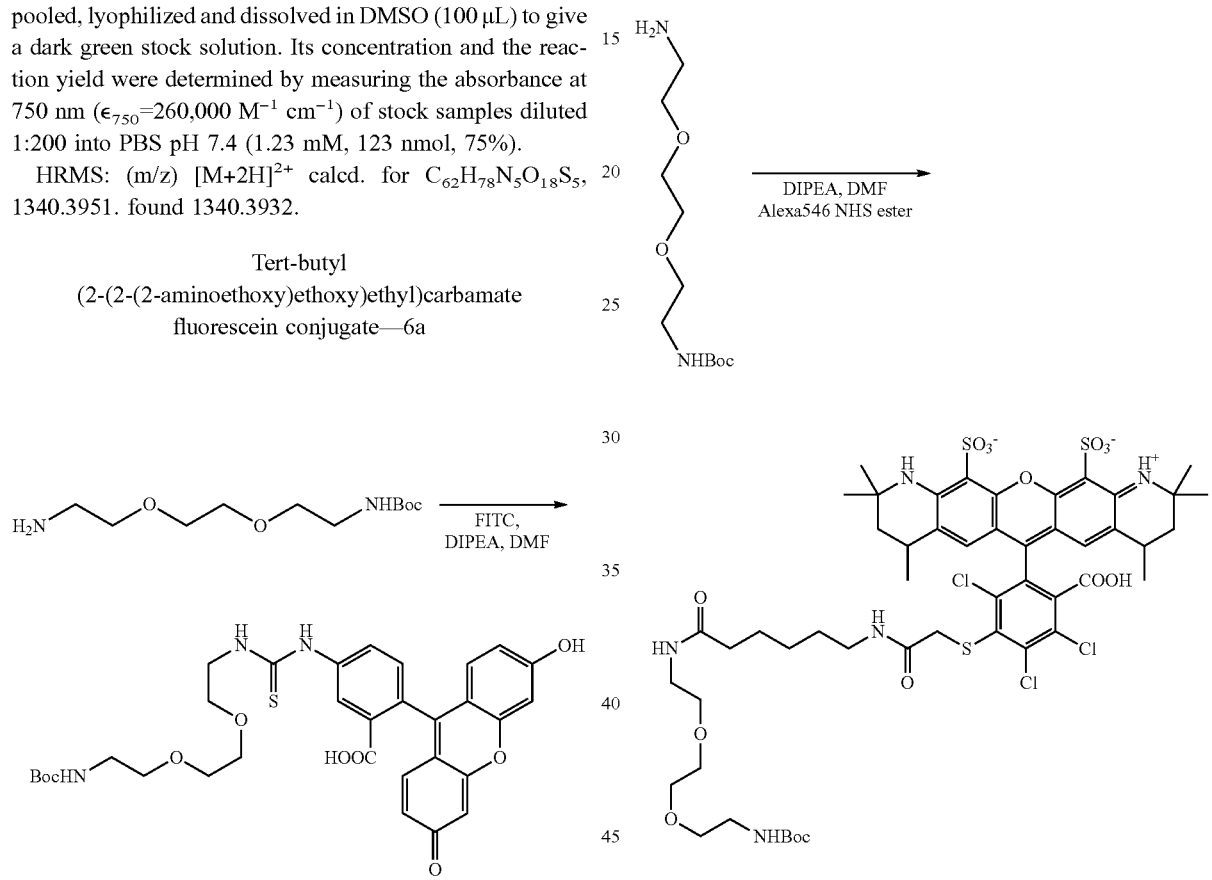

To 19 (233 μg, 943 nmol) in DMSO (6 μL) was added Alexa546 NHS ester (100 μg, 86 nmol). DIPEA (2 μL, 12 μmol) and DMF (50 μL) were added and the mixture stirred for 2 h at room temperature. The reaction was diluted with MeOH (50 μL) and purified over reversed-phase HPLC (95% A/5% B to 20% A/80% B over 20 min). Fractions containing the product as identified through its characteristic UV/VIS spectrum were pooled ($\lambda_{max}$=550 nm), lyophilized and dissolved in 100 μL PBS pH 7.4 to give a dark purple solution. Its concentration and the reaction yield were determined by measuring the absorbance at 556 nm ($\epsilon_{556}$=112,000 M$^{-1}$ cm$^{-1}$) of stock samples diluted 1:100 into PBS pH 7.4 (555 μM, 56 nmol, 65%).

HRMS: (m/z) [M+2H]$^+$ calcd. for $C_{51}H_{67}Cl_3N_5O_{15}S_3$, 1190.2856. found 1190.2859.

AAZ Targeted CBI Carbonate—7a

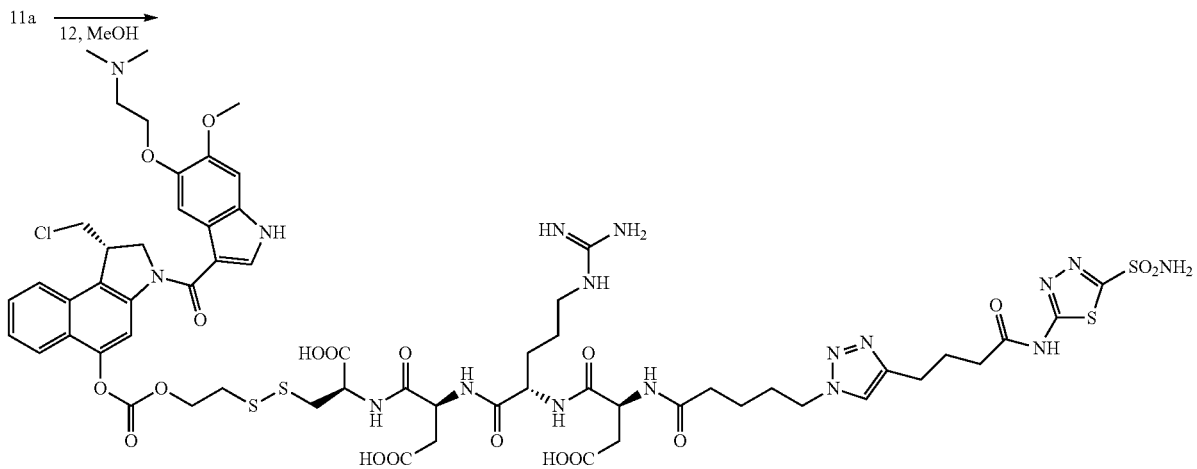

AAZ targeted charged linker 11a (7.8 mg, 8.6 μmol) and 12 (5.1 mg, 7.2 μmol) were dissolved in degassed MeOH (0.5 mL) and stirred for 6 h at room temperature. The reaction mixture was directly purified over reversed-phase HPLC (95% A/5% B to 20% A/80% B over 20 min), fractions containing the product by MS were pooled and lyophilized to give the title compound as a white powder (5.5 mg, 3.7 μmol, 47%).

$^1$H-NMR (500 MHz, DMSO-$d_6$) δ [ppm]=11.57 (s, 1H), 8.36 (s, 1H), 8.31 (br s, 3H), 8.20 (d, J=7.5 Hz, 1H), 8.06 (d, J=8.5 Hz, 1H), 8.03 (br s, 2H), 7.89 (d, J=8.5 Hz, 2H), 7.85 (s, 1H), 7.63 (t, J=8.0, 1H), 7.53 (t, J=8.0 Hz, 1H), 7.31 (s, 1H), 7.21 (br s, 4H), 7.13 (d, J=2.0 Hz, 1H), 7.02 (s, 1H), 4.87 (t, J=10.0 Hz, 1H), 4.63-4.52 (m, 5H), 4.45-4.40 (m, 1H), 4.29-4.26 (m, 6H), 4.10 (dd, J=11.2, 3.1 Hz, 1H), 4.00 (dd, J=11.2, 6.9 Hz, 1H), 3.84 (s, 3H), 3.51-3.49 (m, 2H), 3.25-3.21 (m, 1H), 3.14-3.11 (m, 2H), 3.07-3.02 (m, 3H), 2.90 (s, 6H), 2.73-2.57 (m, 6H), 2.55-2.45 (m, 2H), 2.13 (t, J=7.1 Hz, 2H), 1.96-1.90 (m, 2H), 1.81-1.73 (m, 3H), 1.55-1.40 (m, 5H); HRMS: (m/z) [M+2H]$^{2+}$ calcd. for $C_{60}H_{78}ClN_{17}O_{19}S_4$, 751.7110. found 751.7109.

Untargeted CBI Carbonate—7b

Activated carbonate 12 (5.0 mg, 7.1 μmol) and untargeted charged linker 11b (10 mg, 14 μmol) were dissolved in degassed MeOH (0.5 mL) and stirred for 6 h at room temperature. The reaction mixture was directly purified over reversed-phase HPLC (95% A/5% B to 20% A/80% B over 20 min), fractions containing the product by MS were pooled and lyophilized to give the title compound as a white powder (4.1 mg, 3.1 μmol, 43%).

$^1$H-NMR (500 MHz, DMSO-$d_6$) δ [ppm]=11.57 (s, 1H), 8.37 (s, 1H), 8.21 (d, J=7.4 Hz, 1H), 8.17 (br s, 2H), 8.06 (d, J=8.5 Hz, 1H), 7.96 (d, J=7.3 Hz, 1H), 7.89 (d, J=8.5 Hz, 1H), 7.82 (s, 1H), 7.64 (t, J=7.5 Hz, 1H), 7.53 (t, J=8.0 Hz, 1H), 7.40-6.77 (br, 4H), 7.31 (s, 1H), 7.13 (d, J=1.9 Hz, 1H), 7.03 (s, 1H), 4.86 (t, J=10.1 Hz, 1H), 4.63-4.41 (m, 7H), 4.30-4.21 (m, 5H), 4.10 (dd, J=11.1, 2.8 Hz, 1H), 4.00 (dd, J=11.2, 7.0 Hz, 1H), 3.85 (s, 3H), 3.54-3.52 (m, 2H), 3.22-2.98 (m, 6H), 2.92 (s, 6H), 2.75-2.66 (m, 2H), 2.59 (t, J=7.6 Hz, 2H), 2.54-2.47 (m, 2H), 2.24 (t, J=7.4 Hz, 2H), 2.13 (t, J=7.2 Hz, 2H), 1.82-1.70 (m, 5H), 1.53-1.41 (m, 5H); HRMS: (m/z) [M+H]$^+$ calcd. for $C_{58}H_{75}ClN_{13}O_{18}S_2$, 1340.4477. found 1340.4466.

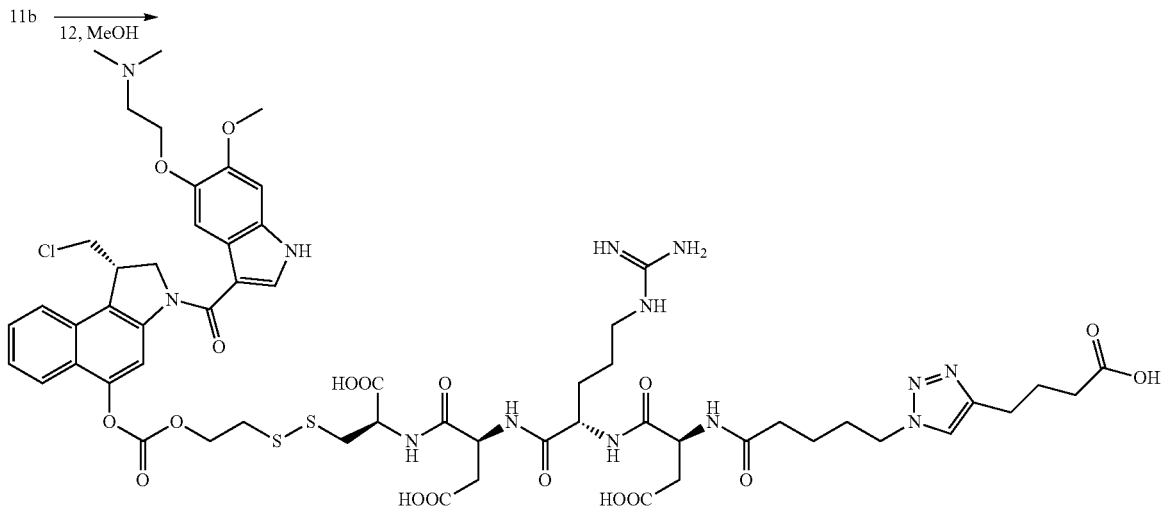

AAZ Targeted CBI Carbamate—8a

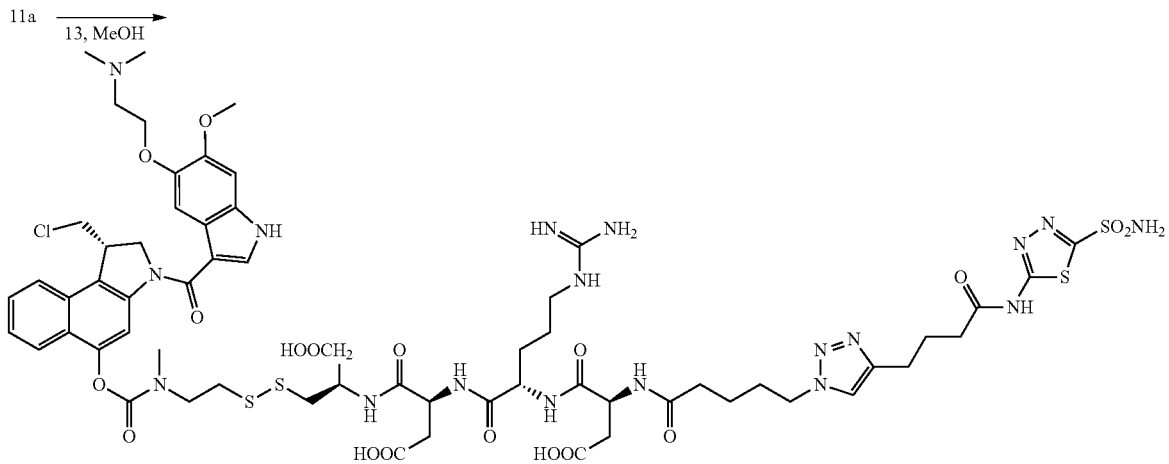

AAZ targeted charged linker 11a (7.6 mg, 8.3 μmol) and activated carbamate 13 (2.7 mg, 3.8 μmol) were dissolved in degassed MeOH (0.5 mL) and stirred for 6 h at room temperature. The reaction mixture was directly purified over reverse-phased HPLC (95% A/5% B to 20% A/80% B over 20 min), fractions containing the product by MS were pooled and lyophilized to give the title compound as a white powder (2.0 mg, 1.3 μmol, 35%).

$^1$H-NMR (500 MHz, DMSO-d$_6$, mixture of 2 rotamers) δ [ppm]=13.00 (br s, 1H), 12.39 (br s, 1H), 11.54 (s, 1H), 9.72 (br s, 1H), 8.32 (s, 2H), 8.24-8.18 (m, 3H), 8.14-8.10 (m, 1H), 8.03-7.97 (m, 2H), 7.92-7.86 (m, 1H), 7.83 (s, 1H), 7.62-7.58 (m, 1H), 7.51-7.44 (m, 2H), 7.32-7.01 (m, 7H), 4.85 (t, J=10.6 Hz, 1H), 4.61-4.47 (m, 4H), 4.43-4.38 (m, 1H), 4.30-4.19 (m, 5H), 4.11-4.08 (m, 1H), 3.99-3.89 (m, 2H), 3.85 (s, 3H), 3.63-3.53 (m, 4H), 3.25-2.96 (m, 8H), 2.93 (s, 6H), 2.75-2.57 (m, 6H), 2.53-2.47 (m, 2H), 2.13 (t, J=7.0 Hz, 2H), 1.96-1.90 (m, 2H), 1.78-1.68 (m, 3H), 1.54-1.40 (m, 5H); HRMS: (m/z) [M+2H]$^{2+}$ calcd. for C$_{61}$H$_{81}$ClN$_{18}$O$_{18}$S$_4$, 758.2268. found 758.2267.

Untargeted CBI Carbamate—8b

Activated carbamate 13 (5.0 mg, 6.9 μmol) and untargeted charged linker 11b (10 mg, 14 μmol) were dissolved in degassed MeOH (0.5 mL) and stirred for 6 h at room temperature. The reaction mixture was directly purified over reverse-phased HPLC (95% A/5% B to 20% A/80% B over 20 min), fractions containing the product by MS were pooled and lyophilized to give the title compound as a white powder (5.1 mg, 3.7 μmol, 54%).

$^1$H-NMR (500 MHz, DMSO-d$_6$, mixture of 2 rotamers) δ [ppm]=12.4 (br s, 3H) 11.54 (s, 1H), 8.24-8.14 (m, 4H), 8.03-7.87 (m, 3H), 7.82 (s, 1H), 7.63-7.47 (m, 3H), 7.32-6.82 (m, 7H), 4.85 (t, J=10.0 Hz, 1H), 4.62-4.53 (m, 3H), 4.50-4.44 (br m, 1H), 4.43-4.37 (br m, 1H), 4.30-4.20 (m, 5H), 4.11-4.07 (m, 1H), 3.99-3.87 (m, 2H), 3.85 (s, 3H), 3.64-3.50 (m, 4H), 3.25-2.95 (m, 8H), 2.93 (s, 6H), 2.75-2.58 (m, 4H), 2.53-2.46 (m, 2H), 2.25 (t, J=7.4 Hz, 2H), 2.12 (t, J=7.3 Hz, 2H), 1.84-1.68 (m, 5H), 1.56-1.38 (m, 5H); HRMS: (m/z) [M+2H]$^{2+}$ calcd. for C$_{59}$H$_{79}$ClN$_{14}$O$_{17}$S$_2$, 677.2433. found 677.2430.

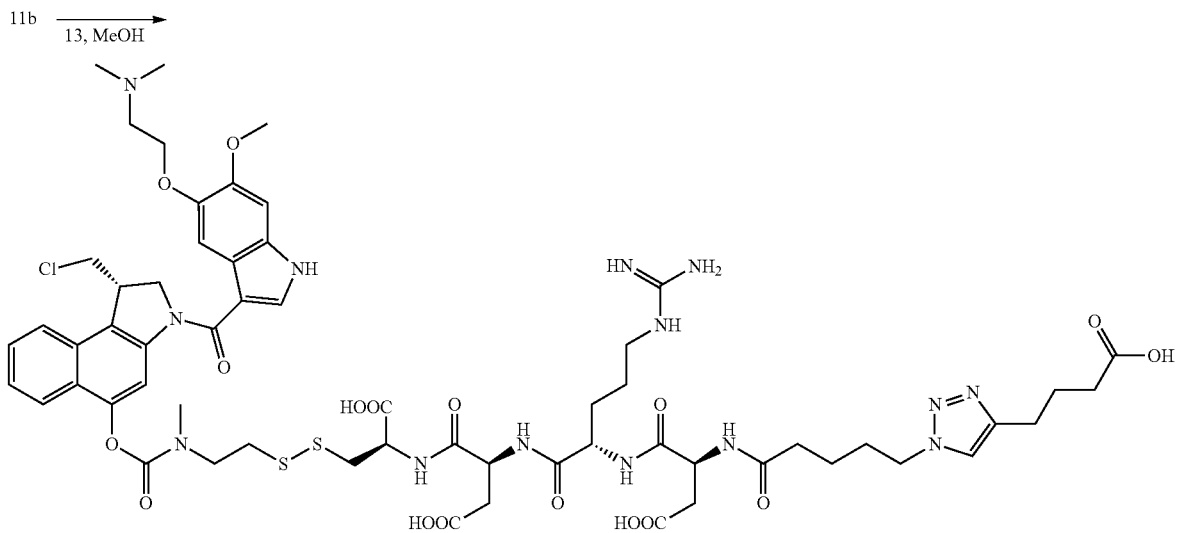

Targeted DM1 Conjugate—9a

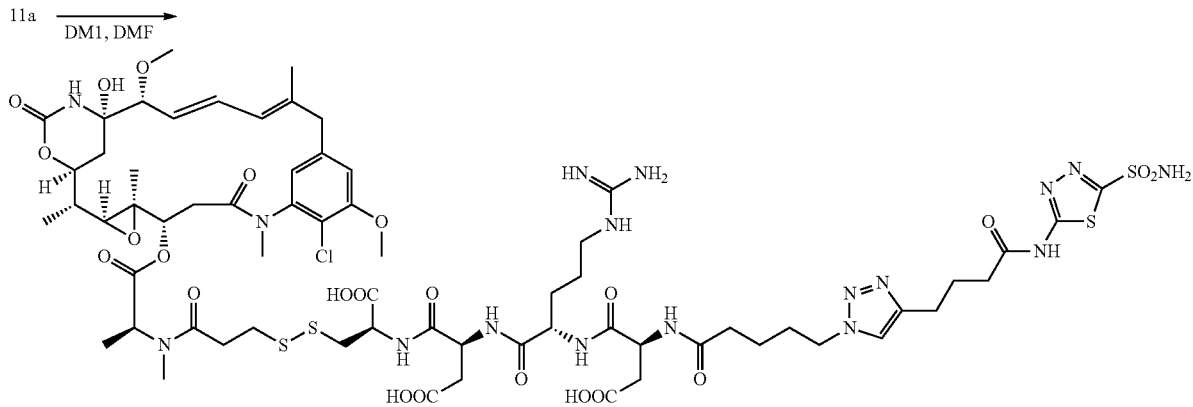

CysAspArgAsp-Linker-AAZ 11a (40 mg, 40 µmol) was dissolved in degassed MeOH (5 mL) and 2,2'-dipyridyldisulfide (13.2 mg, 60 µmol) was added. The mixture was stirred at room temperature for 12 h and added drop wise to ice cold diethyl ether (40 mL). The precipitate was collected by centrifugation, re-dissolved in MeOH and precipitated again with ice cold diethyl ether (40 mL) and dried under vacuum to give the activated disulfide as a white residue (20 mg, 20 µmol, 49%). An aliquot of the activated disulfide (8 mg, 7.8 µmol) was dissolved in DMF (500 µL) and DM1 free thiol (5.5 mg, 7.4 µmol) added. The reaction was allowed to stand at room temperature for 48 h after which the product was recovered by reversed phase HPLC (95% A/5% B to 20% A/80% B over 20 min). Fractions containing the desired product by MS were pooled and lyophilized to yield the title compound as an off white powder (9.0 mg, 5.5 µmol, 74%).

HRMS: (m/z) [M+2H]$^{2+}$ calcd. for $C_{65}H_{94}ClN_{17}O_{23}S_4$ 821.7634. found 821.7633.

Untargeted DM1 Conjugate—9b

CysAspArgAsp-Linker-COOH 11b (21 mg, 28 µmol) was dissolved in degassed MeOH (5 mL) and reduced with TCEP.HCl (16 mg, 56 µmol) for 2 h at room temperature. 2,2'-Dipyridyldisulfide (25 mg, 114 µmol) was added and the mixture stirred for 12 h at room temperature. The reaction was precipitated into ice cold diethyl ether (40 mL), the product collected by centrifugation, re-dissolved in MeOH (5 mL) and precipitated again with ice cold diethyl ether (40 mL). The precipitate was dried under vacuum to give the activated disulfide as a white residue (20 mg, 23 µmol, 83%). An aliquot of the activated disulfide (10 mg, 12 µmol) was dissolved in DMF (500 µL) and DM1 free thiol (8.6 mg, 12 µmol) was added. The reaction was allowed to stand at room temperature for 48 h after which the product was recovered by reversed phase HPLC (95% A/5% B to 20% A/80% B over 20 min). Fractions containing the desired product by MS were pooled and lyophilized to yield the title compound as an off white powder (7.0 mg, 4.7 µmol, 40%).

HRMS: (m/z) [M+2H]$^{2+}$ calcd. for $C_{63}H_{92}ClN_{13}O_{22}S_2$, 740.7799. found 740.7792.

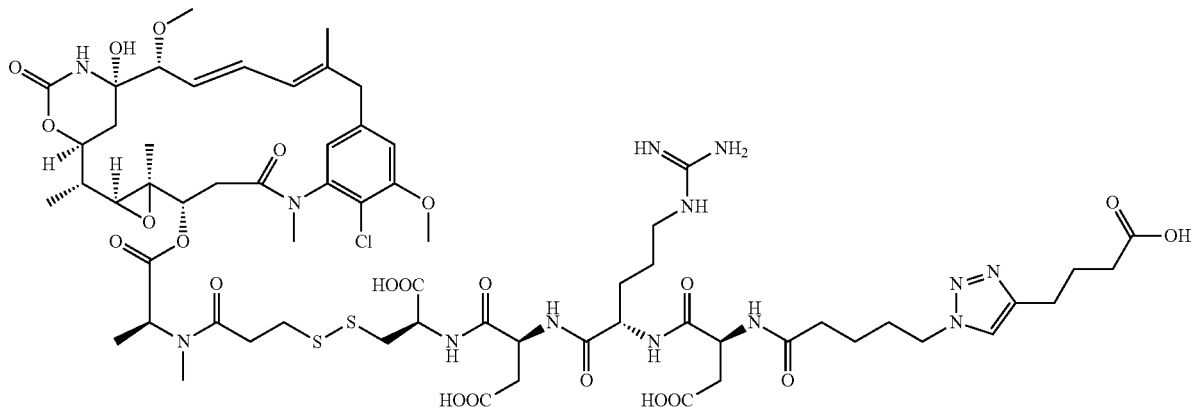

N-(5-sulfamoyl-1,3,4-thiadiazol-2-yl)hex-5-ynamide—10

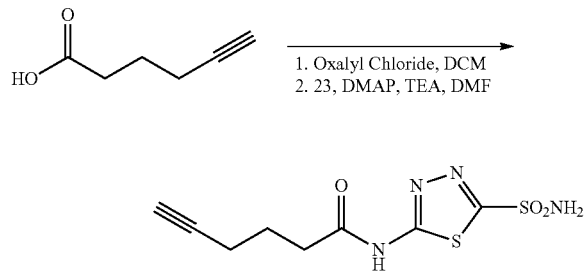

A solution of 5-hexynoic acid (1.4 mL, 12.9 mmol) and DMF (50 µL) in DCM (50 mL) was cooled on ice and oxalyl chloride (1 mL, 11.7 mmol) was added drop wise over 15 min. The reaction was allowed to warm to room temperature, stirred until evanescence ceased and then concentrated under reduced pressure. The yellow liquid was added drop wise to a solution of 23 (2.3 g, 12.9 mmol) and pyridine (943 µL, 25.8 mmol) in DMF (15 mL) and the reaction stirred for 3 h at room temperature. The solvent was removed under reduced pressure and the residue purified by flash column chromatography (EtOAc) to give the product as an off-white solid (2.8 g, 79%).

$^1$H-NMR (400 MHz, DMSO-$d_6$) δ [ppm]=2.81 (t, J=2.6 Hz, 1H), 2.65 (t, J=7.4 Hz, 2H), 2.24 (td, J=7.1, 2.6 Hz, 2H), 1.84-1.77 (m, 2H); $^{13}$C-NMR (100 MHz, DMSO-$d_6$) δ [ppm]=171.5, 164.2, 160.9, 83.6, 71.8, 33.6, 23.1, 17.2; HRMS: (m/z) [M+H]$^+$ calcd. for $C_8H_{11}N_4O_3S_6$, 275.0267. found 275.0268.

CysAspArgAsp-Linker-Acetazolamide—11a mL). The peptide was extended with Fmoc-Asp(tBu)-OH, Fmoc-Arg(Pbf)-OH and Fmoc-Asp(tBu)-OH in the indicated order and then capped with 5-azido-valerate. For this purpose, the Fmoc protected amino acid or azido acid (3.0 eq), HBTU (3.0 eq), HOBt (3.0 eq) and DIPEA (6.0 eq) were dissolved in DMF (5 mL), the mixture was allowed to stand for 1 min at room temperature and then reacted with the resin for 1 h under gentle agitation. After washing with DMF (6×1 min×5 mL) the Fmoc group was removed with 20% piperidine in DMF (1×1 min×5 min and 2×10 min×5 mL) and the resin washed with DMF (6×1 min×5 mL) before the next coupling step was initiated. After coupling of 5-azido-valerate, a solution of CuI (0.3 eq), TBTA (0.3 eq) and alkyne 10 (6 eq) in a mixture of DMF (2.5 mL) and THF (2.5 mL) was prepared and reacted with the resin for 2 h at room temperature. After washing with DMF (3×1 min×5 mL), 50 mM aq. EDTA solution (3×1 min×5 mL), DMF (3×1 min×5 mL) and DCM (3×1 min×5 mL), the compound was cleaved by agitating the resin with a mixture of TFA (4.5 mL), TIS (250 µL) and H$_2$O (250 µL) for 2 h at room temperature. The resin was washed with TFA (1×5 min×5 mL) and the combined cleavage and washing solutions added drop-wise to ice cold diethyl ether (100 mL). The precipitate was collected by centrifugation and the product purified by reversed-phase HPLC (95% A/5% B to 20% A/80% B over 20 min). After lyophilization the title compound was collected as a white powder (135 mg, 0.14 mmol, 33%).

$^1$H-NMR (500 MHz, DMSO-$d_6$) δ [ppm]=13.00 (s, 1H), 8.31 (s, 2H), 8.23-8.20 (m, 2H), 7.98 (d, J=7.5 Hz, 1H), 7.93 (d, J=7.8 Hz, 1H), 7.82 (br m, 1H), 7.53 (br m, 1H), 7.27-7.06 (br m, 4H), 4.59-4.51 (m, 2H), 4.40-4.36 (m, 1H), 4.27 (t, J=6.7 Hz, 2H), 4.21-4.20 (m, 1H), 3.06-3.04 (br m, 2H), 2.87-2.47 (m, 9H), 2.38 (t, J=8.6 Hz, 1H), 2.14 (t, J=7.0 Hz, 2H), 1.95-1.90 (m, 2H), 1.77-1.69 (m, 3H), 1.54-1.39 (m, 5H); $^{13}$C-NMR (125 MHz, DMSO-$d_6$) δ [ppm]=172.7,

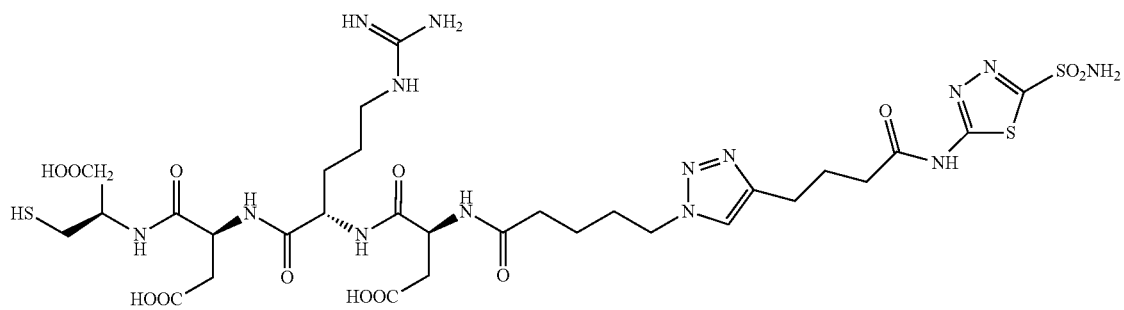

Commercially available pre-loaded Fmoc-Cys(Trt) on Tentagel resin (500 mg, 0.415 mmol, RAPP Polymere) was swollen in DMF (3×5 min×5 mL), the Fmoc group removed with 20% piperidine in DMF (1×1 min×5 mL and 2×10 min×5 mL) and the resin washed with DMF (6×1 min×5

172.5, 172.3, 172.1, 171.7, 171.6, 171.5, 170.9, 164.7, 161.5, 157.2, 146.5, 122.3, 54.9, 52.7, 50.1, 49.9, 49.3, 40.9, 36.3, 36.2, 34.7, 29.6, 29.4, 35.9, 25.2, 24.8, 24.6, 22.5; HRMS: (m/z) [M+H]$^+$ calcd. for $C_{30}H_{47}N_{14}O_{13}S_3$, 995.1966. found 995.1964.

CysAspArgAsp-Linker-COOH—11b

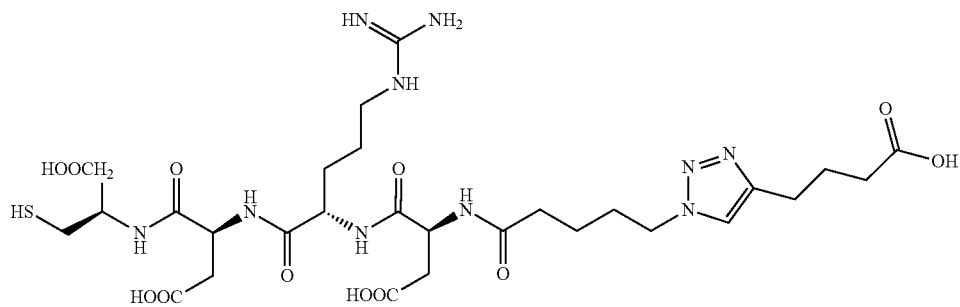

Commercially available pre-loaded Fmoc-Cys(Trt) on Tentagel resin (500 mg, 0.415 mmol, RAPP polymere) was swollen in DMF (3×5 min×5 mL), the Fmoc group removed with 20% piperidine in DMF (1×1 min×5 mL and 2×10 min×5 mL) and the resin washed with DMF (6×1 min×5 mL). The peptide was extended with Fmoc-Asp(OtBu)-OH, Fmoc-Arg(Pbf)-OH and Fmpc-Asp(OtBu)-OH in the indicated order and then capped with 5-azido-valerate. For this purpose, the Fmoc protected amino acid or azido acid (3.0 eq), HBTU (3.0 eq), HOBt (3.0 eq) and DIPEA (6.0 eq) were dissolved in DMF (5 mL), the mixture was allowed to stand for 1 min at room temperature and then reacted with the resin for 1 h under gentle agitation. After washing with DMF (6×1 min×5 mL) the Fmoc group was removed with 20% piperidine in DMF (1×1 min×5 min and 2×10 min×5 mL) and the resin washed with DMF (6×1 min×5 mL) before the next coupling step was initiated. After coupling of 5-azido-valerate, a solution of CuI (0.3 eq), TBTA (0.3 eq) and 5-hexynoic acid (6 eq) in a mixture of DMF (2.5 mL) and THF (2.5 mL) was prepared and reacted with the resin for 2 h at room temperature. After washing with DMF (3×1 min×5 mL), 50 mM aq. EDTA solution (3×1 min×5 mL), DMF (3×1 min×5 mL) and DCM (3×1 min×5 mL), the compound was cleaved by agitating the resin with a mixture of TFA (4.4 mL), phenol (250 µL), water (250 µL) and TIPS (100 µL) for 2 h at room temperature. The resin was washed with TFA (1×5 min×5 mL) and the combined cleavage and washing solutions added drop-wise to ice cold diethyl ether (100 mL). The precipitate was collected by centrifugation and the product purified by reversed-phase HPLC (95% A/5% B to 20% A/80% B over 20 min). After lyophilization the title compound was collected as a white powder (116 mg, 0.16 mmol, 43%).

$^1$H-NMR (500 MHz, MeOH-$d_4$) δ [ppm]=7.81 (s, 1H), 4.58-4.51 (m, 2H), 4.30-4.23 (m, 4H), 3.09 (t, J=6.9 Hz, 2H), 2.91-2.60 (m, 8H), 2.25 (t, J=7.4 Hz, 2H), 2.18 (t, J=7.4 Hz, 2H), 1.90-1.77 (m, 5H), 1.65-1.48 (m, 5H); $^{13}$C-NMR (125 MHz, DMSO-$d_6$) δ [ppm]=174.6, 173.6, 172.7, 172.2, 172.0, 171.6, 171.4, 170.7, 157.1, 146.7, 122.3, 54.8, 52.7, 49.9, 49.8, 49.3, 40.8, 36.2, 34.7, 33.4, 33.1, 29.6, 25.8, 25.1, 24.8, 24.7, 22.5; HRMS: (m/z) [M+H]$^+$ calcd. for $C_{28}H_{46}N_{10}O_{12}S$, 745.2934. found 745.2931.

Seco CBI Drug Carbonate Pyridyl Disulfide—12

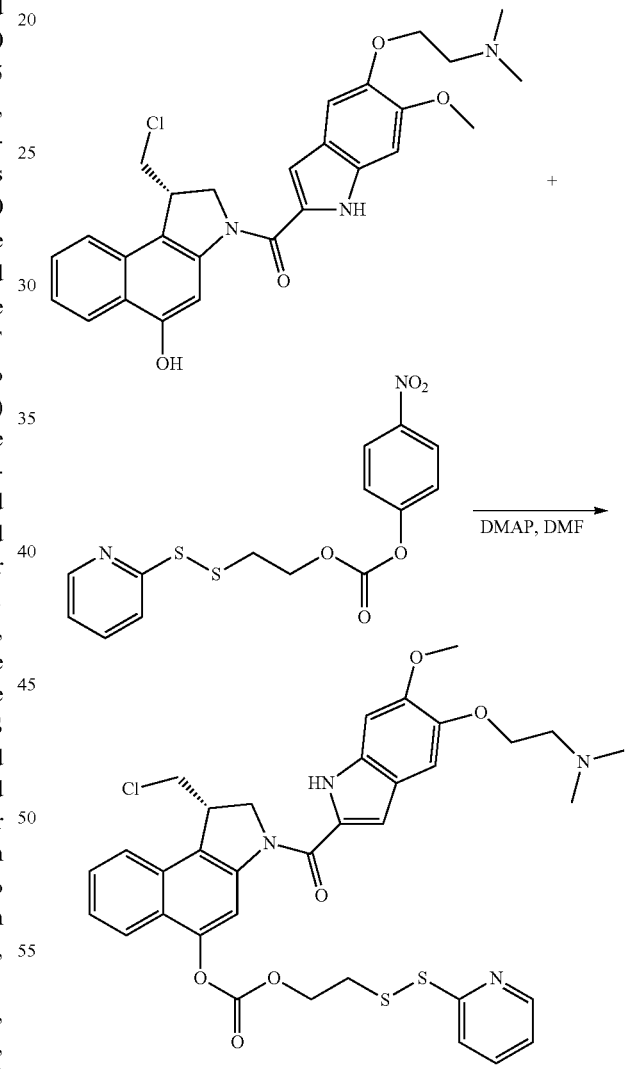

Seco CBI drug 14 (10 mg, 20 µmol, 1 eq), activated carbonate 16 (7.2 mg, 20 µmol, 1 eq) and N,N-dimethyl-aminopyridine (DMAP, 2.4 mg, 50 µmol, 2.5 eq) were dissolved in DMF (2 mL) and stirred for 5 h at room temperature. The reaction mixture was diluted with MeOH (2 mL) and purified over HPLC (95% A/5% B to 20% A/80% B over 20 min). Fractions containing the desired product my MS were pooled and lyophilized to yield the title compound as an off white powder (10.1 mg, 14.3 μmol, 72%).

$^1$H-NMR (400 MHz, MeOD-d$_4$) δ [ppm]=8.45 (br s, 1H) 8.34 (s, 1H), 7.94-7.81 (m, 4H), 7.66 (dt, J=6.9, 1.1 Hz, 1H), 7.59 (dt, J=6.9, 1.0 Hz, 1H), 7.33 (s, 1H), 7.26 (m, 1H), 7.06 (s, 1H), 6.99 (s, 1H), 4.70-4.61 (m, 2H), 4.58 (t, J=6.0 Hz, 2H), 4.33 (t, J=4.9 Hz, 2H), 4.24-4.20 (m, 1H), 4.00 (dd, J=11.4, 3.3 Hz, 1H), 3.89 (s, 3H), 3.71 (dd, J=11.3, 8.2 Hz, 1H), 3.60 (t, J=4.9 Hz, 2H), 3.25 (t, J=6.0 Hz, 2H), 3.06 (s, 6H); $^{13}$C-NMR (125 MHz, MeOD-d$_4$) δ [ppm]=160.3, 159.3, 153.8, 150.0, 149.2, 146.9, 143.4, 141.2, 137.9, 132.9, 129.7, 128.7, 127.5, 125.1, 123.8, 122.9, 122.7, 121.6, 121.4, 120.6, 120.0, 110.6, 107.8, 106.7, 93.8, 66.3, 64.5, 56.6, 54.8, 46.3, 42.5, 42.0, 37.0; HRMS: (m/z) [M+H]$^+$ calcd. for C$_{35}$H$_{36}$ClN$_4$O$_6$S$_2$, 707.1759. found 707.1761.

Seco CBI Drug Carbamate Pyridyl Disulfide—13

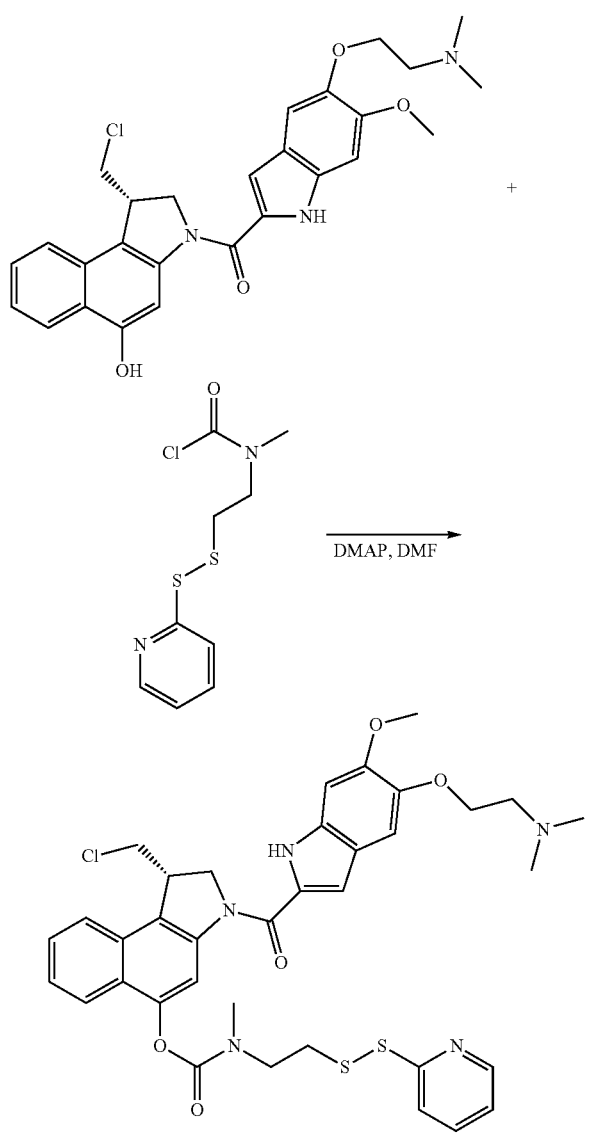

Seco CBI drug 14 (10 mg, 20 μmol, 1.0 eq), activated carbamate 17 (12 mg, 92 μmol, 4.6 eq) and DMAP (10 mg, 100 μmol, 5.0 eq) were dissolved in DMF (2 mL) and stirred for 12 h at room temperature. The reaction mixture was diluted with MeOH (2 mL) and purified over HPLC (95% A/5% B to 20% A/80% B over 20 min). Fractions containing the desired product my MS were pooled and lyophilized to yield the title compound as an off white powder (9.5 mg, 13 μmol, 65%).

$^1$H-NMR (400 MHz, MeOD-d$_4$, mixture of two rotamers) δ [ppm]=8.42-8.23 (br m, 2H), 7.96-7.73 (m, 4H), 7.60-7.37 (m, 2H), 7.32 (s, 1H), 7.35-7.24 (m, 1H), 7.16-7.14 (m, 1H), 7.04-7.03 (2s, 1H), 4.74-4.65 (m, 2H), 4.31 (t, J=4.7 Hz, 2H), 4.30-4.21 (m, 1H), 4.07-4.00 (m, 2H), 3.84-3.82 (2s, 3H), 3.87-3.62 (m, 2H), 3.60 (t, J=4.9 Hz, 2H), 3.36-3.11 (m, 5H), 3.05 (s, 6H); $^{13}$C-NMR (125 MHz, MeOD-d$_4$) δ [ppm]=161.8, 161.7, 161.1, 160.8, 157.0 156.6, 151.5, 150.6, 149.1, 144.9, 142.9, 142.8, 139.1, 134.6, 131.3, 128.8, 126.3, 124.1, 123.8, 123.7, 123.6, 122.6, 122.2, 121.5, 121.5, 112.9, 112.6, 109.5, 108.0, 107.9, 95.5, 98.4, 66.2, 58.1, 56.4, 56.3, 47.8, 44.0, 43.6, 37.5, 37.4, 35.8, 35.7; HRMS: (m/z) [M+H]$^+$ calcd. for C$_{36}$H$_{39}$ClN$_5$O$_5$S$_2$, 720.2076. found 720.2074.

Seco CBI Drug—14

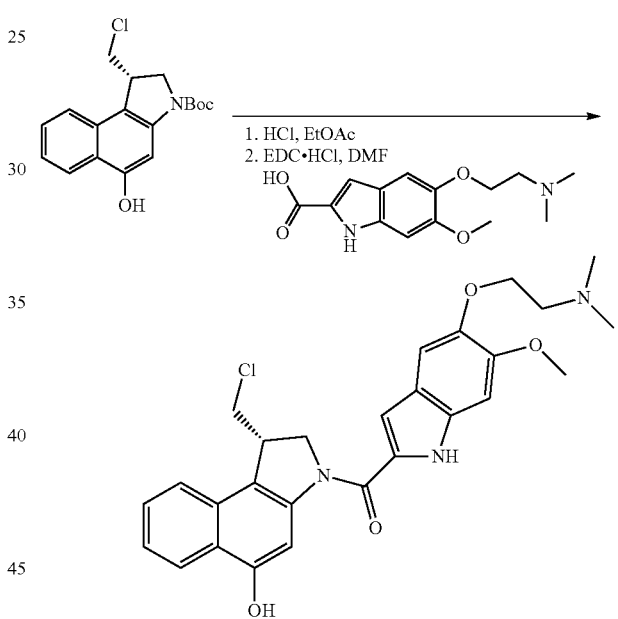

N-Boc protected seco CBI (50 mg, 150 μmol, 1.0 eq) was dissolved in 4 M HCl in dry EtOAc (5 mL) and stirred for 6 h at room temperature. The solvent was removed under reduced pressure and the residue dissolved in 3 mL DMF and cooled on ice. EDC.HCl (86 mg, 450 μmol, 3.0 eq) was added followed by indole 18 (61 mg, 220 μmol, 1.3 eq), the mixture warmed to room temperature and allowed to stir for 12 h. MeOH (3 mL) was added and the crude reaction mixture purified over HPLC (95% A/5% B to 20% A/80% B over 20 min). Fractions containing the desired product my MS were pooled and lyophilized to yield the title compound as an off-yellow powder (44.1 mg, 89.5 μmol, 60%).

$^1$H-NMR (400 MHz, MeOD-d4) δ [ppm]=8.10 (d, J=8.2 Hz, 1H), 7.77 (s, 1H), 7.61 (d, J=8.3 Hz, 1H), 7.37 (td, J=6.8, 1.2 Hz, 1H), 7.23 (td, J=6.8, 1.0 Hz, 1H), 7.15 (s, 1H), 6.91 (s, 1H), 6.87 (s, 1H), 4.49-4.38 (m, 2H), 4.13 (t, J=4.8 Hz, 2H), 3.96-3.92 (m, 1H), 3.80 (dd, J=11.2, 3.2 Hz, 1H), 3.72 (s, 3H), 3.44-3.39 (m, 3H), 2.91 (s, 6H); $^{13}$C-NMR (100 MHz, MeOD-d$_4$) δ [ppm]=173.0, 162.4, 155.8, 151.6, 144.9, 143.4, 134.6, 131.6, 130.9, 128.6, 124.6, 124.5, 123.5, 122.2, 117.0, 109.5, 107.9, 101.5, 95.5, 66.0, 58.1, 56.8, 56.3, 47.5, 43.9, 43.6; HRMS: (m/z) [M+H]$^+$ calcd. for C$_{27}$H$_{29}$ClN$_3$O$_4$, 494.1841. found 494.1843.

N1-(2-(2-(2-aminoethoxy)ethoxy)ethyl)-N4-(5-sulfamoyl-1,3,4-thiadiazol-2-yl)succinamide—25

$^1$H-NMR (400 MHz, MeOD-d$_4$) δ [ppm]=3.60 (t, J=5.0 Hz, 2H), 3.55 (m, 4H), 3.45 (t, J=5.6 Hz, 2H), 3.27 (t, J=5.6 Hz, 2H), 3.02 (t, J=5.0 Hz, 2H), 2.75 (t, J=5.6 Hz, 2H), 2.54 (t, J=6.2 Hz, 2H); $^{13}$C-NMR (100 MHz, MeOD-d$_4$) δ [ppm]=174.3, 173.0, 166.4, 163.1, 71.4, 71.3, 70.7, 67.9, 40.7, 40.3, 31.5, 30.9; HRMS: (m/z) [M+H]$^+$ calcd. for C$_{12}$H$_{23}$N$_6$O$_6$S$_2$, 411.1115. found 411.1116.

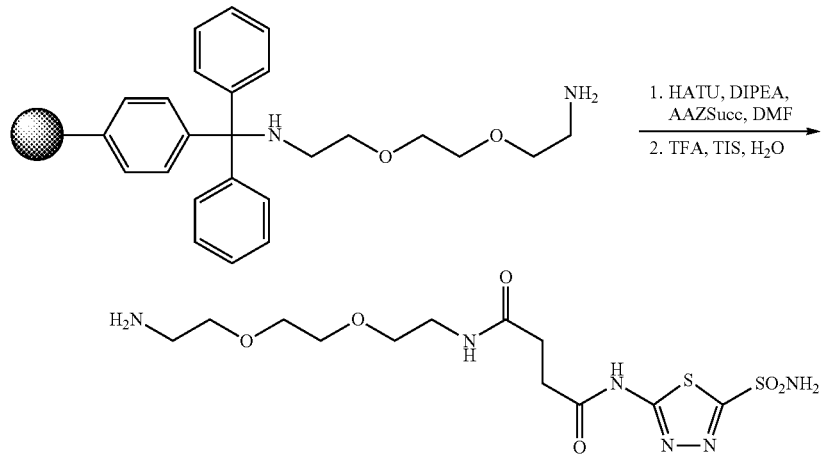

(S)-tert-butyl (2-(2-(2-(3-methyl-2-(4-(4-sulfamoylphenyl)-1H-1,2,3-triazol-1-yl)butanamido)ethoxy)ethoxy)ethyl)carbamate—26

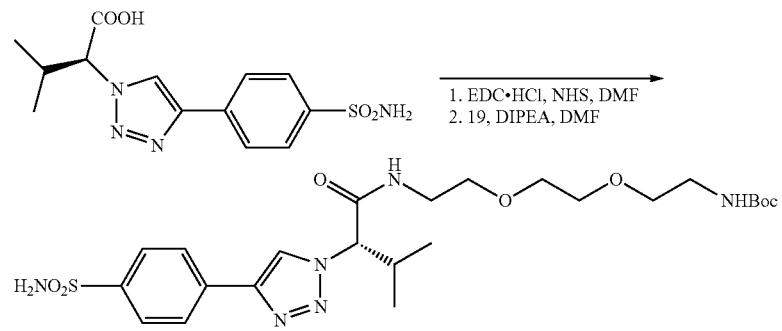

Commercially available pre-loaded O-Bis-(aminoethyl) ethylene glycol on trityl resin (500 mg, 0.3 mmol, Merck Millipore) was swollen in DMF (3×5 min×5 mL). 4-oxo-4-((5-sulfamoyl-1,3,4-thiadiazol-2-yl)amino)butanoic acid (AAZSucc, 166 mg, 0.59 mmol) and HATU (228 mg, 0.60 mmol) were dissolved in DMF (5 mL) and DIPEA (200 μL, 1.2 mmol) was added. The solution was immediately reacted with the resin for 30 min at room temperature. The resin was washed with DMF (6×1 min×5 mL), DCM (3×1 min×5 mL) and cleaved with 95% TFA/2.5% H$_2$O/2.5% triisopropylsilane (TIS, 5 mL total volume) for 1 h at room temperature and washed with TFA (1×1 min×5 mL). The combined cleavage and wash solutions were poured into cold Et$_2$O (40 mL), the precipitate collected by centrifugation and purified over reversed-phase HPLC (95% A/5% B to 20% A/80% B over 20 min). Fractions containing the desired product by MS were pooled and lyophilized to give the product as a white powder (48 mg, 0.12 mmol, 39%).

To a solution of 27 (64 mg, 0.20 mmol) in DMF (2 mL) was added NHS (25 mg, 0.22 mmol) and EDC.HCl (42 mg, 0.22 mmol) and the mixture was stirred for 1 h at room temperature. A solution of 19 (54 mg, 0.22 mmol) and DIPEA (110 μL, 0.67 mmol) in DMF (1 mL) was added and the reaction stirred for 1 h at room temperature. The solvent was removed under reduced pressure, the residue dissolved in DCM (5 mL) and the solution washed with H$_2$O (1×5 mL), brine (1×5 mL), dried over Na$_2$SO$_4$ and the solvent removed under reduced pressure. Purification by flash column chromatography over silica (EtOAc) gave the product as a white solid (63 mg, 0.11 mmol, 57%).

$^1$H-NMR (400 MHz, MeOD-d$_4$) δ [ppm]=8.75 (br m, 1H), 8.69 (s, 1H), 8.05 (d, J=6.6 Hz, 2H), 7.98 (d, J=6.6 Hz, 2H), 3.61-3.56 (m, 6H), 3.53-3.37 (m, 4H), 3.22 (t, J=5.6 Hz, 2H), 2.65-2.56 (m, 1H), 1.44 (s, 9H), 1.12 (d, J=6.7 Hz, 3H), 0.84 (d, J=6.6 Hz, 3H); $^{13}$C-NMR (100 MHz, MeOD-d$_4$) δ [ppm]=170.0, 158.5, 147.5, 144.5, 135.5, 128.0, 127.0, 122.3, 80.1, 71.7, 71.6, 71.3, 71.1, 70.3, 41.2, 40.7, 33.0, 28.8, 19.6, 19.2; HRMS: (m/z) [M+H]⁺ calcd. for $C_{24}H_{38}N_6NaO_7S$, 577.2415; meas. 577.2415.

(S)-3-methyl-2-(4-(4-sulfamoylphenyl)-1H-1,2,3-triazol-1-yl)butanoic acid—27

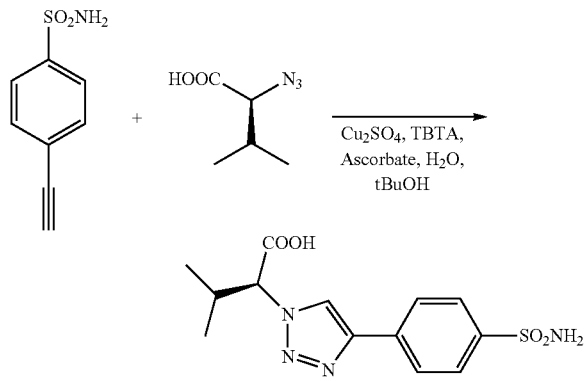

Ethynyl benzene sulfonamide (54 mg, 0.3 mmol), azido valine 20 (42 mg, 0.3 mmol) and tris-(benzyltriazolylmethyl)amine (TBTA, 0.3 mg, cat.) were dissolved in a mixture of tBuOH (3.7 mL), a 0.04 M $CuSO_4$ solution in PBS pH 7.4 (2.0 mL) and a 0.1 M sodium ascorbate solution in PBS pH 7.4 (1.7 mL) and stirred for 12 h at room temperature. All solvents had previously been de-gassed and flushed with Ar. The reaction was poured onto 25 mL $H_2O$ acidified to pH 2.0 and the mixture extracted with EtOAc (4×20 mL), the pooled organic phases washed with brine and dried over $MgSO_4$. The solvent was removed under vacuum and the residue purified over silica (20% MeOH in DCM with 0.1% $Et_3N$) to yield the product as a white solid (70 mg, 72%).

¹H-NMR (400 MHz, DMSO-d₆) δ [ppm]=8.86 (s, 1H), 8.10 (d, J=8.5 Hz, 2H), 7.90 (d, J=8.5 Hz, 2H), 7.39 (s, 1H), 5.24 (d, J=8.0 Hz, 1H), 2.64-2.55 (m, 1H), 1.00 (d, J=6.7 Hz, 3H), 0.88 (d, J=6.7 Hz); ¹³C-NMR (100 MHz, DMSO-d₆) δ [ppm]=169.6, 145.0, 143.2, 133.7, 126.3, 125.4, 122.6, 68.3, 30.4, 19.0, 18.3; HRMS: (m/z) [M+H]⁺ calcd. for $C_{13}H_{15}N_4Na_2O_4S$, 369.0604. found 369.0609.

Tert-butyl (2-(2-(2-((4-chloro-6-((4-sulfamoylphenyl)amino)-1,3,5-triazin-2-yl)amino)ethoxy)ethoxy)ethyl)carbamate—28

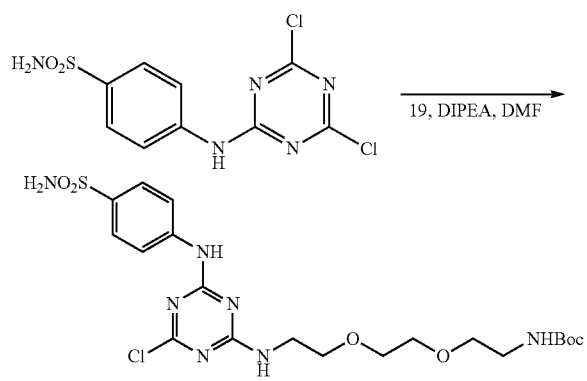

21 (160 mg, 0.64 mmol), 14 (204 mg, 0.64 mmol) and DIPEA (105 µL, 0.64 mmol) were dissolved in DMF (5 mL) and stirred for 3 h at room temperature. The reaction mixture was diluted with $H_2O$ (15 mL) and extracted with EtOAc (3×10 mL). The combined organic fractions were washed with 10% w/v aq. LiCl solution (1×10 mL), brine (1×10 mL) and dried over $Na_2SO_4$. The solvent was removed under reduced pressure and the residue purified over silica (EtOAc) to give the product as a white solid (239 mg, 66%).

¹H-NMR (400 MHz, DMSO-d₆, mixture of two rotamers) δ [ppm]=10.39-10.30 (m, 1H), 8.27 (br s, 1H), 7.93 (d, J=8.1 Hz, 1H), 7.85 (d, J=8.1 Hz, 1H), 7.74 (m, 2H), 7.25 (s, 1H), 7.23 (s, 1H), 6.74-6.73 (m, 1H), 3.57-3.32 (m, 10H), 3.05 (m, 2H), 1.37 (s, 9H); ¹³C-NMR (125 MHz, DMSO-d₆, mixture of two rotamers, several signals overlap) δ [ppm]=169.0, 168.5, 166.0, 165.9, 164.2, 163.7, 156.0, 142.6, 142.5, 138.3, 138.2, 127.1, 126.8, 120.0, 119.8, 78.1, 70.1, 70.0, 69.9, 69.6, 69.1, 68.8, 67.1, 39.0, 28.7; HRMS: (m/z) [M+H]⁺ calcd. for $C_{20}H_{30}ClN_7NaO_6S$, 554.1559. found 554.1555.

(E)-tert-butyl (2-(2-(2-(3-((4-((4-sulfamoylphenyl)diazenyl)phenyl)amino) propanamido)ethoxy)ethoxy)ethyl)carbamate—29

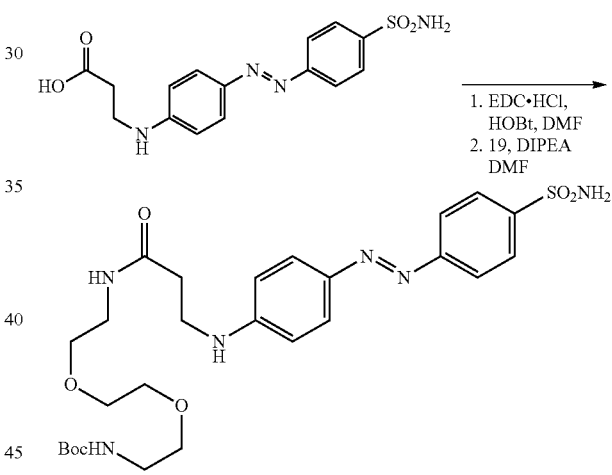

To 30 (20 mg, 57 µmol) dissolved in DMF (1 mL) was added HOBt (8.7 mg, 57 µmol) followed by EDC.HCl (12.2 mg, 64 µmol). After stirring the reaction for 1 h at room temperature a solution of 19 (15.8 mg, 64 mmol) and DIPEA (20 µL, 122 µmol) in DMF (0.5 mL) was added. The mixture was stirred for 1 h at room temperature, diluted with MeOH (1.5 mL) and purified over reversed-phase HPLC (80% A/20% B to 20% A/80% B over 20 min). Fractions containing the desired product by MS were pooled and lyophilized to give the product as an orange powder (26 mg, 45 mmol, 79%).

¹H-NMR (400 MHz, MeOD-d₄) δ [ppm]=8.02 (d, J=8.8 Hz, 2H), 7.91 (d, J=8.8 Hz, 2H), 7.83 (d, J=9.0 Hz, 2H), 7.76 (d, J=9 Hz, 2H), 3.60 (s, 4H), 3.58-3.49 (m, 6H), 3.40 (t, J=5.5 Hz, 2H), 3.23-3.20 (m, 2H), 2.56 (t, J=6.7 Hz, 2H), 1.45 (s, 9H); ¹³C-NMR (125 MHz, MeOD-d₄) δ [ppm]=170.8, 156.1, 154.7, 153.2, 144.3, 143.3, 127.4, 126.3, 122.4, 112.2, 78.1, 70.0, 69.9, 69.6, 69.5, 39.1, 35.4, 28.7; HRMS: (m/z) [M+H]⁺ calcd. for $C_{26}H_{38}N_6NaO_7S$, 601.2415. found 601.2416.

(E)-3-((4-((4-sulfamoylphenyl)diazenyl)phenyl)amino)propanoic acid—30

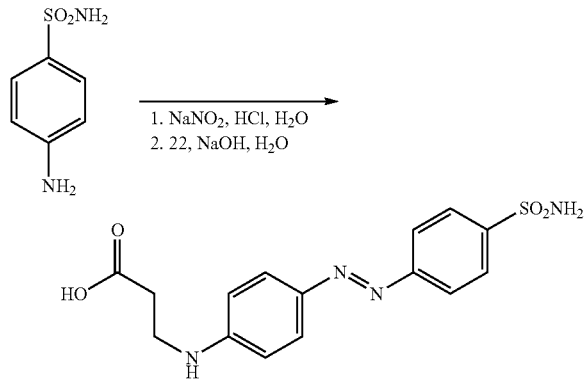

Sulfanilamide (85 mg, 0.49 mmol) was dissolved in 40% aq. HCl (1.3 mL) and cooled to 0° C. A solution of NaNO$_2$ in water (300 µL) was added drop-wise over 5 min and the reaction stirred on ice for 15 min. The yellowish solution was slowly added to a suspension of 22 (129 mg, 0.37 mmol) in 10M aq. NaOH (1 mL) and DMF (1 mL) and stirred for 2 h at room temperature. The dark red solution was acidified with 6 N HCl, extracted with EtOAc (6×10 mL), dried over Na$_2$SO$_4$ and the solvent removed under reduced pressure. Recrystallization of the dark red residue gave the product as a red solid (32 mg, 25%). $^1$H-NMR (400 MHz, DMSO-d$_6$) δ [ppm]=7.95 (d, J=8.6 Hz, 2H), 7.88 (d, J=8.6 Hz, 2H), 7.77 (d, J=8.9 Hz, 2H), 7.44 (s, 2H), 9.94 (br s, 1H), 6.74 (d, J=8.9 Hz, 2H), 3.40 (t, J=6.4 Hz, 2H), 2.56 (t, J=6.4 Hz, 2H); $^{13}$C-NMR (100 MHz, DMSO-d$_6$) δ [ppm]=172.9, 154.1, 152.6, 143.8, 142.9, 126.8, 125.8, 121.9, 111.7, 38.4, 33.4; HRMS: (m/z) [M+H]$^+$ calcd. for C$_{15}$H$_{17}$N$_4$O$_4$S, 349.0965. found 349.0967.

Tert-butyl (2-(2-(2-(4-sulfamoylbenzamido)ethoxy)ethoxy)ethyl)carbamate—31

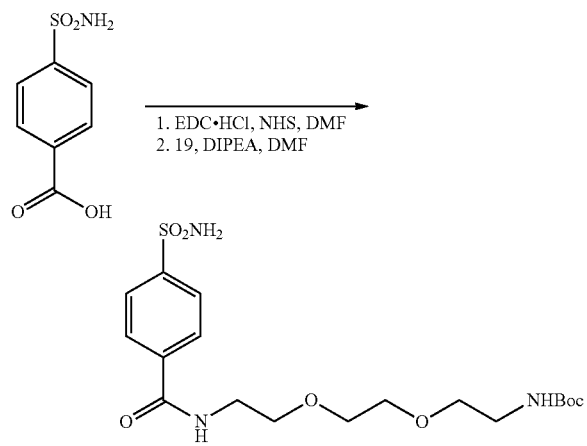

To a solution of 4-carboxybenzenesulfonamide (46 mg, 0.23 mmol) in MeCN (2 mL) was added NHS (29 mg, 0.25 mmol) followed by EDC.HCl (48 mg, 0.25 mmol). After stirring for 4 h at room temperature more EDC.HCl (24 mg, 0.13 mmol) was added and the reaction stirred for a further 1 h at room temperature. A solution of 19 (52 mg, 0.21 mmol) and DIPEA (140 µL, 0.85 mmol) in DMF (1 mL) was added. After stirring for 10 h at room temperature, the reaction was filtered through a pad of silica eluting with EtOAc, the solvent removed under reduced pressure and the residue purified over silica (EtOAc to 10% MeOH in EtOAc) to give the product as a white solid (61 mg, 0.14 mmol, 67%).

$^1$H-NMR (400 MHz, DMSO-d$_6$) δ [ppm]=8.71 (br m, 1H), 8.00 (d, J=8.1 Hz, 2H), 7.90 (d, J=8.1 Hz, 2H), 7.46 (br s, 2H), 6.76 (br m, 1H), 3.55-3.33 (m, 10H), 3.06-3.05 (m, 2H), 1.37 (s, 9H); $^{13}$C-NMR (125 MHz, DMSO-d$_6$) δ [ppm]=165.8, 156.1, 146.7, 137.7, 128.3, 126.1, 78.1, 70.0, 69.9, 69.6, 69.2, 67.1, 39.1, 28.7; HRMS: (m/z) [M+H]$^+$ calcd. for C$_{18}$H$_{29}$N$_3$NaO$_7$S, 454.1618. found 454.1623.

Propagation of Errors

During data analysis standard deviations were propagated according to formula (1) as recommended by the National Institute of Standards and Technology.[2]

$$\sigma_f = \sqrt{\sum_{i=1...n}\left(\frac{\partial f}{\partial x_i}\sigma_i\right)^2} \quad (1)$$

Where $f=f(x_1, x_2, \ldots x_n)$, $\sigma_f$ is the standard deviation of function $f$ and σ is the standard deviation of $x_i$.

Determination of Ligand K$_D$ by Fluorescence Polarization Measurement

Fluorescently labeled ligands (2 mg) were dissolved in DMSO (100 µL) and diluted 1:2000 into PBS pH 7.4 to determine the stock's concentration by absorbance measurement at 495 nm ($\epsilon_{495}$=72,000 M$^{-1}$ cm$^{-1}$). Recombinant CAIX was expressed as described previously[3], dialyzed against assay buffer (50 mM tris(hydroxymethyl)aminomethane [TIRS] pH 7.4 containing 1 mM ZnSO$_4$) at 4° C. overnight and the protein concentration determined by absorbance measurement at 280 nm ($\epsilon_{280}$=35,075 M$^{-1}$ cm$^{-1}$).

In a black 384-well plate in assay buffer (30 µL) fluorescently labeled ligands (5 nM from appropriately diluted DMSO stocks, final DMSO content adjusted to 0.001%) were incubated with increasing concentrations of recombinant carbonic anhydrase IX (4.6 µM to 140 pM in steps of 1:2) for 1 h at room temperature. The fluorescence polarization (FP) was measured on a Spectra Max Paradigm multimode plate reader (Molecular Devices). Experiments were performed in triplicate, mean FP values divided by the top-plateau signal and the fractional FP value fit to equation (2) using KaleidaGraph 4.0 (Synergy Software).

$$FP=([P]_0+[L]_0+K_D)-\sqrt{([P]_0+[L]_0+K_D)^2-4[P]_0[L]_0} \quad (2)$$

Where FP is the fractional fluorescence polarization, [P]$_0$ the total protein concentration, [L]$_0$ the total concentration of the fluorescently labeled ligand and K$_D$ the dissociation constant in nM.

Measured values of K$_D$ for fluorophore-linker-ligand complexes were: 1a 12.6±1.0 nM; 2a 18.1±1.3 nM; 3a 46.8±1.2 nM; 5a 218±9 nM. 4a could not be determined due to its dark quenching properties. Reference example 6a did not bind to the CAIX. Thus, the acetazolamide (AAZ) ligand of 1a appears to be the most promising.

Competitive Fluorescence Polarization Measurement of $K_D$

In a black 384-well plate in assay buffer (see above, 40 µL) fluorescently labeled probe 1a (5 nM from appropriately diluted DMSO stocks) and recombinant carbonic anhydrase IX (25 nM) were incubated with increasing concentrations of unlabeled ligand (2.5 µM to 76 pM in steps of 1:2) for 1 h at room temperature. The FP was measured on a Spectra Max Paradigm multimode plate reader (Molecular Devices). Experiments were performed in triplicate and data analyzed as described by Wang and co-workers.[4]

This method was used to determine $K_D$ for the unlabeled drug-linker-ligand conjugates prepared as shown in FIG. 2. $K_D$ values are given in brackets±standard errors of fit. The following values of $K_D$ were determined: 7a 7.3±0.5 nM; 8a 40.3±2.6 nM; 9a 26.5±2.5 nM. The $K_D$ for 7b was >1 µM. Thus, targeted conjugates 7a, 8a and 9a retain binding affinity for recombinant CAIX in vitro whereas untargeted controls 7b, 8b and 9b do not exhibit strong binding.

Cell Culture

SKRC52 and HEK cells were maintained in RPMI medium (Invitrogen) supplemented with 10% fetal calf serum (FCS, Invitrogen) and antibiotic-antimycotic (AA, Invitrogen) at 37° C. and 5% $CO_2$. A549 cells were maintained in F-12K medium (Invitrogen) supplemented with 10% FCS (Invitrogen) and AA (Invitrogen) at 37° C. and 5% $CO_2$. For passaging, cells were detached using trypsin with ethylenediaminetetraacetic acid (EDTA) 0.05% (Invitrogen) when reaching 90% confluence and re-seeded at a dilution of 1:10.

Cell surface expression of CAIX on different cell lines used in this study were analyzed by flow cytometry using aCAIX (a Santa Cruz biotechnology polyclonal rabbit anti human CAIX antibody). A suitably labeled anti rabbit IgG antibody was used for detection. It was found that SKRC52 cells constitutively express high levels of CAIX. In contrast, A549 cells express only very low levels of CAIX under normoxic conditions. Since they maintain strong attachments to culture plates, we used these cells as negative controls in experiments requiring multiple washing steps of attached cells. It was found that HEK cells do not express detectable levels of CAIX under normoxic culture conditions. They can easily be detached from culture plates with EDTA and were thus used as negative controls in most flow cytometry experiments.

In Vitro Cytotoxicity Assay

SKRC52 or A549 cells were seeded in 96-well plates in their appropriate culture medium (100 µL) at a density of 5000 cells per well and allowed to grow for 24 h. The medium was replaced with medium containing different concentrations of test substance (100 µL, 300 nM-15 pM in 1:3 dilution steps) and plates were either:
(a) incubated for 72 hours in the presence of the toxic substance, or
(b) incubated for 1 h under standard culture conditions, followed by removal of the medium containing the toxic substance, gently washing the cells fresh medium once and adding new medium (100 µL) and incubating for 72 h under culture conditions.

MTS cell viability dye (20 µL, Promega) was added, the plates were incubated for 1 h under culture conditions and the absorbance at 490 nm measured on a Spectra Max Paradigm multimode plate reader (Molecular Devices). Experiments were performed in triplicate and average cell viability calculated as measured background corrected absorbance divided by the absorbance of untreated control wells. $EC_{50}$ values were determined by fitting data to the four-parameter logistic equation.

The $EC_{50}$ values found for various cytotoxic compounds and conjugates against CAIX expressing SKRC52 cells were as follows:
Condition (a): 14 55±5 pM; 7a 21±7 pM; 7b 96±33 pM; DM1 4.3±0.5 pM; DM1SMe 0.5±0.0 pM; 9a 41±9 pM; 9b 31±6 pM.
Condition (b): 14 1.0±0.1 nM; 7a 0.7±0.1 nM; 7b 1.4±0.3 nM; DM1 45±10 nM; DM1SMe 5.8±1.1 nM; 9a *; 9b *.

These results show that the conjugates 7a and 9a according to the invention release the cytotoxic drug moiety in effective amounts over 72 hours under Condition (a). However, DM1 conjugates 9a and 9b did not exhibit sufficient cytotoxicity for measurement of $EC_{50}$ values in the 1 hour timescale of Condition (b) at concentrations up to 300 nM, reflecting the relatively long half-life of these conjugates as further discussed below.

Ligand Binding Analysis by Flow Cytometry

Cells were detached from culture plates using a 50 mM EDTA solution in phosphate buffered saline (PBS) pH 7.4, counted and suspended to a final concentration of $1.5 \times 10^6$ cells $mL^{-1}$ in a 1% v/v solution of FCS in PBS pH 7.4. Aliquots of $3 \times 10^5$ cells (200 µL) were spun down and resuspended in solutions of IRDye750 (Licor) labeled ligands (30 nM) in a 1% v/v solution of FCS in PBS pH 7.4 (200 µL) and incubated on ice for 1 h. Cells were washed once with 200 µL 1% v/v solution of FCS in PBS pH 7.4 (200 µL), spun down, resuspended in 1% v/v solution of FCS in PBS pH 7.4 (300 µL) and analyzed on a FACS Canto flow cytometer (BD Bioscience). FlowJo Version 8.7 (Treestar) was used for data analysis and visualization. Results were as follows:

(1) Flow cytometry analysis of binding of ligand-IRDye750 conjugates 1c-6c (FIG. 1) to CAIX expressing SKRC52 cells.

Cells were detached with EDTA, treated with 30 nM dye conjugate for 1 h at 0° C., washed and analyzed. Only 1c binds strongly enough to result in a strong fluorescence shift after washing of cells. Given their higher $K_D$, conjugates 2c-5c probably dissociate too quickly to be detected. Conjugate 6c, which lacks a ligand for CAIX, only shows little residual binding.

(2) Flow cytometry analysis of binding of ligand-IRDye750 conjugates 1c-6c (FIG. 1) to CAIX negative HEK cells.

Cells were detached with EDTA, treated with 30 nM dye conjugate for 1 h at 0° C., washed and analyzed. In the absence of a specific binding interaction, there is little difference between cells treated with CAIX ligand-dye conjugates and untreated cells.

Flow cytometry analysis of binding of ligand-Alexa546 conjugates 1b and 6b to (a) CAIX expressing SKRC52 and (b) HEK cells lacking CAIX on their cell surface.

Cells were detached with EDTA, treated with 30 nM dye conjugate for 1 h at 0° C., washed and analyzed. (a) Only the conjugate bearing a ligand for CAIX can bring about an increase in fluorescence intensity. The conjugate lacking the ligand does not give rise to a shift relative to untreated cells. (b) As expected in the absence of a cell surface receptor none of the conjugates can bring about a shift in fluorescence intensity to the right.

Ligand Internalization Analysis by Flow Cytometry

SKRC52 or A549 cells were seeded in 6-well plates in their appropriate culture medium (2 mL) at a density of $1.5 \times 10^5$ cells per well and allowed to grow for 24 h under culture conditions. The medium was replaced with medium containing IRDye750 (Licor) labeled probes 1c or 6c (2 mL, 30 nM) and plates incubated for 1, 2 or 4 h under standard culture conditions. After washing with PBS pH 7.4 (2×2 mL), Trypsin-EDTA 0.05% (500 µL, Invitrogen) was added and plates incubated under standard culture conditions for 15 min Medium (500 µL) was added, cells pelleted and resuspended in PBS pH 7.4 containing 1% v/v FCS (150 µL). After incubating for 15 min on ice, cells were labeled for 30 min on ice with rabbit anti human CAIX IgG (1:100, Santa Cruz) in PBS pH 7.4 containing 1% FCS (150 µL), washed with PBS pH 7.4 containing 1% FCS (2×150 µL) and labeled for 30 min on ice with goat anti rabbit IgG Alexa488 conjugate (1:100, Invitrogen) in PBS pH 7.4 containing 1% FCS (150 µL). After washing with PBS pH 7.4 containing 1% FCS (2×150 µL), cells were pelleted and resuspended in PBS pH 7.4 containing 1% v/v FCS and propidium iodide (300 µL, 1 µg mL$^{-1}$, Invitrogen) and analyzed on a FACS Canto flow cytometer (BD Bioscience). FlowJo Version 8.7 (Treestar) was used for data analysis and visualization. To inhibit uptake mechanisms, cells were pre-incubated with medium containing 0.2% $NaN_3$ for 1 h and the $NaN_3$ concentration maintained throughout the entire experiment. Alternatively, all steps were performed at 0° C. or an excess of AAZ (100 µM) was added to the culture medium.

CAIX positive SKRC52 cells attached to culture plates were incubated with medium containing 30 nM 1c for 1 h at 37° C. Detachment with trypsin resulted in cells with higher fluorescence intensity than cells treated with non-binding conjugate 6c or untreated cells. b) Aliquots of the same cells which had been treated with 1c and detached with trypsin were stained with an anti CAIX antibody (aCAIX AB) followed by an Alexa488 labeled secondary antibody (2° AB) at 0° C. which upon flow cytometry analysis gave a superimposable histogram to cells treated with secondary antibody only. We concluded that trypsin treatment had removed all surface bound CAIX and the fluorescence shift of 1c labeled cells in a) must come from internalized conjugate. Cells detached from solid support using EDTA and stained as before gave rise to a 10× shift in fluorescence intensity to the right compared to baseline giving us confidence that CAIX detection by FCAS did indeed work.

To further support the claim that we were observing active uptake processes, we decided to repeat the experiment under conditions inhibiting uptake. SKRC52 cells were pre-treated with medium containing 0.2% w/v $NaN_3$ for 1 h before incubation with 30 nM 1c and 0.2% w/v $NaN_3$ at 37° C. for 1 h. $NaN_3$ is known to be an inhibitor of active uptake processes[1] and indeed fluorescent signal was shifted to baseline. The same effect was achieved when incubating with 1c in the presence of excess AAZ as a competitive ligand or when incubating at 0° C., which also inhibits active uptake processes.

Extending the incubation time with 30 nM 1c at 37° C. from 1 h to 2 h and 4 h we did not see a markedly increased signal. We thus concluded that although some internalization takes place, it is inefficient over time.

Finally, active uptake of CAIX binding conjugate 1c into CAIX negative A549 cells was tested as above. Since no shift in fluorescence intensity over baseline was observed, it was concluded that 1c was not taken up into A549 cells. This is expected in the absence of a cell surface receptor for 1c.

Ligand Internalization Analysis by Confocal Microscopy

SKRC52 cells were seeded into 4-well cover slip chamber plates (Sarstedt) at a density of $10^4$ cells per well in RPMI medium (1 mL, Invitrogen) supplemented with 10% FCS, AA and 4-(2-hydroxyethyl)-1-piperazineethanesulfonic acid (HEPES, 10 mM) and allowed to grow for 24 h under standard culture conditions. The medium was replaced with medium containing 1b or 6b (30 nM), after 1 h Hoechst 33342 nuclear dye (Invitrogen) was added and randomly selected colonies imaged on an Axiovert 200M confocal microscope (Zeiss).

Stability Determination by Mass Spectrometry

Targeted carbonate or carbamate 7a or 8a (30 µg) was dissolved in PBS pH 7.4 (1.5 mL) and incubated at 37° C. under gentle agitation. Aliquots (100 µL) were removed at different time points and diluted 1:1 with an internal standard of etodolac (TCI Chemicals) in MeOH (20 µg mL$^{-1}$). Small molecules were separated from salts using an Oasis WAX online sample preparation column (Waters) on an Alliance HT separation module (50 µL injections, 0.3 mL min$^{-1}$ 0.1% aq. HCOOH for 3 min followed by 0.3 mL min$^{-1}$ MeCN for 7 min, Waters) and analyzed by mass spectrometry/mass spectrometry (MS/MS) on a Quattro API spectrometer (Waters) monitoring appropriate multiple reaction monitoring (MRM) transitions for 8a, 8b and etodolac as standard. Measurements were performed in triplicate, peaks integrated and the fraction of intact test compounds calculated as fraction of signal at time t divided by signal at time zero. Since signals due to etodolac were constant over time a further correction using the internal standard as reference was omitted. For stability measures in mouse serum, compounds were dissolved in freshly thawed mouse plasma (Invitrogen), aliquots taken at different time points and diluted with an equal volume of MeCN. After vigorous vortexing for 1 min, protein precipitate was spun down and the supernatant analyzed as above.

Half lives of 7a and 8a in mouse plasma at 37° C. as determined by mass spectrometry (MS/MS) were 43 minutes and 61 minutes, respectively. Errors were <1 min.

Stability Determination by High-Performance Liquid Chromatography (HPLC)

Targeted DM1 conjugate 9a (230 µg, 140 nmol) was dissolved in PBS pH 7.4 (1 mL) and incubated at 37° C. under gentle agitation. Aliquots (100 µL) were removed at different time points and diluted 1:1 with an internal standard solution of etodolac (TCI Chemicals) in MeCN (20 µg mL$^{-1}$). Water (600 µL) was added and aliquots of this mixture (50 µL) analyzed over a Syngergi RP Polar column (150×4.6 mm, 4 µm, Phenomenex) on an Alliance HT separation module (1 mL min$^{-1}$ 5% MeCN in 0.1% aqueous TFA to 100% MeCN over 20 min, Waters). Analytes were detected using a Water 2996 photo array UV/VIS detector (Waters). Measurements were performed in triplicate, peaks integrated and the fraction of intact test compounds calculated as fraction of signal at time t divided by signal at time zero. Since signals due to etodolac were constant over time a further correction using the internal standard as reference was omitted. For stability measures in mouse serum, compounds were dissolved in freshly thawed mouse plasma (Invitrogen), aliquots taken at different time points and diluted with an equal volume of MeCN. After vigorous vortexing for 1 min, protein precipitate was spun down and the supernatant analyzed as above.

Figure 8:
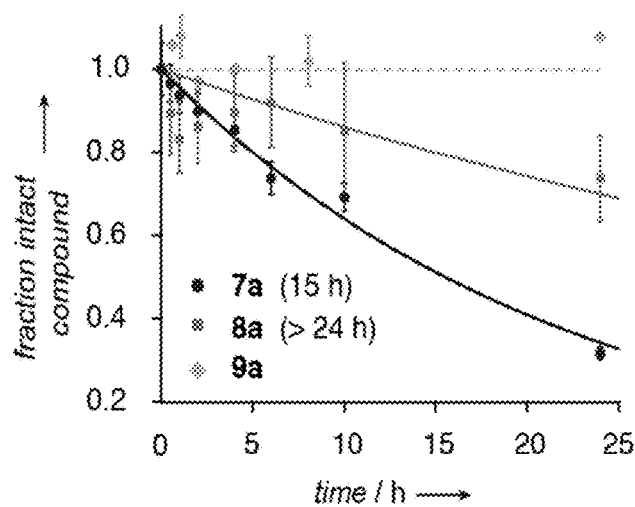
FIG. 8 shows hydrolytic stability of drug conjugates 7a, 8a and 9a in PBS at pH 7.4 and 37 C as determined by liquid chromatography-mass spectrometry/mass spectrometry (7a and 8a) and high-performance liquid chromatography (9a)

As expected, the carbonate 7a ($t_{1/2}$=15 h) was less stable in PBS at 37° C. than the carbamate 8a ($t_{1/2}$>24 h). No decomposition was observed for the DM1 conjugate 9a under the same conditions (FIG. 8). The stability of 7a and 8a was reduced in mouse serum in vitro ($t_{1/2}$=43 and 61 min respectively), but occurred in a time range compatible with the preferential accumulation of the AAZ conjugates at the tumor site. The DM1 conjugate 9a was significantly more stable in mouse serum ($t_{1/2}$=20 h).

Animal Studies

All animal experiments were conducted in accordance with Swiss animal welfare laws and regulations under the license number 42/2012 granted by Veterinaeramt des Kanton Zurich.

Implantation of Subcutaneous SKRC52 Tumors

SKRC52 cells were grown to 80% confluence and detached with Trypsin-EDTA 0.05% (Invitrogen). Cells were washed with PBS pH 7.4 once, counted and resuspended in PBS to a final concentration of $6.7 \times 10^7$ cells $mL^{-1}$. Athymic balb/c nu/nu mice, 8-10 weeks of age (Charles River) were anesthetized with isofluorane and aliquots of $1 \times 10^7$ cells (150 µL of suspension) injected subcutaneously into their lower back.

IVIS Imaging

Mice bearing subcutaneous SKRC52 tumors (200-300 $mm^3$ in size) were injected intravenously with IRDye750 (Licor) labeled CAIX ligands 1c-6c (up to 10 nmol) dissolved in 5% v/v DMSO in PBS pH 7.4 (150 µL). Mice were anesthetized with isoflurane and in vivo fluorescence images acquired on an IVIS Spectrum imaging system (Xenogen, exposure is, binning factor 8, excitation at 745 nm, emission filter at 800 nm, f number 2, field of view 13.1). Images were taken after 1 h, 2 h, 4 h, 8 h and 12 h and 24 h. Food and water was given ad libitum during that period.

Near infrared images of SKRC52 were obtained from xenograft bearing mice 1-12 h after intravenous injection of 3 nmol ligand-IRDye750 conjugates 1c-5c and untargeted conjugate 6c as negative control (see FIG. 1 for structures). Only the AAZ conjugate 1c gave good tumor to background contrast and was thus selected as a basis for further development of a targeted conjugate.

Already 1 h after the intravenous injection of 1 nmol 1c the tumor could clearly be seen against background. The injection of 3 nmol gives a stronger and longer lasting signal with good tumor to background contrast at early time points and was thus used for further imaging studies. A dose of 10 nmol saturates the fluorescence detector with the parameters used at early time points but leads to an even longer lasting signal.

After administration of 2c the tumor was barely visible; all other conjugates did not reach the tumor in levels above background fluorescence. Untargeted conjugate 6c also does not reach the tumor and is also cleared faster from the animal than ligand-IRDye750 conjugates.

Mice were subsequently sacrificed by cervical dislocation. Heart, lung, kidney, liver, spleen, a section of the intestine (100-150 mg), skeletal muscle (100-150 mg) and the tumor were extracted and imaged individually using above parameters. Qualitatively, a decrease in targeting performance from 1c to 5c could be observed and very little tumor or organ accumulation from untargeted conjugate 6c. This confirms that binding affinity of the targeting ligand for CAIX is an important determinant for accumulation inside the tumor and in vitro profiling of dye conjugates by FP and flow cytometry has predictive value for in vivo targeting performance.

Biodistribution Analysis

Mice (groups of 3 per time point and compound) bearing subcutaneous SKRC52 tumors (200-300 $mm^3$ in size) were injected intravenously with IRDye750 (Licor) labeled probes 1c or 6c (3 nmol) dissolved in 5% v/v DMSO in PBS pH 7.4 (150 µL). After 1 h, 2 h or 4 h animals were sacrificed, organs extracted as above, cut into small pieces, weighed and suspended in 1:1 w/v organ homogenization buffer containing EDTA (40 mM), proteinase K (6 mg/ml), Triton X-100 (1.6 µl/ml) and trace amounts of DNase 1 in PBS pH 7.4 (100 µL per 100 mg of tissue). The suspension was homogenized on a TissueLyser organ homogenizer (Quiagen, 25 Hz, 10 min), incubated for 2 h at room temperature and 100 µL of the homogenate transferred to a black 96-well plate. A standard dilution series of 1c in homogenization buffer (750 nM-47 nM, 25-1.5% ID $g^{-1}$ in steps of 1:2) was spotted alongside the organ samples in triplicate. Fluorescent images of plates were recorded on an IVIS Spectrum imaging system (Xenogen, parameters as above) and analyzed using Living Image software version 4.3.1 (Caliper Life Science) using the built-in region of interest (ROI) tools. Dye concentrations in organ samples in % of injected dose per gram of tissue (% ID $g^{-1}$) were inferred from fluorescence intensities originating from the corresponding well by comparison with the standard dilution series.

Figure 3:
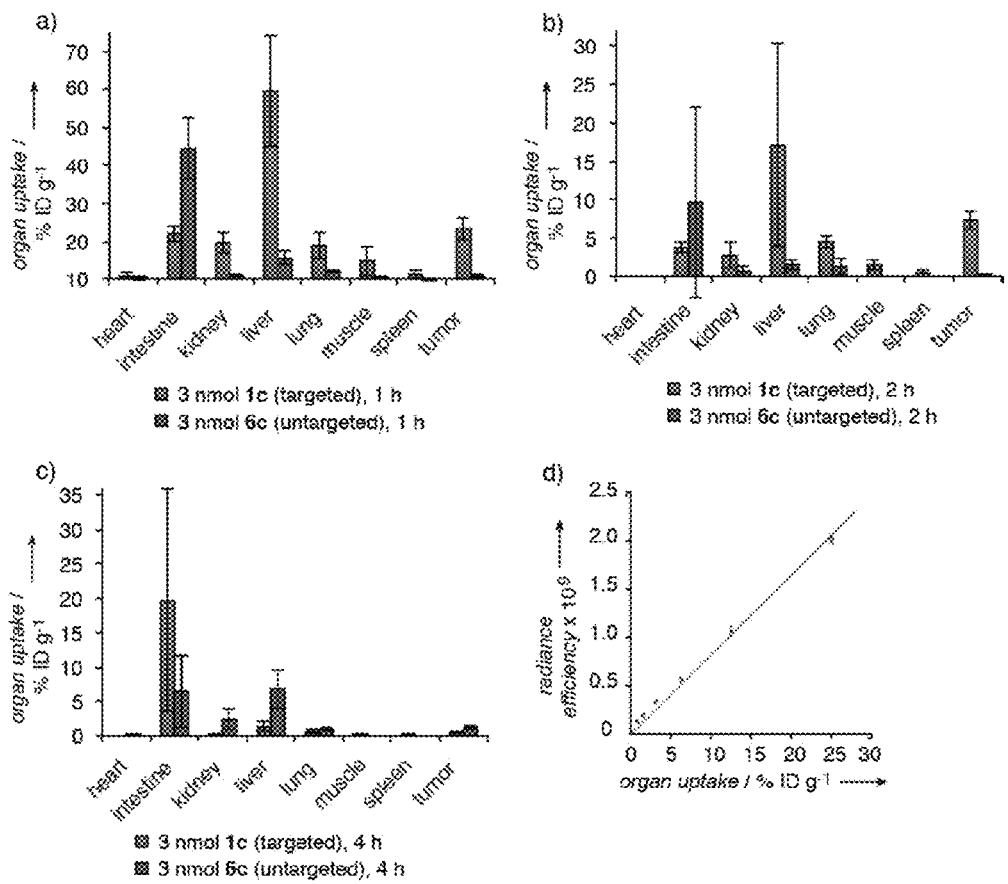
FIG. 3 shows fluorescence measurements of organ uptake of ligand-linker-dye conjugate using a ligand of the type used in the conjugates of the present invention, compared to uptake into the same organs of an untargeted conjugate.
Figure 4:
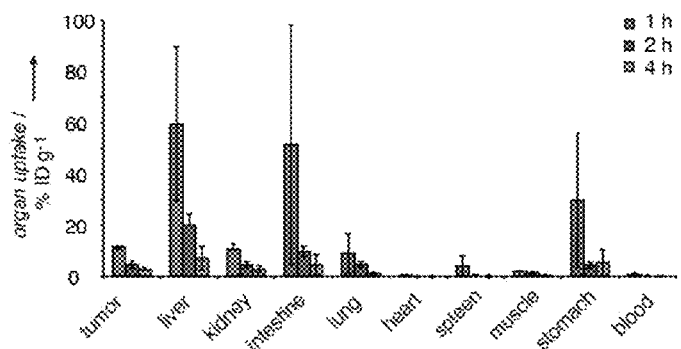
FIG. 4 shows fluorescence measurements of organ uptake of ligand-linker-dye conjugate using a ligand of the type used in the conjugates of the present invention at 1 hour, 2 hours and 4 hours after administration of the conjugate.

The results are shown graphically in FIGS. 3 and 4. FIG. 3 shows organ accumulations are reported in units of percent of injected dose per gram of tissue (% ID $g^{-1}$). a) 1 h after intravenous administration of 3 nmol 1c (blue) and 6c (red) b) 2 h after intravenous administration of 3 nmol 1c (blue) and 6c (red) c) 4 h after intravenous administration of 3 nmol 1c (blue) and 6c (red) d) Calibration curve (average of triplicates) for the conversion of fluorescence intensity to % ID $g^{-1}$. Error bars indicate standard deviations. All data points are averages of three mice.

Figure 10:
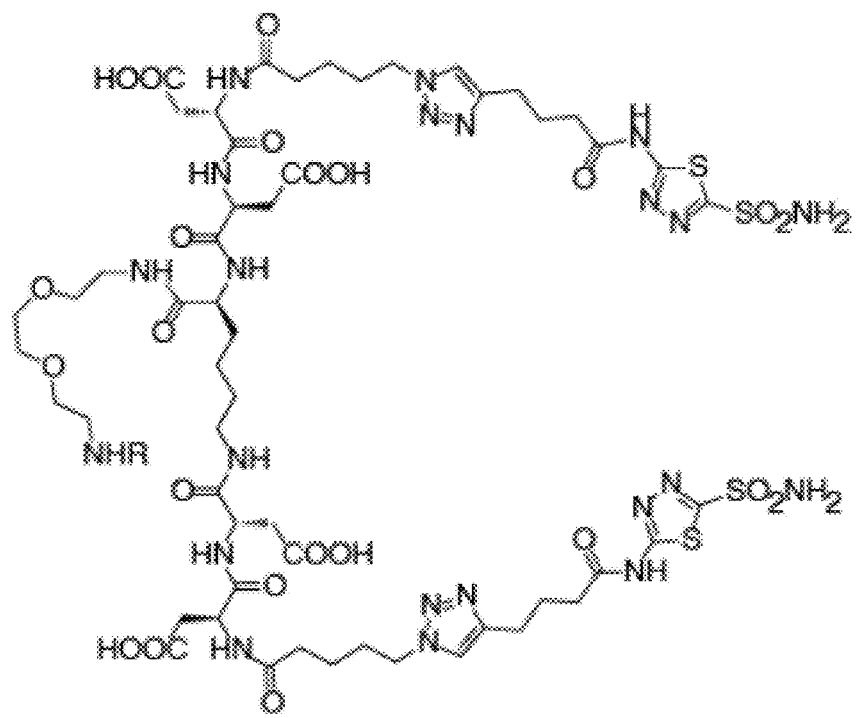
FIG. 10 shows structures of a bivalent ligand for CAIX and a dye-conjugate thereof.

Accumulation of 1c in the tumor was rapid and efficient with 13.4±3.0% of injected dose per gram of tissue (% ID $g^{-1}$) after only 1 h (FIG. 2b, Supporting FIGS. 10 and 11). This result compares favorably with previous work on antibody-based targeting of CAIX expressing tumors, where only markedly lower tumor uptake values (a maximum of 2.4±0.2% ID $g^{-1}$) could be detected.[27] In our case, the dye conjugate 1c, however, progressively dissociated from the tumor (residence $t_{1/2} \approx 1$ h), suggesting that an improvement of CAIX binding affinity may further contribute to efficient tumor targeting performance.

A tumor-to-blood ratio of 13.8:1 was observed 1 h after intravenous injection of 1c and further improved to 79.2:1 after 4 h. Tumor-to-organ ratios for excretory organs ranged between 0.2:1 for liver and 1.4:1 for kidneys after 1 h but a high level of selectivity was observed for other organs (e.g., 27.6:1 for tumor to heart after 1 h). Since AAZ is a CA ligand with broad isoform selectivity[, the observed differential uptake patterns are probably strongly influenced by relative CA expression levels in different tissues and the accessibility of the antigen (e.g., intracellular CAII can be expected to be inaccessible to our charged molecules). Importantly, tumor targeting was clearly dependent on the CAIX-binding moiety, as revealed by the 22-fold higher tumor accumulation at 1 h of the AAZ-based targeted dye conjugate 1c compared to the non-targeted dye 6c. Assuming that 6c is a good model for the tissue distribution of "naked" (i.e., untargeted) anticancer agents, this comparison highlights the potential impact of ligand-based drug delivery of therapeutically relevant doses of drugs into neoplastic masses.

FIG. 4 shows biodistribution analysis of 1c in balb/c nu/nu mice bearing subcutaneous SKRC52 tumors including stomach and blood values 1, 2 and 4 h after giving 3 nmol of the dye conjugate intravenously. Organ accumulations are reported in units of % ID $g^{-1}$. Error bars indicate standard deviations. Data shown are averages of three mice.

Analysis of Tumor Penetration

Mice bearing subcutaneous SKRC52 tumors (200-300 $mm^3$ in size) were injected intravenously with Alexa546 (Invitrogen) labeled probes 1b or 6b (50 nmol) dissolved in PBS pH 7.4 (150 µL). After 1 h, 2 h or 4 h animals were injected with a solution of Hoechst 33342 (Invitrogen, 5.4 mM) in saline (150 µL) and sacrificed after 5 min Organs were extracted as above and flash-frozen in Neg-50 cryo medium (Thermo Scientific) using liquid nitrogen. After warming to −20° C., samples were cut into sections of 10 µm width and directly imaged on an Axioskop 2 fluorescence microscope (Zeiss).

It was found that although the conjugate has already started penetrating into the tumor after 30 min, staining of the tumor with 1b is initially highest in well-perfused areas. Later, the staining becomes more homogeneous. After 2 h the staining becomes weaker as the conjugate is starting to get washed out of the tumor. Fluorescence due to 6b cannot be detected inside the tumor, which is in accordance with the lack of macroscopic accumulation observed with 6c.

Microscopic analysis of organs showed strong fluorescence due to 1b inside the tumor and the intestine. The latter probably is due to hepatobiliary excretion of the dye conjugate. An observed layer of fluorescence in the stomach most likely corresponds to gastric mucosal epithelial cells, which express CAIX under normal conditions. Kidney and liver also showed some fluorescence as a result of conjugate excretion through these organs.

Dosage

Estimation of the recommended therapy dose of a) 7a and b) 8a in nude mice was performed by studying different dosages using a schedule of five injections on five consecutive days compared to vehicle (5% DMSO in PBS pH 7.4). The dosage regimens were 0.4 nmol/day, 1.3 nmol/day, 4.0 nmol/day and 13.3 nmol/day. One mouse was used for each regimen. When the animal did not lose more than 5% of its initial body weight over 15 days after the initial injection, it was assumed, that the dose was well tolerated.

The study showed that 7a was tolerated up to 4.0 nmol/day, but poorly tolerated at 13.3 nmol/day. The study further showed that 8a was well tolerated up to and including 13.3 nmol/day.

Figure 5:
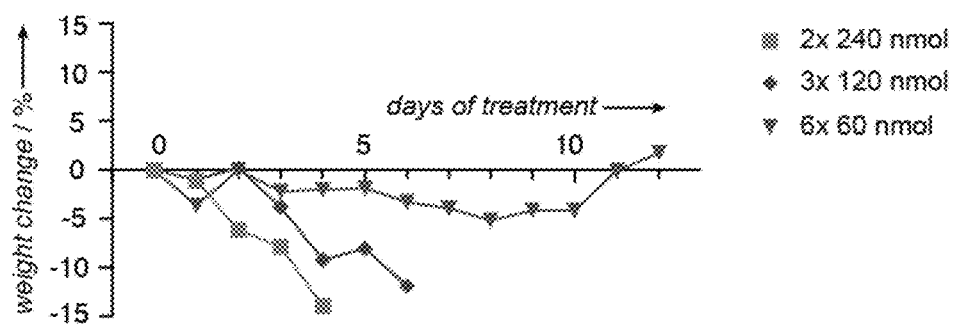
FIG. 5 shows graphs of weight loss versus time for test animals treated with three different dosage regimens of a ligand-linker-drug conjugate according to the invention.

Estimation of the recommended therapy dose and schedule of DM1 conjugate 9a was studied in SKRC52 tumor bearing nude mice. One mouse was used for testing each dosing scheme. Injections were given daily starting on day 0 in 5% DMSO in PBS pH 7.4 (150 µL). The results are shown in FIG. 5. Six doses of 60 nmol 9a were tolerated with only minimal weight loss. Since the animals in this study weighed on average 18% less than those used in the therapy study, a dose of 70 nmol per injection was used for the therapy experiment. The number of injections was also increased from 6 to 7 on 7 consecutive days.

Therapy Experiments

SKRC52 xenograft tumors were implanted into balb/c nu/nu mice (Charles River) as described above. After 14 days, mice were randomly assigned into therapy groups of 5 or 6 animals and treatment started. 5 doses of 4 nmol 7a,b, 8a,b or 7 doses of 70 nmol 9a,b each in PBS pH 7.4 (150 µL) containing 5% DMSO were given on 5 or 7 consecutive days and one group was treated with vehicle (5% DMSO in PBS pH 7.4). In the case of 7-9b an equimolar amount of AAZ was added to the injection solution to control for a possible antitumor activity of CAIX inhibitors. Sorafenib and sunitinib were administered at a standard dose of 30 mg/kg as described previously.[5] Animals were weighed and tumor sizes measured daily and the tumor volume calculated according to the formula (long side)×(short side)$^2$×0.5. Animals were sacrificed when the body weight fell by more than 15% relative to the first therapy day or when tumors reached a volume of >2000 mm$^3$. Prism 6 (GraphPad Software) was used for data analysis (regular two-way ANOVA with the Bonferroni test).

Figure 6:
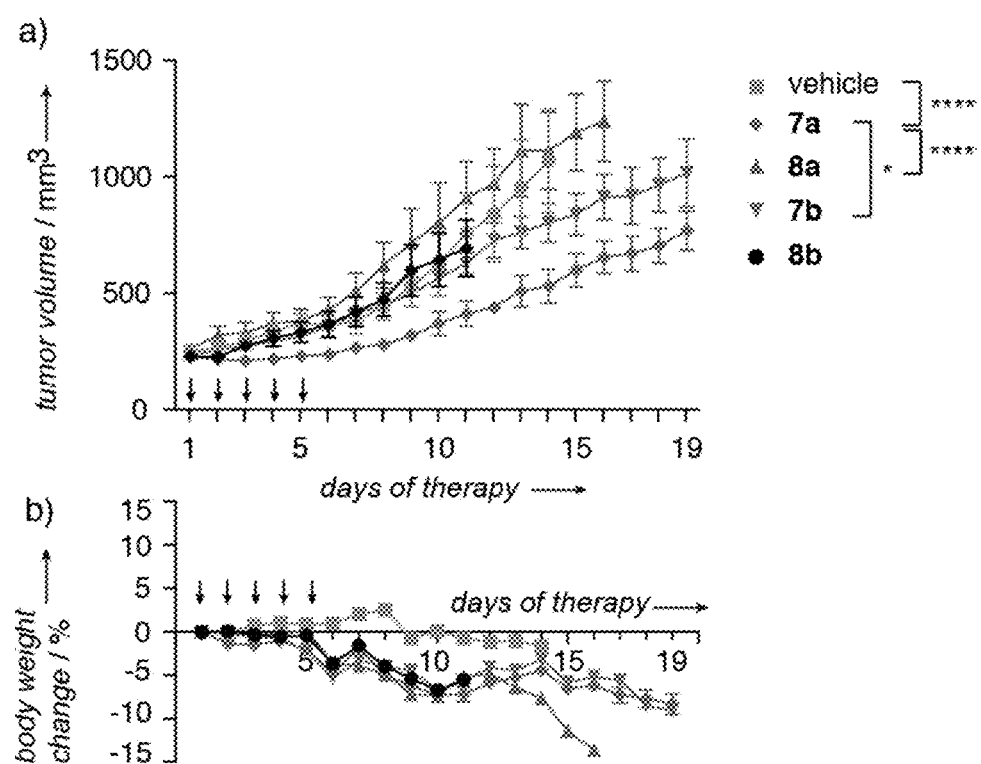
FIG. 6 shows graphs of (a) tumor volume versus time for growth of SKRC52 xenografts in balb/c nu/nu mice treated 5× on 5 consecutive days with two different conjugates 7a and 8a according to the invention and with two corresponding untargeted drug conjugates, and (b) measured body weight change associated with the treatment.
Figure 7:
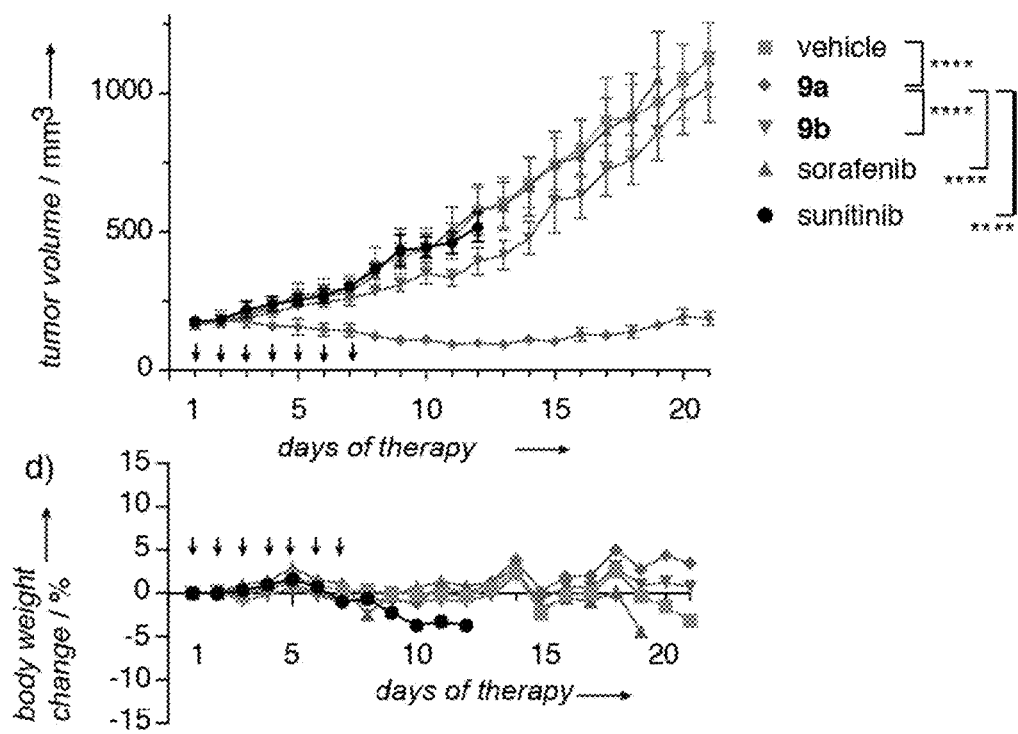
FIG. 7 shows graphs of (a) tumor volume versus time for growth of SKRC52 xenografts in balb/c nu/nu mice treated 5× on 5 consecutive days with a further conjugate 9a according to the invention and with a corresponding untargeted drug conjugates and with two conventional antitumor drugs, and (b) measured body weight change associated with the treatments.

Results are shown in FIGS. 6 and 7. Error bars give standard errors. The therapeutic results obtained with the duocarmycin-AAZ conjugates only indicated a modest tumor growth inhibition effect (FIG. 6a). Nevertheless, targeted carbonate 7a gave rise to statistically significant tumor growth retardation compared to mice that only received vehicle (p<0.0001) and mice receiving untargeted conjugate 7b plus equimolar amounts of AAZ (p<0.05). The carbamate-based constructs 8a and 8b did not lead to any retardation in tumor growth. It seems reasonable that the low affinity of 8a towards the antigen ($K_D$=40.3±2.6 nm versus $K_D$=7.3±0.5 nm for 7a) and inefficient extracellular activation may have been partly responsible for this effect. The treatment could be performed with a weight loss lower than 15% of body weight (FIG. 6b).

For the DM1 conjugate 9a, a potent anti-tumor effect was observed at doses, which gave only minimal toxicity (i.e., no detectable body weight loss giving 7×70 nmol of DM1-conjugate 9a on 7 consecutive days). During the treatment period tumors shrank and continued to reduce in volume for 7 additional days. Only 20 days after the start of treatment, tumors started regrowing, as a consequence that mice had not received any additional drug treatment. Importantly, neither sorafenib nor sunitinib, which represent the most commonly used chemotherapeutic agents for the treatment of kidney cancer, exhibited any detectable antitumor effect, in line with previous reports in different models of kidney cancer. These findings suggest that the targeted delivery of potent cytotoxic agents may provide a therapeutic advantage compared to the current standard of care. DM1 may be a particularly suitable payload for the development of targeted cytotoxics, since the presence of e.g., an ester moiety in its structure may facilitate its detoxification in clearance-related organs, thus sparing healthy tissues.

(B) Bivalent Binding Moieties

A comparative study of the tumour targeting performance of monovalent and bivalent ligands to carbonic anhydrase IX (CAIX) in renal cell carcinoma was performed as follows.

Synthesis of Fluorescence Labeled Targeting Ligands

Figure 9:
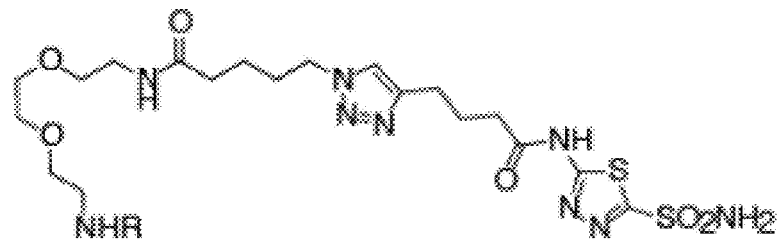
FIG. 9 shows structures of a monovalent ligand for CAIX and a dye-conjugate thereof.

Monovalent acetazolamide (AAZ) derivative B1 and bivalent AAZ derivative B2 having the structures shown in FIGS. 8 and 9 were synthesised using standard Fmoc solid phase peptide chemistry. These binding moieties were fluorescence labelled with IRDye 750 to provide fluorescence labelled monovalent and bivalent ligands B3 and B4. The synthesis methods were as follows.

Synthesis of AAZTL—B1

Commercially available polystyrene Wang p-nitrophenyl carbonate resin (250 mg, 0.15 mmol) was swollen in DMF (5 mL for 5 min) and reacted with a solution of 2,2'-(ethane-1,2-diylbis(oxy))diethanamine (250 µL), DIPEA (500 µL) and DMAP (2.5 mg) in DMF (4.5 mL) for 12 h at room temperature under shaking. The resin was washed with DMF (3×5 mL for 1 min), MeOH (3×5 mL for 1 min) and again DMF (3×5 mL for 1 min). A solution of 5-azido valeric acid (65 mg, 0.45 mmol), HATU (171 mg, 0.45 mmol) and DIPEA (148 µL, 0.9 mmol) was prepared and immediately reacted with the resin for 1 h at room temperature under shaking. After washing with DMF (6×1 min×5 mL) a solution of CuI (2.9 mg, 0.015 mmol), TBTA (8 mg, 0.015 mmol) and alkyne 10 (123 mg, 0.45 mmol) in a mixture of DMF (1 mL) and THF (1 mL) was prepared and reacted with the resin for 24 h at room temperature. After washing with DMF (3×1 min×5 mL), 50 mM aq. EDTA solution (3×1 min×5 mL), DMF (3×1 min×5 mL) and DCM (3×1 min×5 mL), the compound was cleaved by agitating the resin with a mixture of TFA (2.2 mL), TIS (50 µL), H₂O (50 µL), m-cresol (100 µL) and thioanisol (100 µL) for 2 h at room temperature. The resin was washed with TFA (1×5 min×2.5 mL) and the combined cleavage and washing solutions added drop-wise to ice cold diethyl ether (100 mL). The precipitate was collected by centrifugation and the product purified by reversed-phase HPLC (95% A/5% B to 20% A/80% B over 20 min). After lyophilisation the title compound was collected as a white powder (78 mg, 0.14 mmol, 95%).

$^1$H-NMR (500 MHz, DMSO-$d_6$) δ [ppm]=13.01 (s, 1H), 8.32 (s, 2H), 7.89-7.82 (m, 5H), 4.28 (t, J=7.0 Hz, 2H), 3.58-3.50 (m, 6H), 3.38 (t, J=6.1 Hz, 2H), 3.18 (m, 2H), 3.00 (m, 2H), 2.65 (t, J=7.5 Hz, 2H), 2.59 (t, J=7.4 Hz, 2H), 2.09 (t, J=7.4 Hz, 2H), 1.94 (m, 2H), 1.75 (m, 2H), 1.42 (m, 2H); $^{13}$C-NMR (125 MHz, DMSO-$d_6$) δ [ppm]=172.5, 172.4, 164.8, 161.5, 146.4, 122.4, 70.1, 69.8, 69.6, 67.1, 49.4, 39.1, 38.8, 35.0, 35.7, 29.8, 24.8, 24.6, 22.6; HRMS: (m/z) [M+H]⁺ calcd. for $C_{19}H_{34}N_9O_6S_2$ 548.2068. found 548.2071.

Synthesis of B2

Commercially available polystyrene Wang p-nitrophenyl carbonate resin (500 mg, 0.3 mmol) was swollen in DMF (5 mL for 5 min) and reacted with a solution of 2,2'-(ethane-1,2-diylbis(oxy))diethanamine (500 µL), DIPEA (500 µL) and DMAP (5 mg) in DMF (4 mL) for 12 h at room temperature under shaking. The resin was washed with DMF (3×5 mL for 1 min), MeOH (3×5 mL for 1 min) and again DMF (3×5 mL for 1 min). A solution of Fmoc-Lys(Fmoc)-OH (532 mg, 0.9 mmol), HBTU (341 mg, 0.9 mmol), HOBt (138 mg, 0.9 mmol) and DIPEA (298 µL, 1.8 mmol) was prepared and immediately reacted with the resin for 1 h at room temperature under shaking. After washing with DMF (6×1 min×5 mL) the Fmoc group was removed with 20% piperidine in DMF (1×1 min×5 min and 2×10 min×5 mL) and the resin washed with DMF (6×1 min×5 mL) before the next coupling step was initiated. In the following, the peptide was extended with Fmoc-Asp(OtBu)-OH twice followed by 5-azido-valerate. For this purpose, a solution of acid (1.2 mmol), HATU (465 mg, 1.2 mmol) and DIPEA (397 µL, 2.4 mmol) was prepared in DMF (5 mL) and reacted with the resin for 1 h at room temperature under gentle agitation. Each coupling was followed by a washing step with DMF (6×1 min×5 mL) and Fmoc deprotection as described above. After coupling of the azide, a solution of CuI (76 mg, 0.12 mmol), TBTA (21 mg, 0.12 mmol) and alkyne 10 (329 mg, 1.2 mmol) in a mixture of DMF (2.5 mL) and THF (2.5 mL) was prepared and reacted with the resin for 48 h at room temperature. After washing with DMF (3×1 min×5 mL), 50 mM aq. EDTA solution (3×1 min×5 mL), DMF (3×1 min×5 mL) and DCM (3×1 min×5 mL), the compound was cleaved by agitating the resin with a mixture of TFA (4.4 mL), TIS (100 µL), H₂O (100 µL), m-cresol (200 µL) and thioanisol (200 µL) for 2 h at room temperature. The resin was washed with TFA (1×5 min×5 mL) and the combined cleavage and washing solutions added drop-wise to ice cold diethyl ether (100 mL). The precipitate was collected by centrifugation, dissolved in aq. MeCN and lyophilised to yield the title compound as an off-white powder (468 mg, 0.3 mmol, quant.).

$^1$H-NMR (400 MHz, DMSO-$d_6$) δ [ppm]=13.09 (s, 2H), 8.37 (s, 4H), 8.29-8.26 (m, 3H), 8.14 (d, J=8.0 Hz, 2H), 7.91 (s, 2H), 7.80-7.78 (m, 3H), 7.71 (d, J=8.0 Hz, 1H), 7.65 (t, J=5.4 Hz, 1H), 4.60-4.48 (m, overlaps with broad H₂O peak), 4.33 (t, J=7.0 Hz, overlaps with broad H₂O peak), 4.19-4.13 (m, overlaps with broad H₂O peak), 3.64-3.59 (m, 6H), 3.44 (t, J=6.3 Hz, 2H), 3.27-3.23 (m, 2H), 3.05-3.00 (m, 4H), 2.77-2.48 (m, overlaps with solvent peak), 2.20 (t, J=7.2 Hz, 4H), 2.04-1.96 (m, 4H), 1.86-1.78 (m, 4H), 1.74-1.63 (br m, 1H), 1.61-1.16 (br m, 9H); HRMS: (m/z) [M+H]⁺ calcd. for $C_{54}H_{83}N_{22}O_{23}S_4$ 1535.4879. found 1535.4868.

Synthesis of B3

To IRDye750 NHS ester (100 µg, 84 nmol) in DMSO (10 µL) and DMF (100 µL) was added acetazolamide derivative B1 (200 µg, 366 nmol) in DMSO (20 µL) and DIPEA (2 µL, 12 µmol). The mixture was allowed to stand at room temperature for 2 h and then directly purified over reversed-phase HPLC (95% A/5% B to 40% A/60% B over 30 min). Fractions containing dye conjugate were identified through their characteristic UV/VIS spectrum ($\lambda_{max}$=750 nm), pooled, lyophilised and dissolved in DMSO (50 µL) to give a dark green stock solution. Its concentration and the reaction yield were determined by measuring the absorbance at 750 nm ($\epsilon_{750}$=260,000 M⁻¹ cm⁻¹) of stock samples diluted 1:200 into PBS pH 7.4 (640 µM, 32 nmol, 38%).

HRMS: (m/z) [M+4H]⁺ calcd. for $C_{68}H_{92}N_{11}O_{19}S_6$ 1558.4890. found 1558.4844.

Synthesis of B4

To IRDye750 NHS ester (100 µg, 84 nmol) in DMSO (10 µL) and DMF (100 µL) was added B2 (200 µg, 130 nmol) in DMSO (20 µL) and DIPEA (2 µL, 12 µmol). The mixture was allowed to stand at room temperature for 2 h and then directly purified over reversed-phase HPLC (95% A/5% B to 40% A/60% B over 30 min). Fractions containing dye conjugate were identified through their characteristic UV/VIS spectrum ($\lambda_{max}$=750 nm), pooled, lyophilised and dissolved in DMSO (50 µL) to give a dark green stock solution. Its concentration and the reaction yield were determined by measuring the absorbance at 750 nm ($\epsilon_{750}$=260,000 M⁻¹ cm⁻¹) of stock samples diluted 1:200 into PBS pH 7.4 (287 µM, 14 nmol, 17%). HRMS: (m/z) [M+4H]⁺ calcd. for $C_{103}H_{141}N_{24}O_{36}S_8$ 2545.7700. found 2545.7703.

Binding Performance by Surface Plasmon Resonance

Binding experiments of monovalent and bivalent AAZ derivatives to CAIX using surface plasmon resonance indicated a fast association for both compounds ($k_a$=1.48×10⁶ M⁻¹ s⁻¹ and $k_{a1}$=1.28×10⁶ M⁻¹ s⁻¹, $k_{a2}$=1.36×10⁶ RU⁻¹ respectively). Whilst monovalent ligand B1 completely dissociated from the CAIX-coated surface within seconds ($k_d$=0.015 s⁻¹, $K_d$=10.5 nM), bivalent compound B2 exhibited no apparent dissociation and could only be removed with harsh acid treatment (FIG. 1b).

Binding Performance by Flow Cytometry

Flow cytometry was performed as described above with monovalent and bivalent near infrared dye conjugates B3 and B4 and negative control conjugates lacking the ligand on CAIX-positive SKRC52 cells and CAIX-negative HEK cells[5]. The results indicated a clear ligand- and receptor-dependent binding to cells. The shift in fluorescence intensity for bivalent conjugate B4 was more pronounced than the one observed for monovalent B3, which is consistent with the results obtained from SPR.

In Vivo Investigation of Targeting Performance

Further studies tested the ability of near infrared dye conjugates B3 and B4 to localise to CAIX-expressing SKRC52 xenografts in vivo. Both dye conjugates strongly accumulated in the tumour, as revealed by whole animal near infrared fluorescence imaging and by analysis of the extracted organs. While the initial clearance profile was comparable for both targeted molecules, the bivalent conjugate B4 exhibited a significantly longer residence on the tumour. Twenty-four hours after injection, the integrated fluorescence signal in the tumour from bivalent conjugate B4 was 40%, while the monovalent conjugate B3 had decayed to 14% of its initial value (p=0.002; unpaired two-sided t-test; Supplementary FIG. 4).

To gain a better understanding of the absolute tumour uptake of monovalent dye conjugate B3 compared to bivalent B4 and tumour to organ selectivity, organs were extracted, tissues homogenised and fluorescence intensity measured on a per gram basis. Comparison to a standard dilution series of IRDye750 in organ homogenate allowed the measurement of absolute uptake levels into organs, as percent injected dose per gram (% ID g$^{-1}$). Bivalent dye conjugate B4 exhibited a >3-fold higher absolute accumulation in tumours compared to monovalent B3 at 24 h (5.3±0.6 versus 1.4±0.6% IDg$^{-1}$). Compound B4 thus compares very favourably with recently described monoclonal antibodies against CAIX. While uptake into heart, spleen, muscle and circulation in blood relative to tumour was low (tumour:organ>30), slightly lower tumour to organ ratios were observed for kidneys and stomach for both conjugates. Interestingly, tumour:liver and tumour:intestine ratios were lower for monovalent B3 than for bivalent B4 whilst B4 exhibited a higher tumour:lung ratio than B3.

Synthesis of Drug Conjugates

Targeted and untargeted drug conjugates B7 and B8 having the structures shown in FIG. 10 were prepared as follows. Compound B7 is a bivalent conjugate according to the present invention and has the same bivalent targeting scaffold as B2 and B4. B8 is a reference example having a similar scaffold but no AAZ targeting ligands.

Synthesis of B7

Bivalent targeted linker B11 (20 mg, 13 µmol), TCEP.HCl (7.6 mg, 27 µmol) and DIPEA (2 µL) were dissolved in degassed DMF (500 µL). After 1 h 2,2'-dipyridyldisulphide (11.7 mg, 53 µmol) was added. The mixture was stirred at room temperature for 12 h, diluted with NMP (500 µL) and was added drop wise to ice cold diethyl ether (40 mL). The precipitate was collected by centrifugation, re-dissolved in DMF (200 µL) and NMP (200 µL) and precipitated again with ice cold diethyl ether (40 mL) and dried under vacuum to give the activated disulphide as a white residue (18 mg, 11 µmol, 85%). An aliquot of the activated disulphide (15 mg, 9 µmol) was dissolved in DMF (400 µL) and DM1 free thiol (7 mg, 9 µmol) added. The reaction was allowed to stand at room temperature for 48 h after which the product was recovered by reversed phase HPLC (95% A/5% B to 20% A/80% B over 20 min). Fractions containing the desired product by MS were pooled and lyophilised to yield the title compound as an off white powder (9.5 mg, 4 µmol, 47%).

$^1$H-NMR (500 MHz, DMSO-d$_6$) δ [ppm]=12.98 (s, 2H), 8.31 (s, 4H), 8.22-8.15 (m, 4H), 8.07 (d, J=8.2 Hz, 1H), 7.85 (s, 2H), 7.69-7.59 (m, 2H), 7.12 (s, 1H), 6.89 (s, 1H), 6.61-6.52 (m, 3H), 5.92 (br s, 1H), 5.57-5.52 (m, 1H), 5.30-5.29 (m, 1H), 4.52-4.43 (m, 5H), 4.39-4.34 (m, 1H), 4.27 (t, J=6.9 Hz, 4H), 4.19-4.16 (m, 1H), 4.08-4.03 (m, 1H), 3.92-3.90 (m, 3H), 3.53-2.41 (m, overlap with solvent peak), 2.13-2.12 (m, 4H), 2.04-2.01 (m, 1H), 1.97-1.91 (m, 4H), 1.79-1.73 (m, 4H), 1.67-1.54 (m, 4H), 1.51-1.10 (m, 21H), 0.77 (s, 3H);

HRMS: (m/z) [M+2H]$^{2+}$ calcd. for C$_{86}$H$_{119}$ClN$_{24}$O$_{33}$S$_6$ 1122.3270. found 1122.3279.

Synthesis of B8

Bivalent untargeted linker B12 (20 mg, 17 µmol), TCEP.HCl (19 mg, 68 µmol) and DIPEA (10 µL) were dissolved in degassed DMF (1 mL). After 1 h 2,2'-dipyridyldisulphide (22 mg, 100 µmol) was added. The mixture was stirred at room temperature for 12 h, diluted with NMP (500 µL) and was added drop wise to ice cold diethyl ether (40 mL). The precipitate was collected by centrifugation, re-dissolved in DMF (200 µL) and NMP (200 µL) and precipitated again with ice cold diethyl ether (40 mL) and dried under vacuum to give the activated disulphide as a white residue (45 mg, product+side products). An aliquot of the residue (15 mg) was dissolved in DMF (400 µL) and DM1 free thiol (7 mg, 9 µmol) was added. The reaction was allowed to stand at room temperature for 48 h after which the product was recovered by reversed phase HPLC (95% A/5% B to 20% A/80% B over 20 min). Fractions containing the desired product by MS were pooled and lyophilised to yield the title compound as an off white powder (7.4 mg, 3.9 µmol, 42%).

$^1$H-NMR (500 MHz, DMSO-d$_6$) δ [ppm]=8.22-8.09 (m, 5H), 7.83 (s, 2H), 7.64-7.58 (m, 2H), 7.12 (s, 1H), 6.89 (s, 1H), 6.61-6.52 (m, 3H), 5.93 (s, 1H), 5.55 (dd, J=9.1, 14.8 Hz, 1H), 5.32-5.28 (m, 1H), 4.56-4.43 (m, 6H), 4.27 (t, J=6.85 Hz, 4H), 4.20-4.17 (m, 1H), 4.05 (t, J=12.2 Hz, 1H), 3.91 (s, 3H), 3.49-2.41 (m, overlap with solvent peak), 2.25 (t, J=7.4 Hz, 4H), 2.15 (m, 4H), 2.04-2.02 (br m, 1H), 1.80-1.73 (m, 8H), 1.62-1.10 m, 24H), 0.77 (s, 3H); HRMS: (m/z) [M+H]$^+$ calcd. for C$_{82}$H$_{116}$ClN$_{16}$O$_{31}$S$_2$ 1919.7117. found 1919.7098.

Synthesis of B9

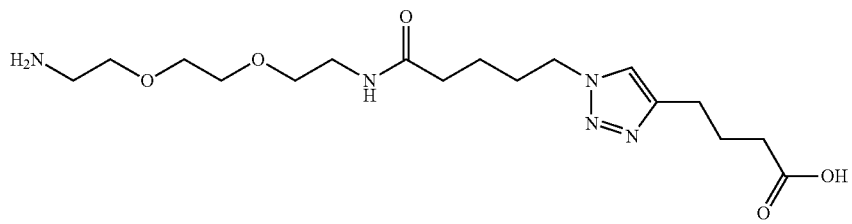 [SMILES: NCCOCCOCCNC(=O)CCCCn1cc(CCCC(=O)O)nn1]

mg, 9 µmol) was dissolved in DMF (400 µL) and DM1 free thiol (7 mg, 9 µmol) added. The reaction was allowed to stand at room temperature for 48 h after which the product was recovered by reversed phase HPLC (95% A/5% B to 20% A/80% B over 20 min). Fractions containing the Commercially available polystyrene Wang p-nitrophenyl carbonate resin (250 mg, 0.15 mmol) was swollen in DMF (5 mL for 5 min) and reacted with a solution of 2,2'-(ethane-1,2-diylbis(oxy))diethanamine (250 µL), DIPEA (500 µL) and DMAP (2.5 mg) in DMF (4.5 mL) for 12 h at room temperature under shaking. The resin was washed with DMF (3×5 mL for 1 min), MeOH (3×5 mL for 1 min) and again DMF (3×5 mL for 1 min). A solution of 5-azido valeric acid (65 mg, 0.45 mmol), HATU (171 mg, 0.45 mmol) and DIPEA (148 μL, 0.9 mmol) was prepared and immediately reacted with the resin for 1 h at room temperature under shaking. After washing with DMF (6×1 min×5 mL) a solution of CuI (2.9 mg, 0.015 mmol), TBTA (8 mg, 0.015 mmol) and 5-hexynoic acid (51 mg, 50 μL, 0.45 mmol) in a mixture of DMF (1 mL) and THF (1 mL) was prepared and reacted with the resin for 24 h at room temperature. After washing with DMF (3×1 min×5 mL), 50 mM aq. EDTA solution (3×1 min×5 mL), DMF (3×1 min×5 mL) and DCM (3×1 min×5 mL), the compound was cleaved by agitating the resin with a mixture of TFA (2.2 mL), TIS (50 μL), H$_2$O (50 μL), m-cresol (100 μL) and thioanisol (100 μL) for 2 h at room temperature. The resin was washed with TFA (1×5 min×2.5 mL) and the combined cleavage and washing solutions added drop-wise to ice cold diethyl ether (100 mL). The precipitate was collected by centrifugation and the product purified by reversed-phase HPLC (95% A/5% B to 20% A/80% B over 20 min). After lyophilisation the title compound was collected as a white powder (21 mg, 54 μmol, 36%).

$^1$H-NMR (400 MHz, DMSO-d$_6$) δ [ppm]=7.90-7.86 (m, 5H), 4.29 (t, J=7.0 Hz, 2H), 3.60-3.51 (m, 6H), 3.40 (t, J=6.1 Hz, 2H), 3.20 (q, J=5.8 Hz, 2H), 3.00-2.96 (m, 2H), 2.62 (t, J=7.6 Hz, 2H), 2.26 (t, J=7.4 Hz, 2H), 2.10 (t, J=7.4 Hz, 2H), 1.85-1.74 (m, 4H), 1.46-1.42 (m, 2H); $^{13}$C-NMR (125 MHz, DMSO-d$_6$) δ [ppm]=174.8, 172.4, 146.7, 122.3, 70.1, 69.8, 69.5, 67.2, 49.4, 39.0, 38.9, 35.0, 33.6, 29.8, 24.9, 24.8, 22.7; HRMS: (m/z) [M+H]$^+$ calcd. for C$_{17}$H$_{32}$N$_5$O$_5$ 386.2398. found 386.2403.

Synthesis of B10

(138 mg, 0.9 mmol) and DIPEA (298 μL, 1.8 mmol) was prepared and immediately reacted with the resin for 1 h at room temperature under shaking. After washing with DMF (6×1 min×5 mL) the Fmoc group was removed with 20% piperidine in DMF (1×1 min×5 min and 2×10 min×5 mL) and the resin washed with DMF (6×1 min×5 mL) before the next coupling step was initiated. In the following, the peptide was extended with Fmoc-Asp(OtBu)-OH twice followed by 5-azido-valerate. For this purpose, a solution of acid (1.2 mmol), HATU (465 mg, 1.2 mmol) and DIPEA (397 μL, 2.4 mmol) was prepared in DMF (5 mL) and reacted with the resin for 1 h at room temperature under gentle agitation. Each coupling was followed by a washing step with DMF (6×1 min×5 mL) and Fmoc deprotection as described above. After coupling of the azide, a solution of CuI (76 mg, 0.12 mmol), TBTA (21 mg, 0.12 mmol) and 5-hexynoic acid (440 μL, 1.2 mmol) in a mixture of DMF (2.5 mL) and THF (2.5 mL) was prepared and reacted with the resin for 48 h at room temperature. After washing with DMF (3×1 min×5 mL), 50 mM aq. EDTA solution (3×1 min×5 mL), DMF (3×1 min×5 mL) and DCM (3×1 min×5 mL), the compound was cleaved by agitating the resin with a mixture of TFA (4.4 mL), TIS (100 μL), H$_2$O (100 μL), m-cresol (200 μL) and thioanisol (200 μL) for 2 h at room temperature. The resin was washed with TFA (1×5 min×5 mL) and the combined cleavage and washing solutions added drop-wise to ice cold diethyl ether (100 mL). The precipitate was collected by centrifugation and the product purified by reversed-phase HPLC (95% A/5% B to 20% A/80% B over 20 min). After lyophilisation the title compound was collected as a white powder (64 mg, 53 μmol 17%).

$^1$H-NMR (400 MHz, DMSO-d$_6$) δ [ppm]=8.25-8.22 (m, 3H), 8.09 (d, J=8.1 Hz, 1H), 7.85 (s, 2H), 7.78-7.73 (br m,

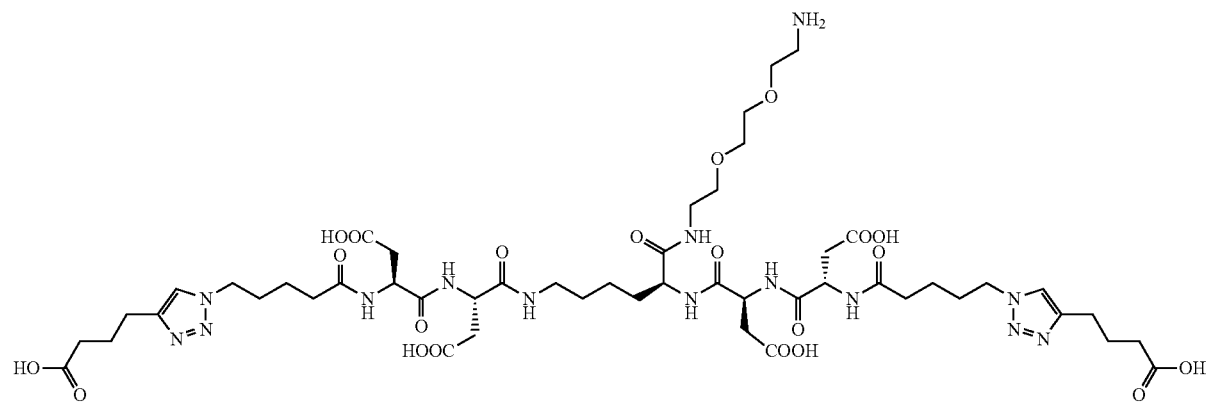 [SMILES: NCCOCCOCCNC(=O)[C@H](CCCCNC(=O)[C@H](CC(=O)O)NC(=O)[C@H](CC(=O)O)NC(=O)CCCCn1cc(CCCC(=O)O)nn1)NC(=O)[C@H](CC(=O)O)NC(=O)[C@H](CC(=O)O)NC(=O)CCCCn1cc(CCCC(=O)O)nn1]

Commercially available polystyrene Wang p-nitrophenyl carbonate resin (500 mg, 0.3 mmol) was swollen in DMF (5 mL for 5 min) and reacted with a solution of 2,2'-(ethane-1,2-diylbis(oxy))diethanamine (500 μL), DIPEA (500 μL) and DMAP (5 mg) in DMF (4 mL) for 12 h at room temperature under shaking. The resin was washed with DMF (3×5 mL for 1 min), MeOH (3×5 mL for 1 min) and again DMF (3×5 mL for 1 min). A solution of Fmoc-Lys(Fmoc)-OH (532 mg, 0.9 mmol), HBTU (341 mg, 0.9 mmol), HOBt 3H), 7.66 (d, J=7.9 Hz, 1H), 7.59 (t, J=5.3 Hz, 1H), 4.55-4.44 (m, 4H), 4.29 (t, J=7.0 Hz, 4H), 4.14-4.09 (m, 2H), 3.60-3.55 (m, 6H), 3.40 (t, J=6.2 Hz, 2H), 3.22-3.19 (m, 2H), 3.01-2.92 (m, 4H), 2.73-2.44 (m, overlap with solvent peak), 2.26 (t, J=7.4 Hz, 4H), 2.15 (t, J=7.2 Hz, 4H), 1.85-1.74 (m, 7H), 1.70-1.60 (br m, 1H), 1.55-1.14 (br m, 9H); HRMS: (m/z) [M+H]$^+$ calcd. for C$_{50}$H$_{79}$N$_{14}$O$_{21}$ 1211.5539. found 1211.5515.

Synthesis of B11

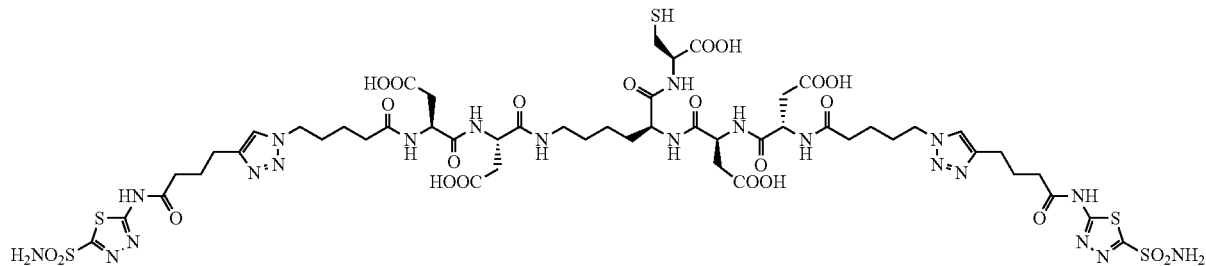 [SMILES: NS(=O)(=O)c1nnc(NC(=O)CCCc2cn(CCCCC(=O)N[C@@H](CC(=O)O)C(=O)N[C@@H](CC(=O)O)C(=O)NCCCC[C@H](NC(=O)[C@H](CC(=O)O)NC(=O)[C@H](CC(=O)O)NC(=O)CCCCn3cc(CCCC(=O)Nc4nnc(S(N)(=O)=O)s4)nn3)C(=O)N[C@@H](CS)C(=O)O)nn2)s1]

Commercially available pre-loaded Fmoc-Cys(Trt) on Tentagel resin (500 mg, 0.415 mmol, RAPP Polymere) was swollen in DMF (3×5 min×5 mL), the Fmoc group removed with 20% piperidine in DMF (1×1 min×5 mL and 2×10 min×5 mL) and the resin washed with DMF (6×1 min×5 mL). A solution of Fmoc-Lys(Fmoc)-OH (736 mg, 1.25 mmol), HBTU (472 mg, 1.25 mmol), HOBt (191 mg, 1.25 mmol) and DIPEA (412 µL, 2.5 mmol) was prepared and immediately reacted with the resin for 1 h at room temperature under shaking. After washing with DMF (6×1 min×5 mL) the Fmoc group was removed with 20% piperidine in DMF (1×1 min×5 min and 2×10 min×5 mL) and the resin washed with DMF (6×1 min×5 mL) before the next coupling step was initiated. In the following, the peptide was extended with Fmoc-Asp(OtBu)-OH twice followed by 5-azido-valerate. For this purpose, a solution of acid (1.7 mmol), HATU (643 mg, 1.7 mmol) and DIPEA (549 µL, 3.3 mmol) was prepared in DMF (5 mL) and reacted with the resin for 1 h at room temperature under gentle agitation. Each coupling was followed by a washing step with DMF (6×1 min×5 mL) and Fmoc deprotection as described above. After coupling of the azide, a solution of CuI (106 mg, 0.17 mmol), TBTA (29 mg, 0.17 mmol) and alkyne 10 (455 mg, 1.7 mmol) in a mixture of DMF (2.5 mL) and THF (2.5 mL) was prepared and reacted with the resin for 48 h at room temperature. After washing with DMF (3×1 min×5 mL), 50 mM aq. EDTA solution (3×1 min×5 mL), DMF (3×1 min×5 mL) and DCM (3×1 min×5 mL), the compound was cleaved by agitating the resin with a mixture of TFA (4.4 mL), TIS (100 µL), H$_2$O (100 µL), m-cresol (200 µL) and thioanisol (200 µL) for 2 h at room temperature. The resin was washed with TFA (1×5 min×5 mL) and the combined cleavage and washing solutions added drop-wise to ice cold diethyl ether (100 mL). The precipitate was collected by centrifugation and the product purified by reversed-phase HPLC (95% A/5% B to 20% A/80% B over 20 min). After lyophilisation the title compound was collected as a white powder (68 mg, 45 µmol, 10%).

$^1$H-NMR (400 MHz, DMSO-d$_6$) δ [ppm]=13.01 (s, 2H), 8.32 (s, 4H), 8.21 (t, J=7.5 Hz, 3H), 8.09 (d, J=8.1 Hz, 1H), 8.05 (d, J=7.9 Hz, 1H), 7.87 (s, 2H), 7.74 (d, J=7.84 Hz, 1H), 7.61 (t, J=5.4 Hz, 1H), 4.55-4.45 (m, overlap with broad water peak), 4.40-4.34 (m, overlap with broad water peak), 4.29 (t, J=7.0 Hz, overlap with broad water peak), 4.24-4.22 (m, overlap with broad water peak), 3.07-2.94 (br m, 2H), 2.90-2.41 (m, overlap with solvent peak), 2.15 (t, J=7.1 Hz, 4H), 1.99-1.92 (m, 4H), 1.82-1.74 (m, 4H), 1.71-1.24 (br m, 10H); HRMS: (m/z) [M+H]$^+$ calcd. for C$_{51}$H$_{74}$N$_{21}$O$_{23}$S$_5$ 1508.3864. found 1508.3861.

Synthesis of B12

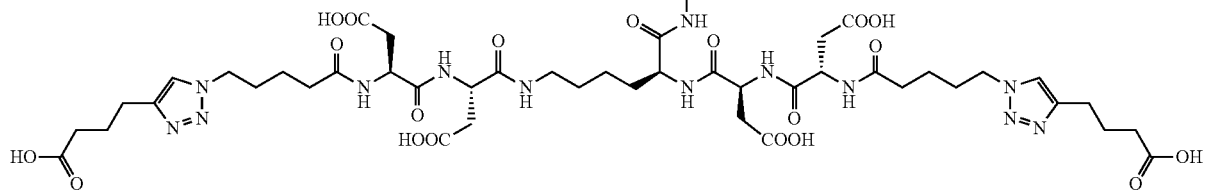

Commercially available pre-loaded Fmoc-Cys(Trt) on Tentagel resin (500 mg, 0.415 mmol, RAPP Polymere) was swollen in DMF (3×5 min×5 mL), the Fmoc group removed with 20% piperidine in DMF (1×1 min×5 mL and 2×10 min×5 mL) and the resin washed with DMF (6×1 min×5 mL). A solution of Fmoc-Lys(Fmoc)-OH (736 mg, 1.25 mmol), HBTU (472 mg, 1.25 mmol), HOBt (191 mg, 1.25 mmol) and DIPEA (412 µL, 2.5 mmol) was prepared and immediately reacted with the resin for 1 h at room temperature under shaking. After washing with DMF (6×1 min×5 mL) the Fmoc group was removed with 20% piperidine in DMF (1×1 min×5 min and 2×10 min×5 mL) and the resin washed with DMF (6×1 min×5 mL) before the next coupling step was initiated. In the following, the peptide was extended with Fmoc-Asp(OtBu)-OH twice followed by 5-azido-valerate. For this purpose, a solution of acid (1.7 mmol), HATU (643 mg, 1.7 mmol) and DIPEA (549 µL, 3.3 mmol) was prepared in DMF (5 mL) and reacted with the resin for 1 h at room temperature under gentle agitation. Each coupling was followed by a washing step with DMF (6×1 min×5 mL) and Fmoc deprotection as described above. After coupling of the azide, a solution of CuI (106 mg, 0.17 mmol), TBTA (29 mg, 0.17 mmol and 5-hexyonic acid (609

μL, 1.7 mmol) in a mixture of DMF (2.5 mL) and THF (2.5 mL) was prepared and reacted with the resin for 48 h at room temperature. After washing with DMF (3×1 min×5 mL), 50 mM aq. EDTA solution (3×1 min×5 mL), DMF (3×1 min×5 mL) and DCM (3×1 min×5 mL), the compound was cleaved by agitating the resin with a mixture of TFA (4.4 mL), TIS (100 μL), H$_2$O (100 μL), m-cresol (200 μL) and thioanisol (200 μL) for 2 h at room temperature. The resin was washed with TFA (1×5 min×5 mL) and the combined cleavage and washing solutions added drop-wise to ice cold diethyl ether (100 mL). The precipitate was collected by centrifugation and the product purified by reversed-phase HPLC (95% A/5% B to 20% A/80% B over 20 min). After lyophilisation the title compound was collected as a white powder (147 mg, 0.12 mmol, 30%).

$^1$H-NMR (500 MHz, DMSO-d$_6$) δ [ppm]=8.22-8.19 (m, 3H), 8.08 (d, J=8.9 Hz, 1H), 8.02 (d, J=7.8 Hz, 1H), 7.83 (s, 2H), 7.72 (d, J=7.8 Hz, 1H), 7.59-7.56 (m, 1H), 4.56-4.43 (m, 3H), 4.37-4.34 (m, 1H), 4.27-4.20 (m, 4H), 3.03-2.92 (m, 2H), 2.87-2.39 (m, overlap with solvent peak), 2.25 (t, J=7.35 Hz, 4H), 2.13 (t, J=7.0 Hz, 4H), 1.83-1.21 (br m, 16H); HRMS: (m/z) [M+H]$^+$ calcd. for $C_{47}H_{70}N_{13}O_{21}S$ 1184.4524. found 1184.4508.

Properties of Drug Conjugates

Both the targeted drug B7 and untargeted B8 were equally toxic in vitro. If conjugates were internalised in a receptor-dependent fashion and activated intracellularly, targeted conjugate B7 would be expected to accumulate in CAIX-expressing cells and to be more toxic than untargeted drug B8. This does not seem to be the case. The present inventors thus hypothesised that the conjugate would accumulate at the tumour site, where reducing agents (e.g., glutathione released from dying cells) would cleave the disulfide bond in extracellular space and lead to drug release. DM1 would then diffuse into adjacent cells to act on its intracellular target.

A preliminary dose finding study with conjugate B7 was conducted. Even a dose as low as 6 nmol on 8 consecutive days led to substantial tumour shrinkage. Five doses of 48 nmol within six days completely eradicated the tumour but showed some toxicity. Finally, a therapeutic schedule of 35 nmol on 8 consecutive days was used, which was well-tolerated in SKRC52 tumour bearing mice (FIG. 11). On the 12$^{th}$ day after the start of treatment, two mice were tumour free and the average tumour volume for all mice had dropped from 200 mm$^3$ initial tumour volume to below 50 mm$^3$. The two mice with complete regression and one from the dose escalation study were tumour free 90 days after start of therapy and were thus considered cured. The remaining tumours regrew. Importantly, control conjugates lacking the targeting ligand, or bivalent scaffold B2 without the payload did not have a statistically significant antitumor effect.

(C) Binding Moieties by Screening of a DNA-Encoded Library

Chemical technologies for the discovery of high-affinity protein binders provide techniques to go beyond naturally-occurring ligands for disease targeting applications. Combinatorial chemical libraries of unprecedented size can be constructed and screened by tagging organic molecules with DNA fragments, serving as amplifiable identification barcodes [group Liu; group Neri]. DNA-encoded chemical libraries, first postulated by Lerner and Brenner [REF], can be synthesized with one or two sets of molecules displayed at the extremities of complementary DNA strands, yielding single- or dual-pharmacophore chemical libraries, respectively.

The present inventors have studied a novel DNA-encoded self-assembling chemical (ESAC) library, containing 111, 100 small molecules in order to identify a new bivalent binding moiety for CAIX.

Synthesis of DNA-Encoded Self-Assembling Chemical (ESAC) Library

Figure 13:
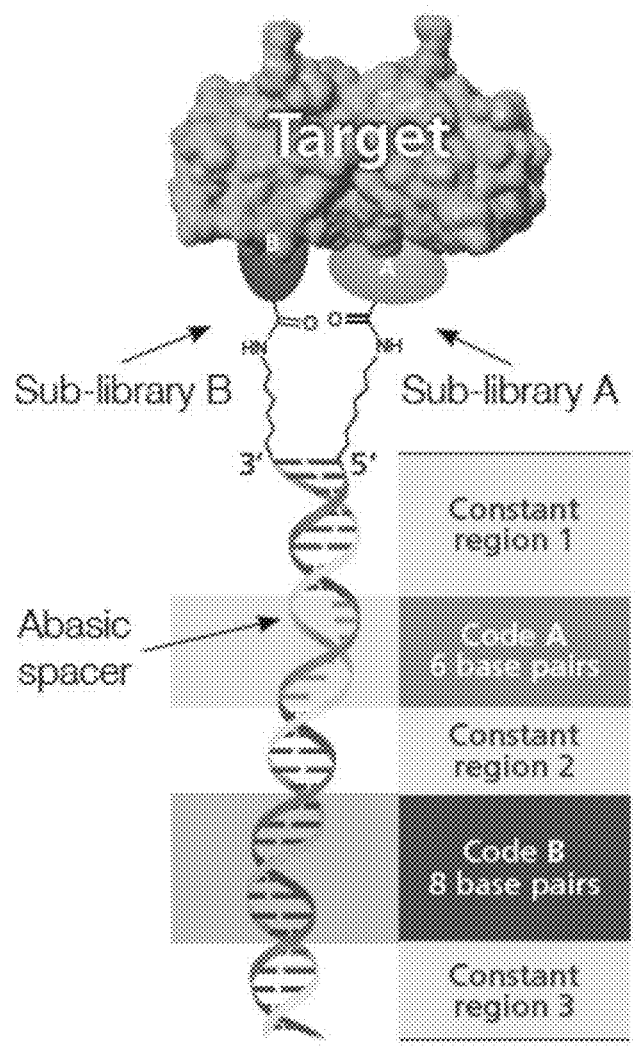
FIG. 13 shows a schematic representation of a member of the DNA-encoded self-assembling chemical (ESAC) library binding to its target protein CAIX. The library displays two pharmacophores A and B and is formed by hybridization of two individually synthesised single-stranded sub-libraries A and B, resulting in a combinatorial library of A×B=111,100 members.

A dual pharmacophore ESAC library of 111,100 compounds was synthesised using a novel chemical strategy which allows the sequence-based identification and quantification of library members. The Encoded Self-Assembling Chemical (ESAC) library was constructed by hybridizing two individually synthesized and purified single-stranded sublibraries A and B. Chemical compounds carrying a carboxylic acid, anhydride, N-hydroxysuccinimide ester or isothiocyanate groups were coupled to the primary amino group at the 5'-end (sublibrary A) or 3'-end (sublibrary B) of modified oligonucleotides to produce the library as shown in FIG. 13.

Sub-Library A Synthesis.

The synthesis of the DNA-encoded sub-library A of 550 compounds has been described by Dumelin, C. E., Scheuermann, J., Melkko, S. & Neri, D. in *Bioconjugate chemistry* 17, 366-370 (2006). In short, 48-mer oligonucleotides (IBA GmbH) carrying a free amino group at the 5'-end (ω-amino-hexyl phosphate diester) were reacted with activated carboxylic acid-, sulfonyl chloride- or isothiocyanate-containing building blocks to give the corresponding amide, sulfonamide and thiourea conjugates. Oligonucleotide sequences followed the pattern 5'-GGA GCT TCT GAA TTC TGT GTG CTG XXX XXX CGA GTC CCA TGG CGC AGC-3', where XXX XXX represents the coding sequence (6 nucleotides) that unambiguously identifies each individual library member.

Sub-Library B Synthesis.

Sub-library B was built using 41-mer 3'-amino-modified oligonucleotides, which were coupled with activated Fmoc-protected amino acid, carboxylic acid, carboxylic acid anhydride and sulfonyl chloride building blocks to give the corresponding amide or sulfonamide conjugates. All library compounds were coupled initially to the same oligonucleotide of the sequence 5'-CAT GGG ACT CG ddd ddd CAG CAC ACA GAA TTC AGA AGC TCC-3' (IBA GmbH), which was designed to be complementary to the sub-library A oligonucleotides and contained a 6 nucleotide abasic spacer region (d, deoxyabasic), which allows promiscuous duplex formation with the coding region of sub-library Conjugation of Fmoc-Protected Amino Acids and Carboxylic Acids with 3'-Amino-Modified Sub-Library B Oligonucleotide:

Fmoc-protected amino acids or carboxylic acids in dimethyl sulfoxide (DMSO, 12.5 μl, 100 mM), 1-ethyl-3-(3-dimethylaminopropyl)carbodiimide (EDC) in DMSO (12 μl, 100 mM), N-hydroxysulfosuccinimide (S—NHS) in 2:1 DMSO/H$_2$O, (10 μl, 333 mM) were added to DMSO (215 μl) and allowed to stand at 30° C. for 30 min Subsequently, a mixture of aminomodified sub-library B oligonucleotide in H$_2$O (5 μl, 5 nmol) and triethylamine hydrochloride in H2O (TEA.HCl, 50 μl 500 mM, pH 10.0) was added and the reaction kept at 30° C. for 12 h. Carboxylic acid conjugation reactions were quenched with tris(hydroxylmethyl)aminomethane hydrochloride in H2O (Tris.HCl, 20 μl, 500 mM, pH 8.1) at 30° C. for 1 h. Fmoc-protected amino acid conjugation reactions were quenched and deprotected with Tris in H2O (5 μl, 1 M) and TEA (5 μl) at 30° C. for 1 h. After quenching and deprotection, the DNA-compound conjugate was precipitated with EtOH before purifying by HPLC. The separated and collected oligonucleotide-compound conjugates were vacuum-dried overnight, redissolved in H2O (100 µl), and analysed by ESI-LC-MS31.

Conjugation of Sulfonyl Chlorides with 3'-Amino-Modified Sub-Library B Oligonucleotide:

Sulfonyl chlorides in acetonitrile (MeCN, 25 µl, 100 mM) were mixed with sodium hydrogen carbonate in H2O (25 µl, 1 M, pH 9.0), MeCN (100 µl), $H_2O$ (95 µl) and subsequently reacted with amino-modified sub-library B oligonucleotide in $H_2O$ (5 µl, 5 nmol) at 30° C. for 12 h. The reaction was quenched with Tris.HCl (20 µl, 500 mM, pH 8.1) at 30° C. for 1 h. After quenching the DNA-compound conjugate was precipitated with EtOH before purifying by HPLC. The separated and collected oligonucleotide-compound conjugates were vacuum-dried overnight, redissolved in $H_2O$ (100 µl), and analysed by ESI-LC-MS. The separated and collected oligonucleotide-compound conjugates were vacuum-dried overnight, redissolved in H2O (100 µl), and analysed by ESI-LCMS.

Conjugation of Carboxylic Acid Anhydrides with 3'-Amino-Modified Sub-Library B Oligonucleotide:

Carboxylic acid anhydrides in DMSO (25 µl, 100 mM) were mixed with sodium hydrogen phosphate in $H_2O$ (25 µl, 500 mM, pH 7.1), DMSO (195 µl), $H_2O$ (35 µl) and subsequently reacted with amino-modified sub-library B oligonucleotide in H2O (5 µl, 5 nmol) overnight at 30° C. The reaction was quenched with Tris.HCl (20 µl, 500 mM, pH 8.1) at 30° C. for 1 h. After quenching the DNA-compound conjugate was precipitated with EtOH before purifying by HPLC31. The separated and collected oligonucleotide-compound conjugates were vacuum-dried overnight, redissolved in H2O (100 µl), and analysed by ESI-LC-MS. To unambiguously label library members in sub-library B, individual oligonucleotide-compound conjugates were extended with a unique identifier sequence. For this purpose, 202 39-mer code oligonucleotides of sequence 5'-CCT GCA TCG AAT GGA TCC GTG XXX XXX XX GCA GCT GCG C-3' (IBA GmbH) were used, where XXX XXX XX denotes an 8-digit code region. The 202 HPLC-purified oligonucleotide-compound conjugates were ligated to these coding oligonucleotides with the help of a chimeric (DNA/RNA) adapter oligonucleotide (5'-CGA GTC CCA TGG CGC AGC TGC-3', bold: RNA portions), which is complementary to both, the sub-library B oligonucleotide-compound conjugates and the sub-library B code oligonucleotides. The adapter oligonucleotide was eventually removed by RNase H (New England Biolabs) treatment.

Ligation Protocol:

Sub-library B oligonucleotide-compound conjugate in $H_2O$ (50 µl, 2 µM), sub-library B code oligonucleotide in $H_2O$ (10 µl, 15 µM), sub-library B chimeric RNA/DNA adapter oligonucleotide in $H_2O$ (10 µl, 30 µM), 10× ligation reaction buffer (10 µl, New England Biolabs) and $H_2O$ (19.5 µl) were mixed and heated up to 90° C. for 2 min before the mixture was allowed to cool down to 22° C. T4 DNA ligase (0.5 µl, New England Biolabs) was added and ligation performed at 16° C. for 10 hours before inactivating the ligase at 70° C. for 15 min.

Library Hybridization and Code Transfer to Sub-Library A Strand.

To obtain the final library, sub-libraries A and B were first hybridized, resulting in a combinatorial collection of duplexes, where each member of sub-library A could pair with each member of sub-library B. For the unambiguous identification of any dual pharmacophore combination by high-throughput sequencing, coding information for A and B need to be given on the same DNA strand. This was achieved by a Klenow polymerase assisted sublibrary A strand extension of the A/B heteroduplexes, which transferred the coding information from the sublibrary B strand onto the sublibrary A strand Hybridization and Klenow-encoding protocol: Sub-library A in $H_2O$ (115 µl, equimolar mixture of all library members, total concentration 864 nM), and sub-library B in H2O (100 µl, equimolar mixture of all library members, total concentration 1 µM), 10×NEB2 reaction buffer (100 µl, New England Biolabs) and $H_2O$ (685 µl) were mixed and heated up to 90° C. for 2 min, then cooled down to 22° C. The hybridized library was purified with nucleotide removal columns (Qiagen, elution with 6×140 µl Qiagen EB buffer on six separate columns). For Klenow-encoding, hybridized and purified ESAC library in EB buffer (800 µl), 10×NEB2 reaction buffer (100 µl, New England Biolabs), deoxynucleotide (dNTP) solution mix (100 µl, 500 µM, final concentration 50 µM, New England Biolabs) and Klenow fragment (10 µl, New England Biolabs) were mixed and incubated at 37° C. for 30 min.

Cloning, Expression and Biotinylation of CAIX.

Recombinant His6-tagged human CAIX was cloned and expressed as described by J. K. Ahlskog et al. in British Journal of Cancer 101, 645-657 (2009). The protein was chemically biotinylated with EZ-Link NHS-Biotin (Thermo Scientific) for affinity screening according to supplier's instructions.

Affinity Screening of the ESAC Library Against CAIX.

Affinity selections were performed using a KingFisher magnetic particle processor (Thermo Scientific). Streptavidin-coated magnetic beads (0.1 mg) were resuspended in PBS (100 µl, 50 mM NaPi, 100 mM NaCl, pH 7.4) and subsequently incubated with biotinylated CAIX (100 µl, 0.1 µM or 1.0 µM concentration) for 30 min with continuous gentle mixing. CAIX-coated beads were washed three times with PBST (200 µl, 50 mM NaPi, 100 mM NaCl, 0.05% v/v Tween 20, pH 7.4) that was supplemented with biotin (100 µM) in order to block remaining binding sites on streptavidin, and subsequently incubated with the ESAC library (100 µl, 100 nM total concentration, in PBST) for 1 h with continuous gentle mixing. After removing unbound library members by washing five times with PBST (200 µl), beads carrying bound library members were resuspended in buffer EB (100 µl, QIAquick PCR purification kit, Qiagen) and the DNA-compound conjugates separated from the beads by heat denaturation of streptavidin and CAIX (95° C. for 5 min). The DNA of eluted library members was amplified by PCR, introducing at the same time additional, selection-specific DNA barcodes, and submitted to Illumina® high-throughput DNA sequencing.

Figure 14:
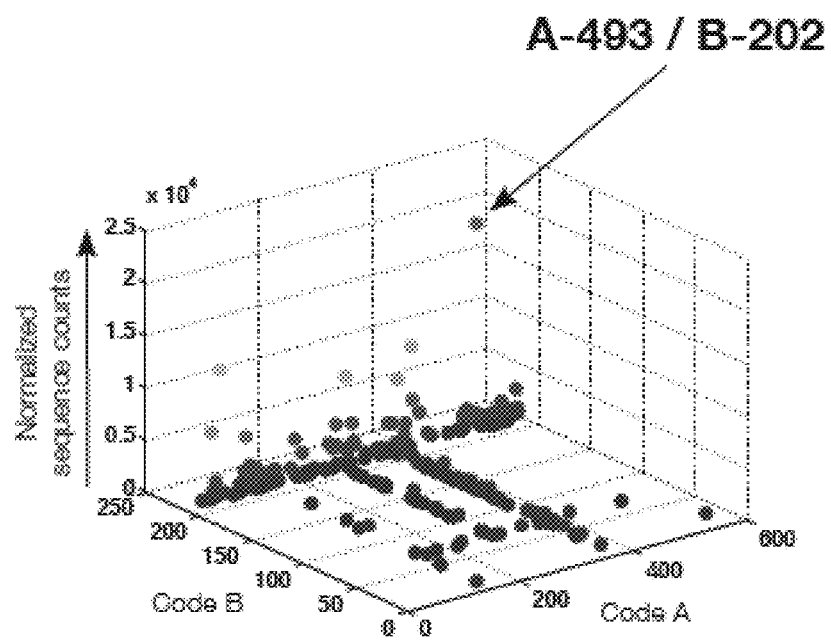
FIG. 14 shows a plot of the results of high-throughput DNA sequencing (HTDS) results of reactions against CAIX for the ESAC library. The x/y plane represents the library member barcodes of sub-library A and sub-library B, and the z-axis shows the sequence counts normalised to 100, cut-off level 1000. Selection conditions were high-density protein coating (1.0 μm CAIX) and five washing steps.

In multiple selection experiments, the A-493/B-202 pair of pharmacophores was found to be highly enriched (FIG. 14), compared to the unselected library and to the other library members after CAIX selection (>200-fold enrichment):

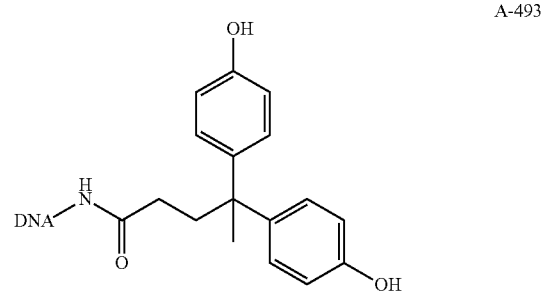

A-493

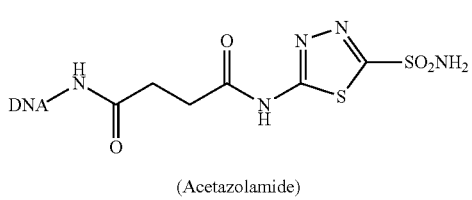

(Acetazolamide)

In Vitro Binding Studies

A-493 and B-202 were first conjugated with fluorescently labelled 8-mer complementary amino-modified locked nucleic acids (LNA™), allowed to form a heteroduplex structure and submitted to fluorescence polarization affinity measurements against CAIX. Fluorescence polarization (FP) measurements were performed by incubating 5 nM fluorescently labelled probe and recombinant human Carbonic Anhydrase IX with increasing concentrations for 1 h at 22° C. The FP was measured on a Spectra Max Paradigm multimode plate reader (Molecular Devices). On LNA™, the A-493/B-202 combination revealed a dissociation constant of 14.6±0.7 nM, whereas B-202 (acetazolamide) alone had a $K_d$ of 34.9±0.9 nM.

Synthesis of CAIX Ligands with and without Fluorophores

Figure 16:
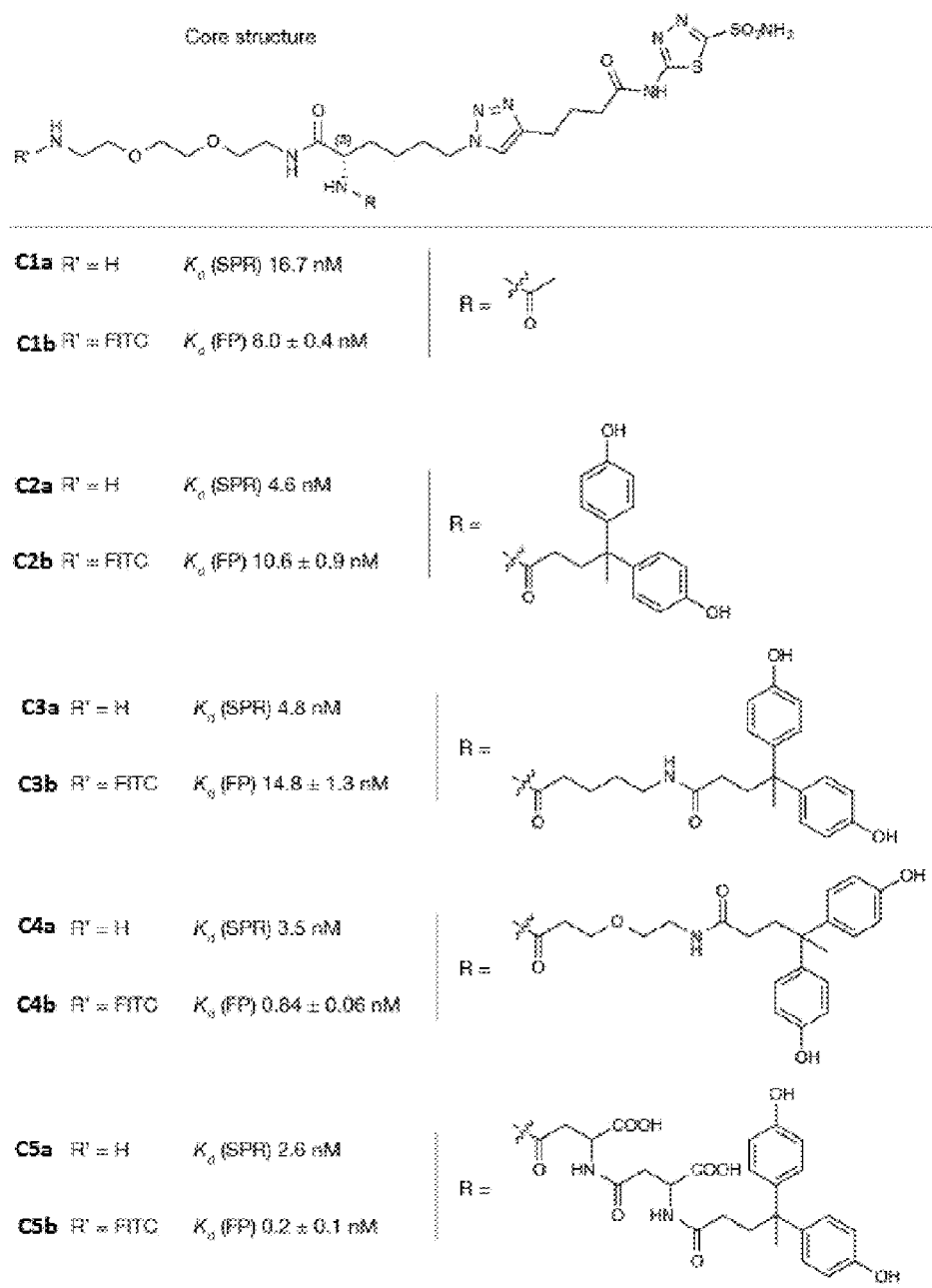
FIG. 16 shows chemical structures and dissociation constants measured "off-DNA" by FP and SPR of synthesized monovalent and bivalent conjugates with different linker lengths.

Next, linked chemical compounds having binding moieties with and without fluorophores having the structures shown in FIG. 16 were synthesized using standard solid-phase coupling procedures using various spacers, containing a modification site for an optional fluorophore conjugation. Representative syntheses (compounds C5a and C5c) were performed as follows.

N-[4,4-bis(4-hydroxyphenyl)pentanoyl]-β-aspartyl-β-aspartyl-N-{2-[2-(2-aminoethoxy) ethoxy]ethyl}-6-(4-{4-oxo-4-[(5-sulfamoyl-1,3,4-thiadiazol-2-yl)amino]butyl}-1H-1,2,3-triazol-1-yl)-L-norleucinamide (C5a)

Commercially available pre-loaded O-bis-(aminoethyl) ethylene glycol on trityl resin (200 mg, 0.12 mmol) was swollen first in DCM (3×5 min×2 ml) and then in DMF (3×5 min×2 ml). Fmoc-protected azidolysine (142 mg, 0.36 mmol), HBTU (137 mg, 0.36 mmol), HOBt.H₂O (55 mg, 0.36 mmol) and DIPEA (119 µl, 0.72 mmol) were dissolved in DMF (2 ml), the mixture was allowed to stand at 22° C. for 15 min and then reacted with the resin for 1 h under gentle agitation. After washing with DMF (6×1 min×2 ml) the Fmoc group was removed with 20% piperidine in DMF (1×2 min×2 ml and 2×10 min×2 ml) and the resin washed with DMF (6×1 min×2 ml) before the peptide was extended 2× with N-α-Fmoc-L-aspartic acid α-tert-butyl ester (148 mg, 0.36 mmol) and 4,4-bis(4-hydroxyphenyl)valeric acid (103 mg, 0.36 mmol) in the indicated order using the same coupling (HBTU/HOBt.H₂O/DIPEA) and Fmoc-deprotection (20% piperidine in DMF) conditions mentioned before. After the last peptide coupling step, a solution of CuI (2.3 mg, 0.01 mmol), TBTA (6.4 mg, 0.01 mmol) and alkyne 10 (99 mg, 0.36 mmol) in a mixture of DMF (1 ml) and THF (1 ml) was prepared and reacted with the resin at 22° C. for 2 h. After washing with DMF (6×1 min×2 ml), the compound was cleaved by agitating the resin with a mixture of TFA (4.5 ml), TIPS (250 µl) and H₂O (250 µl) at 22° C. for 2 h. The resin was washed with TFA (1×5 min×2 ml) and the combined cleavage and washing solutions added drop-wise to ice cold diethyl ether (50 ml). The precipitate was collected by centrifugation and the product purified by reversed-phase HPLC (95% A/5% B to 20% A/80% B over 30 min). After lyophilization the title compound was collected as a white powder (49 mg, 46 µmol, 38% yield).

1H-NMR (500 MHz, DMSO-d6): δ 13.01 (s, 1H), 9.19 (br. s, 2H), 8.33 (s, 2H), 8.19 (d, J=8.0, 1H), 8.09 (d, J=7.9, 1H) 7.91 (d, J=8.1, 1H), 7.88 (t, J=6.0, 1H), 7.84 (s, 1H), 7.79 (br. s, 3H), 6.92 (d, J=8.4, 4H), 6.64 (d, J=8.4, 4H), 4.54-4.44 (m, 2H), 4.24 (t, J=7.2, 2H), 4.17 (td, J=8.3, 5.5, 1H), 3.58 (t, J=5.3, 2H), 3.56-3.50 (m, 4H), 3.38 (t, J=6.1, 2H), 3.24-3.15 (m, 2H), 2.97 (sext, J=5.6, 2H), 2.65 (t, J=7.5, 2H), 2.64-2.55 (m, 4H), 2.51-2.41 (m, 2H), 2.17 (t, J=8.2, 2H) 1.94 (quin, J=7.5, 2H), 1.88-1.82 (m, 2H), 1.75 (quin, J=7.5, 2H), 1.66-1.60 (m, 1H), 1.53-1.46 (m, 1H), 1.45 (s, 3H), 1.28-1.17 (m, 2H). 13C-NMR (125 MHz, DMSO-d6): δ 172.84, 172.79, 172.30, 172.04, 171.62, 169.19, 169.09, 164.33, 161.09, 154.96, 146.06, 139.65, 139.58, 127.81, 121.84, 114.68, 69.68, 69.46, 68.85, 66.70, 52.34, 49.08, 48.70, 43.86, 38.70, 38.53, 37.14, 36.95, 36.75, 34.27, 31.36, 31.27, 29.44, 27.39, 24.42, 24.23, 22.28. HRMS (ESI): m/z calcd. for C45H63N12O15S2 [M+H]+: 1075.3972. found: 1075.3966.

N-[4,4-bis(4-hydroxyphenyl)pentanoyl]-β-aspartyl-β-aspartyl-N-[2-(2-{2-[(5-{4-[(6E)-6-{(2E)-2-[3,3-dimethyl-5-sulfo-1-(4-sulfobutyl)-1,3-dihydro-2H-indol-2-ylidene]ethyl idene}-2-{(E)-2-[3,3-dimethyl-5-sulfo-1-(4-sulfobutyl)-3H-indolium-2-yl]ethenyl}cyclohex-1-en-1-yl]phenyl}pentanoyl)amino]ethoxy}ethoxy)ethyl]-6-(4-{4-oxo-4-[(5-sulfamoyl-1,3,4-thiadiazol-2-yl)amino]butyl}-1H-1,2,3-triazol-1-yl)-L-norleucinamide (C5c)

To C5a (161 µg, 150 nmol) in DMSO (16.1 µl) was added IRDye® 750 NHS ester (99 µg, 83 nmol) in DMSO (10 µl) followed by DMF (100 µl) and DIPEA (2 µl, 12 µmol). The solution was stirred at 22° C. for 2 h and then quenched with sodium hydrogen carbonate (100 µl, 100 mM, pH 8.0) before purifying over reversed-phase HPLC (95% A/5% B to 40% A/60% B over 30 min). Fractions containing dye conjugate were identified through their characteristic UV/VIS spectrum ($\lambda_{max}$=756 nm), pooled, lyophilized and dissolved in DMSO (50 µl) to give a dark green stock solution. Its concentration and the reaction yield were determined by measuring the absorbance at 756 nm ($\epsilon_{756}$=260'000 M−1 cm−1) of stock samples diluted 1:200 into PBS (pH 7.4): 1.00 mM, 50 nmol, 60% yield. HRMS (Dual MALDI/ESI): m/z calcd. for C94H121N14O28S6 [M+]: 2085.6793. found: 2085.6793.

The binding affinities of the synthetic compounds of FIG. 16 were then characterized by fluorescence polarization and by surface plasmon resonance, as follows.

Affinity Determination of CAIX Ligands by Fluorescence Polarization (FP) Measurements.

Fluorescein labelled ligands (5 nM diluted with PBS from DMSO stocks, final DMSO content adjusted to 0.001%) were incubated at 22° C. for 1 h in a black 384-well plate (Greiner, non-binding) in PBS (pH 7.4) with increasing concentrations of CAIX to a final volume of 60 µl. The fluorescence anisotropy was measured on a Spectra Max Paradigm multimode plate reader (Molecular Devices). Experiments were performed in triplicate and the mean anisotropy values fitted to the following equation using KaleidaGraph 4.1.3 (Synergy Software), $$A = \frac{1}{2}\left\{([P]_0 + [L]_0 + K_D) - \sqrt{([P]_0 + [L]_0 + K_D)^2 - 4[P]_0[L]_0}\right\}$$

where A is the anisotropy, [P]0 the total protein concentration, [L]0 the total concentration of the fluorescently labelled ligand and KD the dissociation constant.

Affinity Determination of CAIX Ligands by Surface Plasmon Resonance (SPR) Measurements.

Surface plasmon resonance experiments were carried out at room temperature (25° C.) using a Biacore™ T200 instrument and CM5 chips (GE Healthcare). For all measurements, a PBS buffer (pH 7.4) containing DMSO (5% v/v) and P20 surfactant (0.05% v/v, GE Healthcare) was used. CAIX protein was immobilized on the chip at about 3,000 response units using EDC.HCl and NHS as described by the instrument manufacturer. Serial dilutions of unlabelled compounds (0.08 nM to 620 nM in steps of ½) were used as analytes. After each cycle, the sensor surface was regenerated by a short treatment with DMSO (50% v/v) in H$_2$O. Sensorgrams were solvent corrected and the binding kinetics were analysed with the Biacore™ T200 evaluation software (version 2.0) using a 1:1 Langmuir binding model.

The best binders featured an Asp-Asp moiety in the linker (C5a and C5b) and a K$_d$ value of 0.2±0.1 nM by fluorescence polarization in solution. SPR measurements gave slightly higher dissociation constants. The best binder appeared to be the one with the longest linker.

The binding properties of the best A-493/B-202 conjugate were further studied on SK-RC-52 human kidney cancer cells by fluorescence-activated cell sorting. For this purposes the fluorescein moiety was replaced with a fluorescent near-infrared dye (IRDye® 750). Compounds lacking the B moiety or both A/B moieties were used as controls in the experiment.

Cell Culture.

SK-RC-52 and HEK cells were maintained in RPMI medium (Invitrogen) supplemented with fetal calf serum (10% v/v, FCS, Life Technologies) and Antibiotic-Antimycotic (AA, Life Technologies) at 37° C. and 5% CO$_2$. For passaging, cells were detached using Trypsin-EDTA 0.05% (Life Technologies) when reaching 90% confluence and re-seeded at a dilution of 1:10.

Ligand Binding Analysis by Flow Cytometry.

Cells were detached from culture plates using EDTA (50 mM) solution in PBS (pH 7.4), counted and suspended to a final concentration of 1.5×10$^6$ cells ml−1 in a solution of FCS (1% v/v)/PBS (pH 7.4). Aliquots of 3×10$^5$ cells (200 µl) were spun down and resuspended in solutions of IRDye® 750 (Licor) labelled ligands (30 nM) in FCS (1% v/v) in PBS (200 µl, pH 7.4) and incubated at 4° C. for 1 h. Cells were washed once with 200 µl FCS (1% v/v)/PBS (pH 7.4), spun down, resuspended in a solution of propidium iodide (30 µM, Sigma-Aldrich) in FCS (1% v/v)/PBS (300 µl, pH 7.4) and analysed on a FACS Canto flow cytometer (BD Bioscience). FlowJo Version 8.7 (Treestar) was used for data analysis and visualization.

Figure 17:
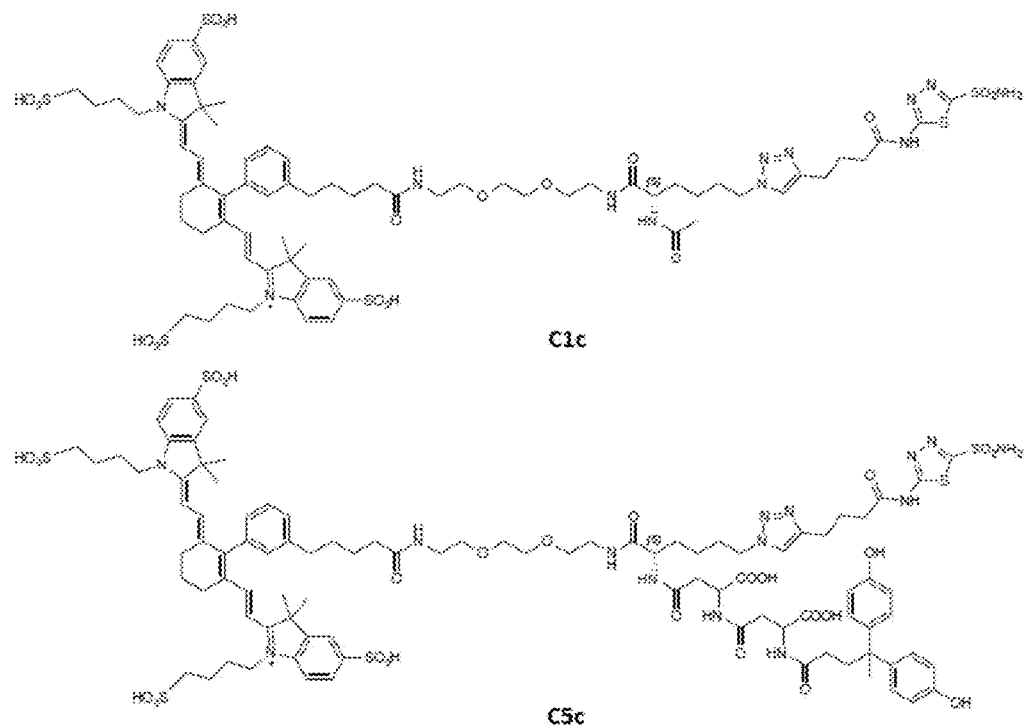
FIG. 17 shows the chemical structure of targeted monovalent and bivalent IRDye 750 conjugates C1c and C5c used for flow cytometry analysis and in vivo imaging experiments.
Figure 18:
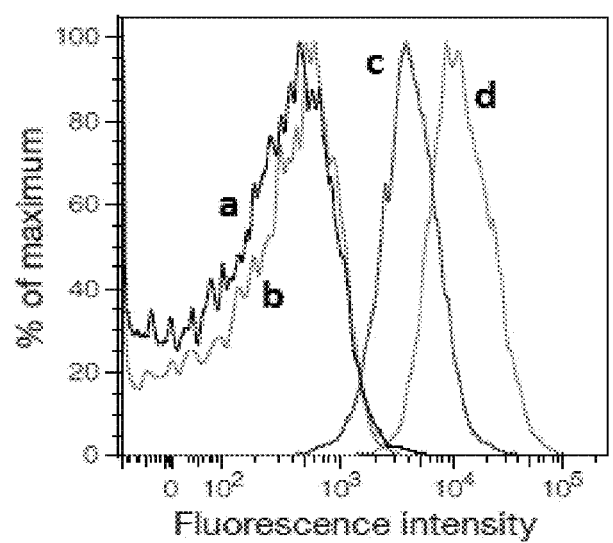
FIG. 18 shows flow cytometry analysis of IR-dye conjugates binding to CAIX expressing SKRC52 cells: (a) untreated cells, (b) untargeted conjugate C6, (c) targeted monovalent conjugate C1c, (d) targeted bivalent conjugate C5c.

These experiments showed that the IRDye 750 labeled compound C5c (FIG. 17) stained cells more strongly than the corresponding IRDye 750 labeled acetazolamide control C1a (FIG. 17). These results are shown in FIG. 18.

In Vivo Binding Studies

Figure 15:
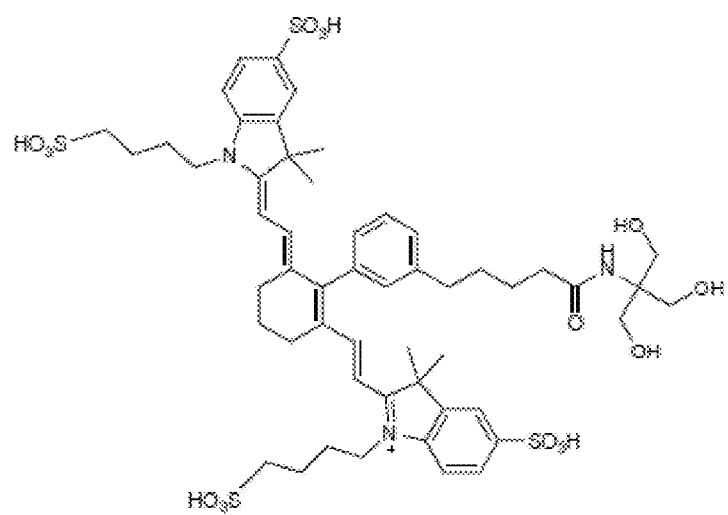
FIG. 15 shows the chemical structure of untargeted IRDye 750 conjugate C6 used for flow cytometry analysis and in vivo imaging experiments.

For IVIS imaging experiments, mice bearing subcutaneous SK-RC-52 tumors were injected intravenously with 3 nmol IRDye® 750 labelled CAIX ligands C1c, C5c and C6 (FIGS. 15,17) dissolved in 5% v/v DMSO in PBS pH 7.4 (150 µL). Mice were anesthetized with isoflurane and fluorescence images acquired on an IVIS Spectrum imaging system (Xenogen, exposure is, binning factor 8, excitation at 745 nm, emission filter at 800 nm, f number 2, field of view 13.1). Food and water was given ad libitum between measurements. Mice were subsequently sacrificed by cervical dislocation. Heart, lung, kidney, liver, spleen, a section of the intestine, skeletal muscle and the tumour were extracted and imaged individually using above parameters.

The untargeted dye C6 did not preferentially localize to the tumor at any time point, in full analogy to conventional chemotherapeutic agents. The acetazolamide derivative C1c exhibited a rapid preferential accumulation in the tumor, but gradually dissociated from the neoplastic mass over time. By contrast, the high-affinity bidentate A-493/B-202 ligand C5c exhibited a selective and long-lasting tumor targeting. The tumor targeting efficiency of C5c and C1c (18% and 3.7% injected dose per gram of at 24 h, respectively) favourably compared to the biodistribution data obtained in the same animal model using two high-affinity human monoclonal antibodies in IgG format.

Preparation of a Radiolabelled Ligand Having CAIX Binding Property

An anti-CAIX ligand having the following chemical structure:

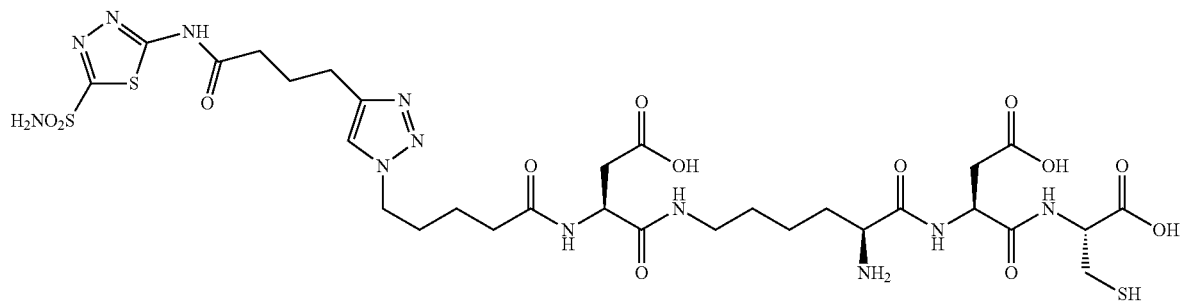 [SMILES: N[C@@H](CCCCNC(=O)[C@H](CC(=O)O)NC(=O)CCCCn1cc(CCCC(=O)Nc2nnc(S(N)(=O)=O)s2)nn1)C(=O)N[C@@H](CC(=O)O)C(=O)N[C@@H](CS)C(=O)O]

was radiolabelled with Technetium 99m as follows. 50 µL ligand (1.2 mM) in degassed PBS pH 7.4 was mixed with 50 µL SnCl$_2$ (4 mg/mL) freshly prepared solution in degassed MQ water, 100 µL Na glucoheptonate (200 mg/mL) freshly prepared in degassed MQ water, and 600 µL TBS pH 7.4. The solution was degassed for at least 5 min by bubbling nitrogen. 200 µL $^{99m}$Tc generator eluate (ca. 200 MBq) was added to the solution, which was then heated to 90° C. for 20 min and left to cool to room temperature.

Evaluation of Biodistribution of Radiolabelled Anti-CAIX Ligand

The biodistribution performance of the Technetium 99m labelled ligand in mice was assessed as follows. Balb/c nu/nu mice were injected subcutaneously with 10$^7$ SKRC52 renal cell carcinoma cells. Established SKRC52 tumors were allowed to grow to an average size of 500 mm$^3$ before receiving intravenous injections of the radiolabelled ligand. An untargeted/irrelevant ligand was also radiolabelled with Technetium 99m and used as negative control.

Six hours after injection mice were sacrificed, individual organs were excised and analyzed for radiolabelled ligand uptake.

Figure 19:
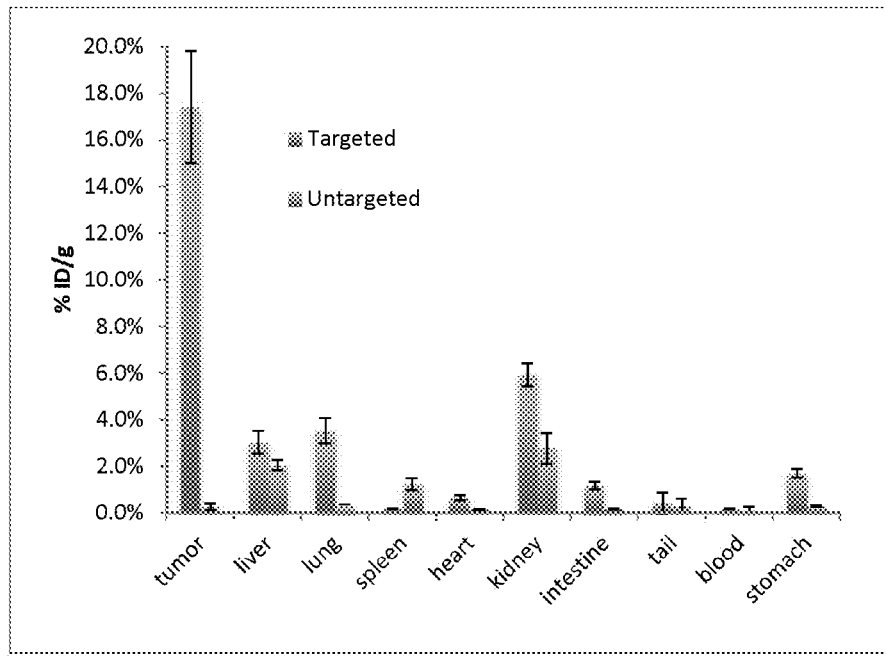
FIG. 19 shows comparative uptake data for different organs in a mouse having renal carcinoma of a radiolabelled anti-CAIX targeted ligand versus a radiolabelled untargeted ligand.
Figure 21:
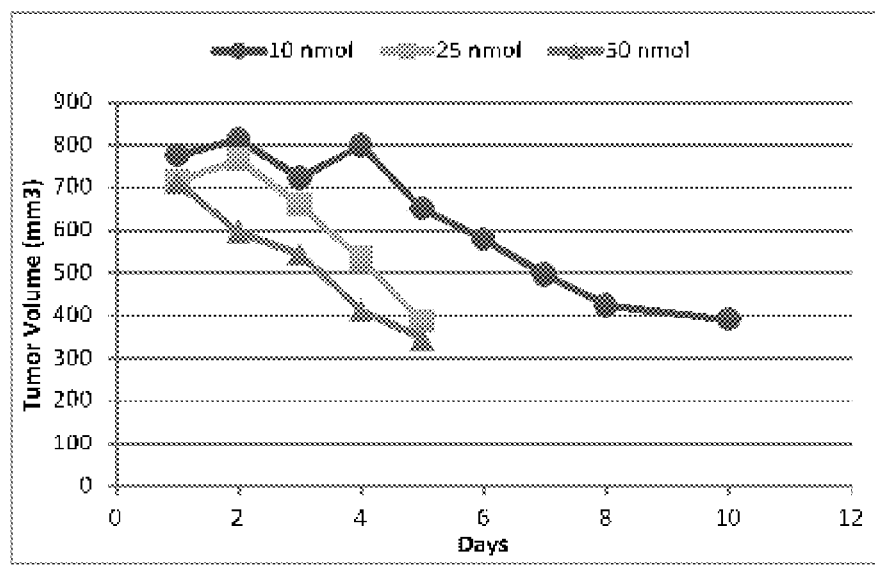
FIG. 21 shows data observed for mouse tumor size versus time for three dosage regimes of the drug conjugate of FIG. 20

The results expressed as Injected dose per gram of tissue are shown in FIG. 19 It can be seen that the CAIX ligand strongly localized in the tumor as compared to the untargeted ligand.

Synthesis of an Auristatin Drug Conjugated to a Small Molecule CAIX Binding Moiety Having a Peptide Linker that is Cleavable by Cathepsin B The reaction scheme and the structure of the drug conjugate of this example according to the present invention are shown in FIG. 19.

The peptide AAZ-triazole-AspArgAspCys-COOH (1) was prepared as described previously (Krall et. al., Angew. Chem. Int. Ed. 2014, 53, 4231). A solution of 1 (4.5 mg, 5 µmol) in degassed PBS pH 7.4 (1 mL) was added to commercially available Maleimido Caproyl Valine Citrulline Para-Amino Benzyl carbamate of Mono Methyl Auristatin E (MC-VC-PAB-MMAE (2), 6.5 mg, 4.9 µmol) and allowed to stand at room temperature for 5 min MMAE is the toxic moiety. MC-VC-PAB is the cleavable linker.

The mixture was purified over HPLC (Synergi RP Polar, 5% MeCN in 0.1% aq. TFA to 80% over 20 min) and product containing fractions identified by low-resolution mass spectrometry. After lyophilization the product was collect as a white powder (7.5 mg, 3.4 µmol, 68%). HRMS: (m/z)[M+2H$^+$]  $C_{98}H_{153}N_{25}O_{28}S_3$, 1112.0234. found 1112.0237.

Evaluation of the Antitumor Activity of the Auristatin Conjugate with CAIX Binding Moiety and Cathepsin B-Cleavable Peptide Linker.

The antitumor activity of the drug conjugate according to the present invention as shown in FIG. 19 was evaluated as follows. The results are shown graphically in FIG. 20.

Balb/c nu/nu mice were injected subcutaneously with 10$^7$ SKRC52 renal cell carcinoma cells. Established SKRC52 tumors were allowed to grow to an average size of 700 mm$^3$ before receiving intravenous injections of the SMDC at the following doses and schedules: 50 nm on day 1 only; 25 nm each on day 1 and day 2; and 10 nm each on days 1, 2, 3, 4 and 5. Tumor volumes were recorded daily with the aid of a digital caliper. A significant antitumor activity was observed even at the lowest dose of 10 nmoles.

Figure 20:
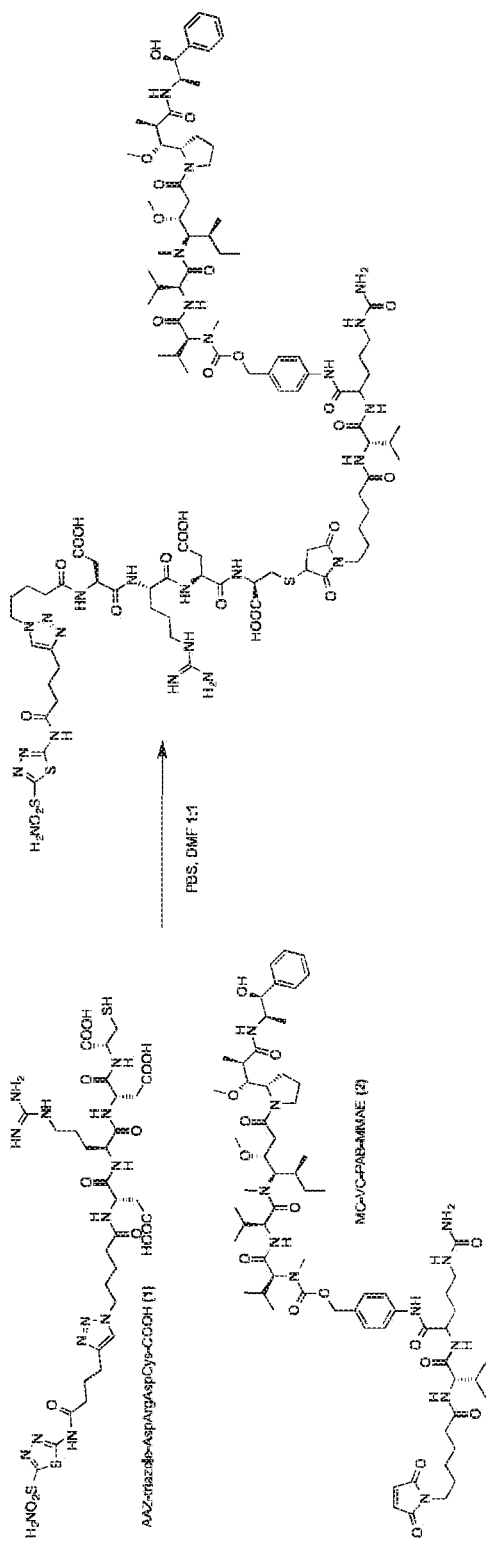
FIG. 20 shows a reaction scheme for the synthesis of a targeted cytotoxic drug conjugate according to the present invention having the drug auristatin linked to a small molecule binding moiety through a valine-citrulline containing peptide linker that is cleavable by Cathepsin B.

FIG. 20 shows that a strong antitumor activity of the SMDC was observed in the SKRC52 renal cell carcinoma model established in nude mice. The regression of tumors with the size of 700 mm$^3$ was observed with different doses and treatment regimes.

All patent documents and other references cited herein are expressly incorporated herein by reference.

The above embodiments of the invention have been described for the purpose of illustration only. Many other embodiments falling within the scope of the accompanying claims will be apparent to the skilled reader.

REFERENCES

[1] T. Iwakiri, M. Okumura, M. Hidaka, Y. Kumagai, E. Ichihara, Y. Kawano, K. Arimori, *J. Appl. Toxicol.* 2008, 28, 329.

[2] H. H. Ku, *J. Res. Nat. Bur. Stand. Sec. C: Eng. Inst.* 1966, 70C, 263.

[3] J. K. Ahlskog, C. Schliemann, J. Marlind, U. Qureshi, A. Ammar, R. B. Pedley, D. Neri, *Br. J. Cancer* 2009, 101, 645.

[4] Z. Nikolovska-Coleska, R. Wang, X. Fang, H. Pan, Y. Tomita, P. Li, P. P. Roller, K. Krajewski, N. G. Saito, J. A. Stuckey, S. Wang, *Anal. Biochem.* 2004, 332, 261.

[5] K. Frey, C. Schliemann, K. Schwager, R. Giavazzi, M. Johannsen, D. Neri, *J. Urology* 2010, 184, 2540.

[6] M. Steiner, K. Gutbrodt, N. Krall, D. Neri, *Bioconj. Chem.* 2013, 24, 234.

[7] E. Oroudjev, M. Lopus, L. Wilson, C. Audette, C. Provenzano, H. Erickson, Y. Kovtun, R. Chan, M. A. Jordan, *Mol. Cancer. Ther.* 2010, 9, 2700.

[8] M. Lapeyre, J. Leprince, M. Massonneau, H. Oulyadi, P. Y. Renard, A. Romieu, G. Turcatti, H. Vaudry, *Chemistry* 2006, 12, 3655.

[9] A. El Alaoui, F. Schmidt, M. Amessou, M. Sarr, D. Decaudin, J. C. Florent, L. Johannes, *Angew. Chem. Int. Ed.* 2007, 46, 6469.

[10] L. F. Tietze, F. Major, *Eur. J. Org. Chem.* 2006, 2314.

[11] R. N. Zuckermann, et al., *J. Med. Chem.* 1994, 37, 2678.

[12] J. T. t. Lundquist, J. C. Pelletier, *Org. Lett.* 2001, 3, 781.

[13] F. Carta, V. Garaj, A. Maresca, J. Wagner, B. S. Avvaru, A. H. Robbins, A. Scozzafava, R. McKenna, C. T. Supuran, *Bioorg. Med. Chem.* 2011, 19, 3105.

[14] K. M. Amore, N. E. Leadbeater, T. A. Miller, J. R. Schmink, *Tet. Lett.* 2006, 47, 8583.

[15] A. W. Schuttelkopf, L. Gros, D. E. Blair, J. A. Frearson, D. M. van Aalten, I. H. Gilbert, *Bioorg. Med. Chem.* 2010, 18, 8334.

[16] G. Chouhan, K. James, *Org. Lett.* 2011, 13, 2754.

The invention claimed is:
1. A ligand specific for CAIX having the formula:

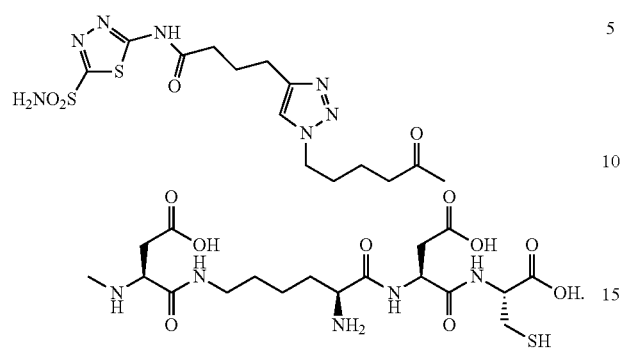

2. The ligand of claim 1, wherein said ligand comprises a radiolabel.
3. The ligand of claim 2, wherein said radiolabel is Technetium.
4. A pharmaceutical composition comprising a targeted therapeutic agent comprising the ligand of claim 1.
5. The pharmaceutical composition of claim 4, wherein said ligand comprises a radiolabel.
6. The pharmaceutical composition of claim 5, wherein said radiolabel is Technetium.

* * * * *

SEQUENCE LISTING

```
<160> NUMBER OF SEQ ID NOS: 6

<210> SEQ ID NO 1
<211> LENGTH: 4
<212> TYPE: PRT
<213> ORGANISM: artificial
<220> FEATURE:
<223> OTHER INFORMATION: synthetic

<400> SEQUENCE: 1
```

Cys Asp Arg Asp
1

<210> SEQ ID NO 2
<211> LENGTH: 48
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (25)..(30)
<223> OTHER INFORMATION: n is a, c, g, or t

<400> SEQUENCE: 2
ggagcttctg aattctgtgt gctgnnnnnn cgagtcccat ggcgcagc        48

<210> SEQ ID NO 3
<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (12)..(19)
<223> OTHER INFORMATION: n = a deoxyabasic site

<400> SEQUENCE: 3
catgggactc gnnnnnnnnc agcacacaga attcagaagc tcc         43

<210> SEQ ID NO 4
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (22)..(29)
<223> OTHER INFORMATION: n is a, c, g, or t

<400> SEQUENCE: 4
cctgcatcga atggatccgt gnnnnnnnng cagctgcgc       39

<210> SEQ ID NO 5
<211> LENGTH: 21
<212> TYPE: DNA
<213> ORGANISM: artificial
<220> FEATURE:
<223> OTHER INFORMATION: synthetic

<400> SEQUENCE: 5
cgagtcccat ggcgcagctg c        21

<210> SEQ ID NO 6
<211> LENGTH: 4
<212> TYPE: PRT
<213> ORGANISM: artificial
<220> FEATURE:
<223> OTHER INFORMATION: synthetic

<400> SEQUENCE: 6

Asp Arg Asp Cys
1